United States Patent
Howell et al.

(10) Patent No.: US 11,372,003 B2
(45) Date of Patent: Jun. 28, 2022

(54) BIOMARKERS FOR GRAFT-VERSUS-HOST DISEASE

(71) Applicant: Incyte Corporation, Wilmington, DE (US)

(72) Inventors: Michael D. Howell, Kennett Square, PA (US); Hao Liu, Pennington, NJ (US); Michael A. Pratta, Mullica Hill, NJ (US)

(73) Assignee: Incyte Corporation, Wilmington, DE (US)

( * ) Notice: Subject to any disclaimer, the term of this patent is extended or adjusted under 35 U.S.C. 154(b) by 102 days.

(21) Appl. No.: 16/381,158

(22) Filed: Apr. 11, 2019

(65) Prior Publication Data

US 2019/0331697 A1 Oct. 31, 2019

Related U.S. Application Data

(60) Provisional application No. 62/773,308, filed on Nov. 30, 2018, provisional application No. 62/657,193, filed on Apr. 13, 2018.

(51) Int. Cl.
| | |
|---|---|
| A61P 37/06 | (2006.01) |
| A61K 31/519 | (2006.01) |
| A61K 31/573 | (2006.01) |
| A61K 45/06 | (2006.01) |
| G01N 33/68 | (2006.01) |

(52) U.S. Cl.
CPC ....... *G01N 33/6893* (2013.01); *A61K 31/519* (2013.01); *A61K 31/573* (2013.01); *A61K 45/06* (2013.01); *A61P 37/06* (2018.01); *G01N 2800/245* (2013.01); *G01N 2800/52* (2013.01); *G01N 2800/60* (2013.01)

(58) Field of Classification Search
CPC . A61P 37/06; A61K 31/519; G01N 2800/245; G01N 2800/52; G01N 2800/60
See application file for complete search history.

(56) References Cited

U.S. PATENT DOCUMENTS

| | | | |
|---|---|---|---|
| 5,057,313 A | 10/1991 | Shih et al. | |
| 5,156,840 A | 10/1992 | Goers et al. | |
| 7,335,667 B2 | 2/2008 | Rodgers et al. | |
| 7,598,257 B2 | 10/2009 | Rodgers et al. | |
| 7,834,022 B2 | 11/2010 | Rodgers et al. | |
| 8,158,616 B2 | 4/2012 | Rodgers et al. | |
| 8,309,718 B2 | 11/2012 | Li et al. | |
| 8,410,265 B2 | 4/2013 | Zhou et al. | |
| 8,486,902 B2 | 7/2013 | Rodgers et al. | |
| 8,513,270 B2 | 8/2013 | Arvanitis et al. | |
| 8,563,541 B2 | 10/2013 | Arvanitis et al. | |
| 8,604,043 B2 | 12/2013 | Li et al. | |
| 8,691,807 B2 | 4/2014 | Yao et al. | |
| 8,716,303 B2 | 5/2014 | Rodgers et al. | |
| 8,722,693 B2 | 5/2014 | Rodgers et al. | |
| 8,765,734 B2 | 7/2014 | Huang et al. | |
| 8,933,085 B2 | 1/2015 | Rodgers et al. | |
| 8,987,443 B2 | 3/2015 | Liu et al. | |
| 9,034,884 B2 | 5/2015 | Rodgers et al. | |
| 9,181,271 B2 | 11/2015 | Li et al. | |
| 9,193,733 B2 | 11/2015 | Rodgers et al. | |
| 9,249,145 B2 | 2/2016 | Rodgers et al. | |
| 9,249,149 B2 | 2/2016 | Silverman et al. | |
| 9,358,229 B2 | 6/2016 | Vannucchi et al. | |
| 9,359,358 B2 | 6/2016 | Rodgers et al. | |
| 9,382,231 B2 | 7/2016 | Li et al. | |
| 9,487,521 B2 | 11/2016 | Zhou et al. | |
| 9,498,467 B2 | 11/2016 | Leopold et al. | |
| 9,540,367 B2 | 1/2017 | Tung et al. | |
| 9,655,854 B2 | 5/2017 | Yeleswaram et al. | |
| 9,802,957 B2 | 10/2017 | Zhou et al. | |
| 9,993,480 B2 | 6/2018 | Vannucchi et al. | |
| 10,166,191 B2 | 1/2019 | Ni et al. | |
| 2003/0013208 A1 | 1/2003 | Jendoubi et al. | |
| 2004/0171068 A1 | 9/2004 | Wehland et al. | |
| 2006/0106020 A1 | 5/2006 | Rodgers et al. | |
| 2010/0113416 A1 | 5/2010 | Friedman et al. | |
| 2010/0298334 A1 | 11/2010 | Ridgers et al. | |
| 2011/0059951 A1 | 3/2011 | Rodgers et al. | |
| 2011/0149681 A1 | 6/2011 | Hovland et al. | |
| 2011/0207754 A1 | 8/2011 | Li et al. | |
| 2011/0224190 A1 | 9/2011 | Huang et al. | |
| 2011/0288107 A1 | 11/2011 | Parikh et al. | |
| 2012/0149682 A1 | 6/2012 | Rodgers et al. | |
| 2013/0018034 A1 | 1/2013 | Yao et al. | |

(Continued)

FOREIGN PATENT DOCUMENTS

| | | |
|---|---|---|
| WO | WO 2013/066369 | 5/2013 |
| WO | WO 2016/085866 | 6/2016 |
| WO | WO 2019/200030 | 10/2019 |

OTHER PUBLICATIONS

Mori (Bone Marrow Transplantation vol. 51 pp. 1584-1587 published 2016) (Year: 2016).*
Invitation to Pay Additional Fees in International Application No. PCT/US2020/054813, dated Dec. 18, 2020, 20 pages.
Invitation to Pay Additional Fees in International Application No. PCT/US2020/054836, dated Dec. 21, 2020, 17 pages.
Pratta et al., "4559: Plasma biomarker association with response in acute GVHD subjects treated with the combination of itacitinib and corticosteroids in a phase 1 clinical trial," Blood, Nov. 1, 2018, 132(Suppl.1):4559.

(Continued)

*Primary Examiner* — Theodore R. Howell
*Assistant Examiner* — George W Kosturko
(74) *Attorney, Agent, or Firm* — Fish & Richardson P.C.

(57) ABSTRACT

Biomarkers are provided that are predictive of a subject's responsiveness to a therapy comprising a JAK inhibitor. The biomarkers, compositions, and methods described herein are useful in selecting appropriate treatment modalities for a subject having, suspected of having, or at risk of developing Graft-Versus-Host Disease.

34 Claims, No Drawings

(56) References Cited

U.S. PATENT DOCUMENTS

| | | | |
|---|---|---|---|
| 2013/0045963 A1 | 2/2013 | Rodgers et al. | |
| 2013/0060026 A1* | 3/2013 | Zhou | A61P 43/00 |
| | | | 544/229 |
| 2013/0115232 A1* | 5/2013 | Ferrara | G01N 33/6893 |
| | | | 424/184.1 |
| 2014/0005166 A1 | 1/2014 | Rodgers et al. | |
| 2014/0121198 A1 | 5/2014 | Li et al. | |
| 2014/0256941 A1 | 9/2014 | Liu et al. | |
| 2014/0343030 A1 | 11/2014 | Li et al. | |
| 2015/0065447 A1 | 3/2015 | Sandor | |
| 2015/0246046 A1 | 9/2015 | Vaddi | |
| 2015/0344497 A1 | 12/2015 | Zhou et al. | |
| 2019/0175578 A1 | 6/2019 | Koblish et al. | |
| 2019/0233392 A1 | 8/2019 | Wang et al. | |
| 2019/0255053 A1 | 8/2019 | Montgomery et al. | |
| 2019/0328739 A1 | 10/2019 | Howell et al. | |
| 2020/0063188 A1 | 2/2020 | Howell et al. | |
| 2020/0129517 A1 | 4/2020 | Assad | |
| 2020/0197399 A1 | 6/2020 | Yeleswaram et al. | |
| 2021/0123930 A1 | 4/2021 | Howell et al. | |
| 2021/0123931 A1 | 4/2021 | Howell et al. | |

OTHER PUBLICATIONS

Pratta et al., "Predicting Complete Response to Itacitinib and Corticosteroids in Acute Graft Versus Host Disease," Biol Blood Marrow Transplant., Jan. 23, 2020, 26(3):270.

International Search Report and Written Opinion in International Appln. No. PCT/US2020/054813, dated Feb. 9, 2021, 25 pages.

International Search Report and Written Opinion in International Appln. No. PCT/US2020054836, dated Feb. 11, 2021, 22 pages.

Addona et al., "Multi-site assessment of the precision and reproducibility of multiple reaction monitoring-based measurements of proteins in plasma," Nat. Biotechnol., Jul. 2009, 27:633-641.

Atzrodt et al., "The Renaissance of H/D Exchange," Angew. Chem. Int. Ed., Oct. 4, 2007, 46:7744-7765.

Betts et al., "Targeting JAK2 1-47 reduces GVHD and xenograft rejection through regulation of T cell differentiation," Proceedings of the National Academy of Sciences of the U.S.A., Jan. 30, 2018, 115:1582-1587.

Carniti et al., "Pharmacologic 1-47 Inhibition of JAK1/JAK2 Signaling Reduces Experimental Murine Acute GVHD While Preserving GVT Effects," Clinical Cancer Research, May 14, 2015, 21:3740-3749.

Chen et al.,"Trial in progress: Gravitas-301, a randomized, double-blind phase 3 study of itacitinib or placebo with corticosteroids (CS) for the first-line treatment of patients with acute Gvhd (aGVHD)," Elsevier Science Publishers, Mar. 1, 2018, Sumniaiy of Trial, 2 pages.

Hartwell et al., "An early-biomarker algorithm predicts lethal graftversus-host disease and survival," JCI Insight, Feb. 9, 2017, 2(3).

Huston et al., "Protein engineering of antibody binding sites: recovery of specific activity in an anti-digoxin single-chain Fv analogue produced in *Escherichia coli*," Proc. Natl. Acad. Sci. USA, Aug. 1988, 85:5879-5883.

International Preliminary Report on Patentability in International Application No. PCT/2020/026884, dated Oct. 13, 2020, 8 pages.

International Search Report and Written Opinion in International Appln. No. PCT/2019/026884, dated Mar. 6, 2019, 9 pages.

Kerekes et al., "Aurora Kinase Inhibitors Based on the Imidazo[1,2-a]pyrazine Core: Fluorine and Deuterium Incorporation Improve Oral Absorption and Exposure," J. Med. Chem., Dec. 3, 2010, 54:201-210.

Kuzyk et al., "Multiple Reaction Monitoring-based, Multiplexed, Absolute Quantitation of 45 Proteins in Human Plasma," Mol. Cell Proteomics, Aug. 1, 2009, 8:1860-1877.

Mori et al.,"Ruxolitinib treatment for 19-24 GvHD in patients with myelofibrosis," Bone Marrow Transplantation, Oct. 10, 2016, 51:1584-1587.

Paulovich et al., "The interface between biomarker discovery and clinical validation: The tar pit of the protein biomarker pipeline," Proteomics Clin. Appl., Apr. 2008, 2:1386-1402.

Sadeghi et al., "Early-phase GVHD gene expression profile in target versus non-target tissues: kidney, a possible target?" Bone Marrow Transplantation, Jul. 23, 2012, 48: 284-293.

Xu et al., "Design, synthesis and biological evaluation of deuterated nintedanib for improving pharmacokinetic properties," J. Label Compd. Radiopharm, May 26, 2015, 58:308-312.

\* cited by examiner

BIOMARKERS FOR GRAFT-VERSUS-HOST DISEASE

CROSS-REFERENCE TO RELATED APPLICATIONS

This application claims priority to U.S. Provisional Appl. No. 62/657,193, filed Apr. 13, 2018, and U.S. Provisional Appl. No. 62/773,308, filed Nov. 30, 2018. The content of the prior applications are incorporated by reference herein in their entirety.

TECHNICAL FIELD

The present invention relates generally to biomarkers and Graft-Versus-Host Disease.

BACKGROUND

Graft-Versus-Host Disease (GvHD) occurs when immunologically competent cells transferred to an allogeneic recipient attack tissues in the recipient. Tissues of the skin, gut epithelia, and liver are often targets and may be destroyed during the course of GvHD. The disease presents an especially severe problem when immune tissue is being transplanted, such as in bone marrow transplantation. GvHD is the second leading cause of death following allogeneic hematopoietic stem cell transplant. GvHD can also occur following other transplants, such as heart and liver transplants.

Janus kinase (JAK) inhibitors have been developed as agents for the treatment of GvHD. However, as for any therapeutic, JAK inhibitors may not be equally effective in all subjects that have GvHD. There is a need for means of identifying those subjects having GvHD that could most benefit from treatment with a JAK inhibitor as well as identifying those subjects that exhibit a therapeutic response to treatment with a JAK inhibitor.

SUMMARY

The present application is based, at least in part, on the identification of biomarkers that are predictive of a GvHD subject's responsiveness to a therapy comprising a JAK inhibitor and biomarkers that identify a subject that has undergone a therapeutic response to a JAK inhibitor. The level of certain proteins (e.g., the proteins listed in Table 1 and Table 2) prior to treatment is identified as a useful predictor of responsiveness to a therapy comprising a JAK inhibitor. In addition, the change in level of certain proteins (e.g., the proteins listed in Table 13) during the course of treatment is identified as a useful identifier of responsiveness to a therapy comprising a JAK inhibitor. Thus, the biomarkers and compositions described herein are useful, for example, in identifying, stratifying, and/or selecting a patient or a subset of patients having, suspected of having, or at risk of developing GvHD that could benefit, or have benefitted, from treatment with a JAK inhibitor. In addition, the methods described herein are useful, for example, in selecting appropriate treatment modalities (e.g., therapy comprising a JAK inhibitor) for a subject suffering from, suspected of having, or at risk of developing GvHD.

The disclosure features a method of treating a human subject having, suspected of having, or at risk of developing GvHD by administering to the human subject a therapy comprising a JAK inhibitor, wherein the human subject has been previously determined to have (i) a baseline concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of IL8, HAOX1, ENPP7, ACE2, SULT2A1, MCP-3, CES1, MFGE8, PLXNB1, TNFRSF10A, CCL15, SEMA4C, PREB, NFATC3, CCL19, DLL1, ENTPD2, IL-4RA, EPHA2, FOSB, CXCL10, VAMP5, ALDH3A1, MVK, IL12RB1, CALCA, AHCY, PRSS2, LILRB4, DDAH1, IL-1ra, NECTIN2, PDCD1, CD74, PD-L1, REG3A, CA5A, N2DL-2, CDCP1, U-PAR, SIGLEC7, ANGPTL4, ALDH1A1, SPINK1, HTRA2, PRDX6, IL-1RT2, IGFBP-1, HNMT, TRAIL-R2, CXADR, CTSL1, IFN-gamma-R1, IL-18R1, KRT19, KYNU, and TGM2 in a biological sample obtained from the human subject that is lower than a control, and/or (ii) a baseline concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of PON3, CNTN1, IGFBP3, LEP, Notch 3, TN-R, HSD11B1, FAM19A5, NCAN, F11, GDF-8, CCL28, GALNT10, BCAN, TIMP4, CRISP2, CD207, WNT9A, MBL2, EN-RAGE, TWEAK, CR2, MFAP5, KIT, GH, PFKM, CDSN, CRH, GCP5, KLK6, and DRAXIN in a biological sample obtained from the human subject that is higher than a control.

In some embodiments, the human subject has been previously determined to have (i) a baseline concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of MCP-3, HAOX1, CA5A, CALCA, IL8, SULT2A1, VAMP5, SPINK1, ENPP7, ACE2, CTSL1, PRSS2, CXCL10, MFGE8, KRT19, ALDH1A1, CES1, REG3A, KYNU, IL-4RA, CDCP1, MVK, FOSB, NFATC3, N2DL-2, DDAH1, IGFBP-1, ALDH3A1, CXADR, PLXNB1, CD74, ENTPD2, PREB, CCL19, HNMT, HTRA2, IL-1RT2, and IL-18R1 in a biological sample obtained from the human subject that is lower than a control, and/or (ii) a baseline concentration of at least one protein (e.g., at least 1, 2, 3, 4, 5, 6, 7, or 8 proteins) selected from the group consisting of PON3, LEP, MBL2, GH, GDF-8, EN-RAGE, CRISP2, and CR2 in a biological sample obtained from the human subject that is higher than a control.

In some embodiments, the human subject has been previously determined to have (i) a baseline concentration of at least one protein (e.g., at least 1, 2, 3, 4, 5, 6, 7, 8, 9, 10, 11, 12, 13, 14, 15, or 16 proteins) selected from the group consisting of MCP-3, HAOX1, CA5A, CALCA, IL8, SULT2A1, VAMP5, SPINK1, ENPP7, ACE2, CTSL1, PRSS2, CXCL10, MFGE8, KRT19, and ALDH1A1 in a biological sample obtained from the human subject that is lower than a control, and/or (ii) a baseline concentration of at least one protein (e.g., at least 1, 2, or 3 proteins) selected from the group consisting of PON3, LEP, and MBL2 in a biological sample obtained from the human subject that is higher than a control.

In some embodiments, the human subject has been previously determined to have (i) a baseline concentration of at least one protein (e.g., at least 1, 2, 3, 4, 5, 6, 7, or 8 proteins) selected from the group consisting of MCP-3, HAOX1, CA5A, CALCA, IL8, SULT2A1, VAMP5, and SPINK1 in a biological sample obtained from the human subject that is lower than a control, and/or (ii) a baseline concentration of at least one protein (e.g., at least 1 or 2 proteins) selected from the group consisting of PON3 and LEP in a biological sample obtained from the human subject that is higher than a control.

The disclosure also features a method of treating a human subject having, suspected of having, or at risk of developing GvHD, by: providing a biological sample obtained from the human subject; measuring in the biological sample a reduced concentration, as compared to a control, of at least one protein (e.g., at least 1, 2, 3, 4, 5, 6, 7, 8, 9, 10, 11, 12, 13, 14, 15, 16, 17, 18, 19, or 20 proteins) selected from the group consisting of IL8, HAOX1, ENPP7, ACE2, SULT2A1, MCP-3, CES1, MFGE8, PLXNB1, TNFRSF10A, CCL15, SEMA4C, PREB, NFATC3, CCL19, DLL1, ENTPD2, IL-4RA, EPHA2, FOSB, CXCL10, VAMP5, ALDH3A1, MVK, IL12RB1, CALCA, AHCY, PRSS2, LILRB4, DDAH1, IL-1ra, NECTIN2, PDCD1, CD74, PD-L1, REG3A, CA5A, N2DL-2, CDCP1, U-PAR, SIGLEC7, ANGPTL4, ALDH1A1, SPINK1, HTRA2, PRDX6, IL-1RT2, IGFBP-1, HNMT, TRAIL-R2, CXADR, CTSL1, IFN-gamma-R1, IL-18R1, KRT19, KYNU, and TGM2, and/or an increased concentration, as compared to a control, of at least one protein (e.g., at least 1, 2, 3, 4, 5, 6, 7, 8, 9, 10, 11, 12, 13, 14, 15, 16, 17, 18, 19, or 20 proteins) selected from the group consisting of PON3, CNTN1, IGFBP3, LEP, Notch 3, TN-R, HSD11B1, FAM19A5, NCAN, F11, GDF-8, CCL28, GALNT10, BCAN, CRISP2, CD207, WNT9A, MBL2, EN-RAGE, TWEAK, CR2, MFAP5, KIT, GH, PFKM, CDSN, CRH, GCP5, KLK6, and DRAXIN; and administering a therapy comprising a JAK inhibitor to the human subject.

In some embodiments, the method includes: measuring in the biological sample a reduced concentration, as compared to a control, of at least one protein (e.g., at least 1, 2, 3, 4, 5, 6, 7, 8, 9, 10, 11, 12, 13, 14, 15, 16, 17, 18, 19, or 20 proteins) selected from the group consisting of MCP-3, HAOX1, CA5A, CALCA, IL8, SULT2A1, VAMP5, SPINK1, ENPP7, ACE2, CTSL1, PRSS2, CXCL10, MFGE8, KRT19, ALDH1A1, CES1, REG3A, KYNU, IL-4RA, CDCP1, MVK, FOSB, NFATC3, N2DL-2, DDAH1, IGFBP-1, ALDH3A1, CXADR, PLXNB1, CD74, ENTPD2, PREB, CCL19, HNMT, HTRA2, IL-1RT2, and IL-18R1, and/or an increased concentration, as compared to a control, of at least one protein (e.g., at least 1, 2, 3, 4, 5, 6, 7, or 8 proteins) selected from the group consisting of PON3, LEP, MBL2, GH, GDF-8, EN-RAGE, CRISP2, and CR2; and administering the therapy comprising the JAK inhibitor to the human subject.

In some embodiments, the method includes: measuring in the biological sample a reduced concentration, as compared to a control, of at least one protein (e.g., at least 1, 2, 3, 4, 5, 6, 7, 8, 9, 10, 11, 12, 13, 14, 15, or 16 proteins) selected from the group consisting of MCP-3, HAOX1, CA5A, CALCA, IL8, SULT2A1, VAMP5, SPINK1, ENPP7, ACE2, CTSL1, PRSS2, CXCL10, MFGE8, KRT19, and ALDH1A1, and/or an increased concentration, as compared to a control, of at least one protein (e.g., at least 1, 2, or 3 proteins) selected from the group consisting of PON3, LEP, and MBL2; and administering the therapy comprising the JAK inhibitor to the human subject.

In some embodiments, the method includes: measuring in the biological sample a reduced concentration, as compared to a control, of at least one protein (e.g., at least 1, 2, 3, 4, 5, 6, 7, or 8 proteins) selected from the group consisting of MCP-3, HAOX1, CASA, CALCA, IL8, SULT2A1, VAMP5, and SPINK1, and/or an increased concentration, as compared to a control, of at least one protein (e.g., at least 1 or 2 proteins) selected from the group consisting of PON3 and LEP; and administering the therapy comprising the JAK inhibitor to the human subject.

The disclosure also features a method of predicting the response of a human subject having, suspected of having, or at risk of developing GvHD to a therapy comprising a JAK inhibitor, by: providing a biological sample obtained from the subject before the therapy comprising the JAK inhibitor; and measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of PON3, CNTN1, IGFBP3, LEP, Notch 3, TN-R, HSD11B1, FAM19A5, NCAN, F11, GDF-8, CCL28, GALNT10, BCAN, TIMP4, CRISP2, CD207, WNT9A, MBL2, EN-RAGE, TWEAK, CR2, MFAP5, KIT, GH, PFKM, CDSN, CRH, GCP5, KLK6, DRAXIN, IL8, HAOX1, ENPP7, ACE2, SULT2A1, MCP-3, CES1, MFGE8, PLXNB1, TNFRSF10A, CCL15, SEMA4C, PREB, NFATC3, CCL19, DLL1, ENTPD2, IL-4RA, EPHA2, FOSB, CXCL10, VAMP5, ALDH3A1, MVK, IL12RB1, CALCA, AHCY, PRSS2, LILRB4, DDAH1, IL-1ra, NECTIN2, PDCD1, CD74, PD-L1, REG3A, CA5A, N2DL-2, CDCP1, U-PAR, SIGLEC7, ANGPTL4, ALDH1A1, SPINK1, HTRA2, PRDX6, IL-1RT2, IGFBP-1, HNMT, TRAIL-R2, CXADR, CTSL1, IFN-gamma-R1, IL-18R1, KRT19, KYNU, and TGM2 in the biological sample, wherein a reduced concentration, as compared to a control, of at least one (e.g., at least 1, 2, 3, 4, 5, 6, 7, 8, 9, 10, 11, 12, 13, 14, 15, 16, 17, 18, 19, or 20) of IL8, HAOX1, ENPP7, ACE2, SULT2A1, MCP-3, CES1, MFGE8, PLXNB1, TNFRSF10A, CCL15, SEMA4C, PREB, NFATC3, CCL19, DLL1, ENTPD2, IL-4RA, EPHA2, FOSB, CXCL10, VAMP5, ALDH3A1, MVK, IL12RB1, CALCA, AHCY, PRSS2, LILRB4, DDAH1, IL-1ra, NECTIN2, PDCD1, CD74, PD-L1, REG3A, CA5A, N2DL-2, CDCP1, U-PAR, SIGLEC7, ANGPTL4, ALDH1A1, SPINK1, HTRA2, PRDX6, IL-1RT2, IGFBP-1, HNMT, TRAIL-R2, CXADR, CTSL1, IFN-gamma-R1, IL-18R1, KRT19, KYNU, or TGM2, and/or an increased concentration, as compared to a control, of at least one (e.g., at least 1, 2, 3, 4, 5, 6, 7, 8, 9, 10, 11, 12, 13, 14, 15, 16, 17, 18, 19, or 20) of PON3, CNTN1, IGFBP3, LEP, Notch 3, TN-R, HSD11B1, FAM19A5, NCAN, F11, GDF-8, CCL28, GALNT10, BCAN, TIMP4, CRISP2, CD207, WNT9A, MBL2, EN-RAGE, TWEAK, CR2, MFAP5, KIT, GH, PFKM, CDSN, CRH, GCP5, KLK6, or DRAXIN is predictive that the subject will respond to the therapy comprising the JAK inhibitor.

In some embodiments, the method includes: measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of PON3, LEP, MBL2, GH, GDF-8, EN-RAGE, CRISP2, CR2, MCP-3, HAOX1, CA5A, CALCA, IL8, SULT2A1, VAMP5, SPINK1, ENPP7, ACE2, CTSL1, PRSS2, CXCL10, MFGE8, KRT19, ALDH1A1, CES1, REG3A, KYNU, IL-4RA, CDCP1, MVK, FOSB, NFATC3, N2DL-2, DDAH1, IGFBP-1, ALDH3A1, CXADR, PLXNB1, CD74, ENTPD2, PREB, CCL19, HNMT, HTRA2, IL-1RT2, and IL-18R1 in the biological sample, wherein a reduced concentration, as compared to a control, of at least one (e.g., at least 1, 2, 3, 4, 5, 6, 7, 8, 9, 10, 11, 12, 13, 14, 15, 16, 17, 18, 19, or 20) of MCP-3, HAOX1, CA5A, CALCA, IL8, SULT2A1, VAMP5, SPINK1, ENPP7, ACE2, CTSL1, PRSS2, CXCL10, MFGE8, KRT19, ALDH1A1, CES1, REG3A, KYNU, IL-4RA, CDCP1, MVK, FOSB, NFATC3, N2DL-2, DDAH1, IGFBP-1, ALDH3A1, CXADR, PLXNB1, CD74, ENTPD2, PREB, CCL19, HNMT, HTRA2, IL-1RT2, or IL-18R1, and/or an increased concentration, as compared to a control, of at least one (e.g., at least 1, 2, 3, 4, 5, 6, 7, or 8) of PON3, LEP, MBL2, GH, GDF-8, EN-RAGE, CRISP2, or CR2 is predictive that the subject will respond to the therapy comprising the JAK inhibitor.

In some embodiments, the method includes: measuring the concentration of at least one protein (e.g., at least 1, 2, 3, 4, 5, 6, 7, 8, 9, 10, 11, 12, 13, 14, 15, 16, 17, 18, or 19 proteins) selected from the group consisting of PON3, LEP, MBL2, MCP-3, HAOX1, CA5A, CALCA, IL8, SULT2A1, VAMP5, SPINK1, ENPP7, ACE2, CTSL1, PRSS2, CXCL10, MFGE8, KRT19, and ALDH1A1 in the biological sample, wherein a reduced concentration, as compared to a control, of at least one (e.g., at least 1, 2, 3, 4, 5, 6, 7, 8, 9, 10, 11, 12, 13, 14, 15, or 16) of MCP-3, HAOX1, CA5A, CALCA, IL8, SULT2A1, VAMP5, SPINK1, ENPP7, ACE2, CTSL1, PRSS2, CXCL10, MFGE8, KRT19, or ALDH1A1, and/or an increased concentration, as compared to a control, of at least one (e.g., at least 1, 2, or 3) of PON3, LEP, or MBL2 is predictive that the subject will respond to the therapy comprising the JAK inhibitor.

In some embodiments, the method includes: measuring the concentration of at least one protein (e.g., at least 1, 2, 3, 4, 5, 6, 7, 8, 9, or 10 proteins) selected from the group consisting of PON3, LEP, MCP-3, HAOX1, CA5A, CALCA, IL8, SULT2A1, VAMP5, and SPINK1 in the biological sample, wherein a reduced concentration, as compared to a control, of at least one (e.g., at least 1, 2, 3, 4, 5, 6, 7, or 8) of MCP-3, HAOX1, CA5A, CALCA, IL8, SULT2A1, VAMP5, or SPINK1, and/or an increased concentration, as compared to a control, of at least one (e.g., at least 1 or 2) of PON3 or LEP is predictive that the subject will respond to the therapy comprising the JAK inhibitor.

In some embodiments of the methods described herein, the control is a pre-established cut-off value.

In some embodiments of the methods described herein, the control is the concentration of the protein in a sample or samples obtained from one or more subjects that have not responded to treatment with the JAK inhibitor.

The disclosure also features a method for measuring the amount of a protein in a sample, by: providing a biological sample obtained from a human subject having, suspected of having, or at risk of developing GvHD; and measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of PON3, CNTN1, IGFBP3, LEP, Notch 3, TN-R, HSD11B1, FAM19A5, NCAN, F11, GDF-8, CCL28, GALNT10, BCAN, TIMP4, CRISP2, CD207, WNT9A, MBL2, EN-RAGE, TWEAK, CR2, MFAP5, KIT, GH, PFKM, CDSN, CRH, GCP5, KLK6, DRAXIN, IL8, HAOX1, ENPP7, ACE2, SULT2A1, MCP-3, CES1, MFGE8, PLXNB1, TNFRSF10A, CCL15, SEMA4C, PREB, NFATC3, CCL19, DLL1, ENTPD2, IL-4RA, EPHA2, FOSB, CXCL10, VAMP5, ALDH3A1, MVK, IL12RB1, CALCA, AHCY, PRSS2, LILRB4, DDAH1, IL-1ra, NECTIN2, PDCD1, CD74, PD-L1, REG3A, CA5A, N2DL-2, CDCP1, U-PAR, SIGLEC7, ANGPTL4, ALDH1A1, SPINK1, HTRA2, PRDX6, IL-1RT2, IGFBP-1, HNMT, TRAIL-R2, CXADR, CTSL1, IFN-gamma-R1, IL-18R1, KRT19, KYNU, and TGM2 in the biological sample.

In some embodiments, the method includes measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of PON3, LEP, MBL2, GH, GDF-8, EN-RAGE, CRISP2, CR2, MCP-3, HAOX1, CA5A, CALCA, IL8, SULT2A1, VAMP5, SPINK1, ENPP7, ACE2, CTSL1, PRSS2, CXCL10, MFGE8, KRT19, ALDH1A1, CES1, REG3A, KYNU, IL-4RA, CDCP1, MVK, FOSB, NFATC3, N2DL-2, DDAH1, IGFBP-1, ALDH3A1, CXADR, PLXNB1, CD74, ENTPD2, PREB, CCL19, HNMT, HTRA2, IL-1RT2, and IL-18R1 in the biological sample.

In some embodiments, the method includes measuring the concentration of at least one protein (e.g., at least 1, 2, 3, 4, 5, 6, 7, 8, 9, 10, 11, 12, 13, 14, 15, 16, 17, 18, or 19 proteins) selected from the group consisting of PON3, LEP, MBL2, MCP-3, HAOX1, CA5A, CALCA, IL8, SULT2A1, VAMP5, SPINK1, ENPP7, ACE2, CTSL1, PRSS2, CXCL10, MFGE8, KRT19, and ALDH1A1 in the biological sample.

In some embodiments, the method includes measuring the concentration of at least one protein (e.g., at least 1, 2, 3, 4, 5, 6, 7, 8, 9, or 10 proteins) selected from the group consisting of PON3, LEP, MCP-3, HAOX1, CA5A, CALCA, IL8, SULT2A1, VAMP5, and SPINK1 in the biological sample.

In some embodiments of the methods described herein, the concentrations of no more than 50, 40, 30, 20, 15, 10, or 5 proteins are measured.

The disclosure also features a method of treating a human subject having, suspected of having, or at risk of developing GvHD, by: measuring, in a first biological sample obtained from the human subject prior to administering a therapy comprising a JAK inhibitor, the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFK-BIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, HAVCR2, CD84, STX8, LY9, ZBTB16, CD200R1, TOP2B, THY 1, PRKRA, ITGB1BP2, CD48, CD244, HCLS1, MPO, SIT1, ICAM3, SOST, DDX58, TNF-R2, TRAF2, SMAD1, LAIR-2, PIK3AP1, VSIG4, SIGLEC10, CD6, SKAP1, FCRL5, CD177, KLRD1, ERBB2IP, MILR1, MIF, SNAP23, NUB1, TIGAR, STAMPB, DSC2, LAIR1, FKBP1B, RASSF2, FATC1, CBL, IgG Fc receptor II-b, GLO1, PVALB, SCAMP3, SLAMF8, STX16, TNF-R1, DFFA, PPP1R2, ANG-1, CCL5, MAP2K6, CRKL, CD38, CXCL5, PILRA, IRAK1, CA13, STX6, PRTN3, IL-5R-alpha, ESM-1, EGLN1, CLEC1B, TYMP, SNAP29, PDGF subunit A, TNFRSF11A, gal-8, GCNT1, STK4, TNC, THBS4, CLEC4D, SIGLEC6, WASF1, WAS, COMT, RETN, SH2D1A, RNASE3, PAR-1, CD69, SIGLEC1, FR-gamma, ADAM 8, AZU1, AREG, SDC4, DCTN2, BID, RELT, CLEC5A, APEX1, PSP-D, FGR, SELE, SELL, MESDC2, IQGAP2, CRTAM, LILRB2, TANK, CPXM1, ARSB, SLAMF1, PEBP1, STIP1, PDGF subunit B, SCARF1, DEFA1, EPHB4, ARHGAP1, CLM-1, DAB2, LYN, CASP-8, APBB1IP, ANXA11, ICAM1, PRKCQ, VCAM1, HDGF, CD2AP, TNFRSF6B, CLEC1A, TNFRSF14, TACC3, MMP-1, NRP1, ZBTB17, NADK, PLXNA4, MMP-9, NCR1, AMIGO2, FES, CD79B, TNXB, TXNDC5, TRANCE, ARG1, PCDH17, LRMP, C1QTNF1, CLM-6, CKAP4, APP, PGLYRP1, LILRA5, CLEC10A, NMNAT1, IL-6RA, ATG4A, TIMP1, COCH, DKN1A, CD1C, DECR1, DAG1, IGFBP-2, RET, GSAP, PILRB, CLEC6A, PECAM-1, PXN, ADGRG1, DPP7, TDRKH, Siglec-9, CD40-L, VEGFC, LYVE1, FADD, FCRL1, EGF, HGF, GZMH, CLEC4G, LY75, PRDX3, COL4A1, CEACAM8, SEMA7A, NUDT5, FCRL6, PAPPA, FASLG, GRN, MATN3, TMPRSS15, CCL11, FAM3B, MMP7, NCAM1, Gal-3, CCL25, THPO, hK14, KIM1, Flt3L, PLIN1, SPON2, Gal-4, FABP4, DNER, GAL, CPM, VWC2, PPY, PAM, PVR, SERPINA5, ST3GAL1, CST5, CES2, CNDP1, CX3CL1, HO-1, PRELP, ADM, VSIG2, FABP2, CEACAM5, SLITRK2, MCP-1, NTRK3, CLUL1, CXCL16, SCF, TMPRSS5, REG4, hK11, SCGB3A1, DKKL1, NEP, CPA2, Ep-CAM, THBS2, GPNMB, ITGB5, GT, APLP1, TACSTD2, NINJ1, REN, GCG, SERPINA9, KAZALD1, SERPINA12, PODXL, AMN, IGF1R, LTBP2, ANGPTL3, SCARA5, B4GAT1, ROBO2, PDGFC, CA12, DDC, EDIL3, XPNPEP2, PRTG, NQO2, AMBP, ERBB2, IL6, MCP-1, VEGFD, GDF-2, MUC-16, KLK10, FAM3C, uPA, AGR2, METRNL, RTN4R, IGF2R, NTRK2, ITGB6, SCARF2, SCGB3A2, RGMB, EZR, PROC, FURIN, PIgR, and SMOC2; administering the therapy comprising the JAK inhibitor to the human subject; and measuring, in a second biological sample obtained from the human subject after administering the therapy comprising the JAK inhibitor, a reduced concentration, as compared to the first biological sample, of at least one protein (e.g., at least 1, 2, 3, 4, 5, 6, 7, 8, 9, 10, 11, 12, 13, 14, 15, 16, 17, 18, 19, or 20 proteins) selected from the group consisting of INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, HAVCR2, CD84, STX8, LY9, ZBTB16, CD200R1, TOP2B, THY 1, PRKRA, ITGB1BP2, CD48, CD244, HCLS1, MPO, SIT1, ICAM3, SOST, DDX58, TNF-R2, TRAF2, SMAD1, LAIR-2, PIK3AP1, VSIG4, SIGLEC10, CD6, SKAP1, FCRL5, CD177, KLRD1, ERBB2IP, MILR1, MIF, SNAP23, NUB1, TIGAR, STAMPB, DSC2, LAIR1, FKBP1B, RASSF2, FATC1, CBL, IgG Fc receptor II-b, GLO1, PVALB, SCAMP3, SLAMF8, STX16, TNF-R1, DFFA, PPP1R2, ANG-1, CCL5, MAP2K6, CRKL, CD38, CXCL5, PILRA, IRAK1, CA13, STX6, PRTN3, IL-5R-alpha, ESM-1, EGLN1, CLEC1B, TYMP, SNAP29, PDGF subunit A, TNFRSF11A, gal-8, GCNT1, STK4, TNC, THBS4, CLEC4D, SIGLEC6, WASF1, WAS, COMT, RETN, SH2D1A, RNASE3, PAR-1, CD69, SIGLEC1, FR-gamma, ADAM 8, AZU1, AREG, SDC4, DCTN2, BID, RELT, CLEC5A, APEX1, PSP-D, FGR, SELE, SELL, MESDC2, IQGAP2, CRTAM, LILRB2, TANK, CPXM1, ARSB, SLAMF1, PEBP1, STIP1, PDGF subunit B, SCARF1, DEFA1, EPHB4, ARHGAP1, CLM-1, DAB2, LYN, CASP-8, APBB1IP, ANXA11, ICAM1, PRKCQ, VCAM1, HDGF, CD2AP, TNFRSF6B, CLEC1A, TNFRSF14, TACC3, MMP-1, NRP1, ZBTB17, NADK, PLXNA4, MMP-9, NCR1, AMIGO2, FES, CD79B, TNXB, TXNDC5, TRANCE, ARG1, PCDH17, LRMP, C1QTNF1, CLM-6, CKAP4, APP, PGLYRP1, LILRA5, CLEC10A, NMNAT1, IL-6RA, ATG4A, TIMP1, COCH, DKN1A, CD1C, DECR1, DAG1, IGFBP-2, RET, GSAP, PILRB, CLEC6A, PECAM-1, PXN, ADGRG1, DPP7, TDRKH, Siglec-9, CD40-L, VEGFC, LYVE1, FADD, FCRL1, EGF, HGF, GZMH, CLEC4G, LY75, PRDX3, COL4A1, CEACAM8, SEMA7A, NUDT5, FCRL6, PAPPA, FASLG, GRN, and MATN3, and/or an increased concentration, as compared to the first biological sample, of at least one protein (e.g., at least 1, 2, 3, 4, 5, 6, 7, 8, 9, 10, 11, 12, 13, 14, 15, 16, 17, 18, 19, or 20 proteins) selected from the group consisting of TMPRSS15, CCL11, FAM3B, MMP7, NCAM1, Gal-3, CCL25, THPO, hK14, KIM1, Flt3L, PLIN1, SPON2, Gal-4, FABP4, DNER, GAL, CPM, VWC2, PPY, PAM, PVR, SERPINA5, ST3GAL1, CST5, CES2, CNDP1, CX3CL1, HO-1, PRELP, ADM, VSIG2, FABP2, CEACAM5, SLITRK2, MCP-1, NTRK3, CLUL1, CXCL16, SCF, TMPRSS5, REG4, hK11, SCGB3A1, DKKL1, NEP, CPA2, Ep-CAM, THBS2, GPNMB, ITGB5, GT, APLP1, TACSTD2, NINE, REN, GCG, SERPINA9, KAZALD1, SERPINA12, PODXL, AMN, IGF1R, LTBP2, ANGPTL3, SCARA5, B4GAT1, ROBO2, PDGFC, CA12, DDC, EDIL3, XPNPEP2, PRTG, NQO2, AMBP, ERBB2, IL6, MCP-1, VEGFD, GDF-2, MUC-16, KLK10, FAM3C, uPA, AGR2, METRNL, RTN4R, IGF2R, NTRK2, ITGB6, SCARF2, SCGB3A2, RGMB, EZR, PROC, FURIN, PIgR, and SMOC2.

In some embodiments, the method includes: measuring, in the first biological sample obtained from the human subject prior to administering the therapy comprising the JAK inhibitor, the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of TMPRSS15, CCL11, FAM3B, MMP7, NCAM1, Gal-3, CCL25, THPO, hK14, KIM1, Flt3L, PLIN1, SPON2, Gal-4, FABP4, DNER, GAL, CPM, VWC2, PPY, PAM, PVR, SERPINA5, ST3GAL1, CST5, CES2, CNDP1, CX3CL1, HO-1, PRELP, ADM, VSIG2, FABP2, CEACAM5, SLITRK2, MCP-1, NTRK3, CLUL1, CXCL16, SCF, TMPRSS5, REG4, hK11, SCGB3A1, DKKL1, NEP, CPA2, Ep-CAM, THBS2, GPNMB, INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, HAVCR2, CD84, STX8, LY9, ZBTB16, CD200R1, TOP2B, THY 1, PRKRA, ITGB1BP2, CD48, CD244, HCLS1, MPO, SIT1, ICAM3, SOST, DDX58, TNF-R2, TRAF2, SMAD1, LAIR-2, PIK3AP1, VSIG4, SIGLEC10, CD6, SKAP1, FCRL5, CD177, KLRD1, ERBB2IP, MILR1, MIF, SNAP23, NUB1, TIGAR, STAMPB, DSC2, LAIR1, FKBP1B, RASSF2, FATC1, CBL, IgG Fc receptor II-b, GLO1, PVALB, SCAMP3, SLAMF8, STX16, TNF-R1, DFFA, PPP1R2, ANG-1, CCL5, MAP2K6, CRKL, CD38, CXCL5, PILRA, IRAK1, CA13, STX6, PRTN3, IL-5R-alpha, ESM-1, EGLN1, CLEC1B, TYMP, SNAP29, PDGF subunit A, TNFRSF11A, gal-8, GCNT1, STK4, TNC, THBS4, CLEC4D, SIGLEC6, WASF1, WAS, COMT, RETN, SH2D1A, RNASE3, PAR-1, CD69, SIGLEC1, FR-gamma, ADAM 8, AZU1, AREG, SDC4, DCTN2, BID, and RELT; administering the therapy comprising the JAK inhibitor to the human subject; and measuring, in the second biological sample obtained from the human subject after administering the therapy comprising the JAK inhibitor, a reduced concentration, as compared to the first biological sample, of at least one protein (e.g., at least 1, 2, 3, 4, 5, 6, 7, 8, 9, 10, 11, 12, 13, 14, 15, 16, 17, 18, 19, or 20 proteins) selected from the group consisting of INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, HAVCR2, CD84, STX8, LY9, ZBTB16, CD200R1, TOP2B, THY 1, PRKRA, ITGB1BP2, CD48, CD244, HCLS1, MPO, SIT1, ICAM3, SOST, DDX58, TNF-R2, TRAF2, SMAD1, LAIR-2, PIK3AP1, VSIG4, SIGLEC10, CD6, SKAP1, FCRL5, CD177, KLRD1, ERBB2IP, MILR1, MIF, SNAP23, NUB1, TIGAR, STAMPB, DSC2, LAIR1, FKBP1B, RASSF2, FATC1, CBL, IgG Fc receptor II-b, GLO1, PVALB, SCAMP3, SLAMF8, STX16, TNF-R1, DFFA, PPP1R2, ANG-1, CCL5, MAP2K6, CRKL, CD38, CXCL5, PILRA, IRAK1, CA13, STX6, PRTN3, IL-5R-alpha, ESM-1, EGLN1, CLEC1B, TYMP, SNAP29, PDGF subunit A, TNFRSF11A, gal-8, GCNT1, STK4, TNC, THBS4, CLEC4D, SIGLEC6, WASF1, WAS, COMT, RETN, SH2D1A, RNASE3, PAR-1, CD69, SIGLEC1, FR-gamma, ADAM 8, AZU1, AREG, SDC4, DCTN2, BID, and RELT, and/or an increased concentration, as compared to the first biological sample, of at least one protein (e.g., at least 1, 2, 3, 4, 5, 6, 7, 8, 9, 10, 11, 12, 13, 14, 15, 16, 17, 18, 19, or 20 proteins) selected from the group consisting of TMPRSS15, CCL11, FAM3B, MMP7, NCAM1, Gal-3, CCL25, THPO, hK14, KIM1, Flt3L, PLIN1, SPON2, Gal-4, FABP4, DNER, GAL, CPM, VWC2, PPY, PAM, PVR, SERPINA5, ST3GAL1, CST5, CES2, CNDP1, CX3CL1, HO-1, PRELP, ADM, VSIG2, FABP2, CEACAM5, SLITRK2, MCP-1, NTRK3, CLUL1, CXCL16, SCF, TMPRSS5, REG4, hK11, SCGB3A1, DKKL1, NEP, CPA2, Ep-CAM, THBS2, and GPNMB.

In some embodiments, the method includes: measuring, in the first biological sample obtained from the human subject prior to administering the therapy comprising the JAK inhibitor, the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of TMPRSS15, CCL11, FAM3B, MMP7, NCAM1, Gal-3, CCL25, THPO, hK14, KIM1, INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, and HAVCR2; administering the therapy comprising the JAK inhibitor to the human subject; and measuring, in the second biological sample obtained from the human subject after administering the therapy comprising the JAK inhibitor, a reduced concentration, as compared to the first biological sample, of at least one protein (e.g., at least 1, 2, 3, 4, 5, 6, 7, 8, 9, 10, 11, 12, 13, 14, 15, 16, 17, 18, 19, or 20 proteins) selected from the group consisting of INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, and HAVCR2, and/or an increased concentration, as compared to the first biological sample, of at least one protein (e.g., at least 1, 2, 3, 4, 5, 6, 7, 8, 9, or 10 proteins) selected from the group consisting of TMPRSS15, CCL11, FAM3B, MMP7, NCAM1, Gal-3, CCL25, THPO, hK14, and KIM1.

In some embodiments, the method includes: measuring, in the first biological sample obtained from the human subject prior to administering the therapy comprising the JAK inhibitor, the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of TMPRSS15, CCL11, FAM3B, MMP7, NCAM1, Gal-3, CCL25, INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, and CNTNAP2; administering the therapy comprising the JAK inhibitor to the human subject; and measuring, in the second biological sample obtained from the human subject after administering the therapy comprising the JAK inhibitor, a reduced concentration, as compared to the first biological sample, of at least one protein (e.g., at least 1, 2, 3, 4, 5, 6, 7, 8, 9, 10, 11, 12, 13, 14, 15, 16, or 17 proteins) selected from the group consisting of INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, and CNTNAP2, and/or an increased concentration, as compared to the first biological sample, of at least one protein (e.g., at least 1, 2, 3, 4, 5, 6, or 7 proteins) selected from the group consisting of TMPRSS15, CCL11, FAM3B, MMP7, NCAM1, Gal-3, and CCL25.

In some embodiments, the method includes: measuring, in the first biological sample obtained from the human subject prior to administering the therapy comprising the JAK inhibitor, the concentration of at least one protein (e.g., at least 1, 2, 3, 4, 5, 6, 7, 8, 9, 10, 11, 12, 13, 14, 15, or 16 proteins) selected from the group consisting of TMPRSS15, CCL11, FAM3B, MMP7, NCAM1, INPPL1, LAT2, CLEC7A, PPP1R9B, NEMO, SH2B3, BCR, CD5, DNAJB1, CCL17, and ITGB2; administering the therapy comprising the JAK inhibitor to the human subject; and measuring, in the second biological sample obtained from the human subject after administering the therapy comprising the JAK inhibitor, a reduced concentration, as compared to the first biological sample, of at least one protein (e.g., at least 1, 2, 3, 4, 5, 6, 7, 8, 9, 10, or 11 proteins) selected from the group consisting of INPPL1, LAT2, CLEC7A, PPP1R9B, NEMO, SH2B3, BCR, CD5, DNAJB1, CCL17, and ITGB2, and/or an increased concentration, as compared to the first biological sample, of at least one protein (e.g., at least 1, 2, 3, 4, or 5 proteins) selected from the group consisting of TMPRSS15, CCL11, FAM3B, MMP7, and NCAM1.

The disclosure also features a method of identifying a therapeutic response of a human subject having, suspected of having, or at risk of developing GvHD to a therapy comprising a JAK inhibitor, by: providing a first biological sample obtained from the human subject before administering the therapy comprising the JAK inhibitor; measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, HAVCR2, CD84, STX8, LY9, ZBTB16, CD200R1, TOP2B, THY 1, PRKRA, ITGB1BP2, CD48, CD244, HCLS1, MPO, SIT1, ICAM3, SOST, DDX58, TNF-R2, TRAF2, SMAD1, LAIR-2, PIK3AP1, VSIG4, SIGLEC10, CD6, SKAP1, FCRL5, CD177, KLRD1, ERBB2IP, MILR1, MIF, SNAP23, NUB1, TIGAR, STAMPB, DSC2, LAIR1, FKBP1B, RASSF2, FATC1, CBL, IgG Fc receptor II-b, GLO1, PVALB, SCAMP3, SLAMF8, STX16, TNF-R1, DFFA, PPP1R2, ANG-1, CCL5, MAP2K6, CRKL, CD38, CXCL5, PILRA, IRAK1, CA13, STX6, PRTN3, IL-5R-alpha, ESM-1, EGLN1, CLEC1B, TYMP, SNAP29, PDGF subunit A, TNFRSF11A, gal-8, GCNT1, STK4, TNC, THBS4, CLEC4D, SIGLEC6, WASF1, WAS, COMT, RETN, SH2D1A, RNASE3, PAR-1, CD69, SIGLEC1, FR-gamma, ADAM 8, AZU1, AREG, SDC4, DCTN2, BID, RELT, CLEC5A, APEX1, PSP-D, FGR, SELE, SELL, MESDC2, IQGAP2, CRTAM, LILRB2, TANK, CPXM1, ARSB, SLAMF1, PEBP1, STIP1, PDGF subunit B, SCARF1, DEFA1, EPHB4, ARHGAP1, CLM-1, DAB2, LYN, CASP-8, APBB1IP, ANXA11, ICAM1, PRKCQ, VCAM1, HDGF, CD2AP, TNFRSF6B, CLEC1A, TNFRSF14, TACC3, MMP-1, NRP1, ZBTB17, NADK, PLXNA4, MMP-9, NCR1, AMIGO2, FES, CD79B, TNXB, TXNDC5, TRANCE, ARG1, PCDH17, LRMP, C1QTNF1, CLM-6, CKAP4, APP, PGLYRP1, LILRA5, CLEC10A, NMNAT1, IL-6RA, ATG4A, TIMP1, COCH, DKN1A, CD1C, DECR1, DAG1, IGFBP-2, RET, GSAP, PILRB, CLEC6A, PECAM-1, PXN, ADGRG1, DPP7, TDRKH, Siglec-9, CD40-L, VEGFC, LYVE1, FADD, FCRL1, EGF, HGF, GZMH, CLEC4G, LY75, PRDX3, COL4A1, CEACAM8, SEMA7A, NUDT5, FCRL6, PAPPA, FASLG, GRN, MATN3, TMPRSS15, CCL11, FAM3B, MMP7, NCAM1, Gal-3, CCL25, THPO, hK14, KIM1, Flt3L, PLIN1, SPON2, Gal-4, FABP4, DNER, GAL, CPM, VWC2, PPY, PAM, PVR, SERPINA5, ST3GAL1, CST5, CES2, CNDP1, CX3CL1, HO-1, PRELP, ADM, VSIG2, FABP2, CEACAM5, SLITRK2, MCP-1, NTRK3, CLUL1, CXCL16, SCF, TMPRSS5, REG4, hK11, SCGB3A1, DKKL1, NEP, CPA2, Ep-CAM, THBS2, GPNMB, ITGB5, GT, APLP1, TACSTD2, NINJ1, REN, GCG, SERPINA9, KAZALD1, SERPINA12, PODXL, AMN, IGF1R, LTBP2, ANGPTL3, SCARA5, B4GAT1, ROBO2, PDGFC, CA12, DDC, EDIL3, XPNPEP2, PRTG, NQO2, AMBP, ERBB2, IL6, MCP-1, VEGFD, GDF-2, MUC-16, KLK10, FAM3C, uPA, AGR2, METRNL, RTN4R, IGF2R, NTRK2, ITGB6, SCARF2, SCGB3A2, RGMB, EZR, PROC, FURIN, PIgR, and SMOC2 in the first biological sample; providing a second biological sample obtained from the subject after administering the therapy comprising the JAK inhibitor; and measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, HAVCR2, CD84, STX8, LY9, ZBTB16, CD200R1, TOP2B, THY 1, PRKRA, ITGB1BP2, CD48, CD244, HCLS1, MPO, SIT1, ICAM3, SOST, DDX58, TNF-R2, TRAF2, SMAD1, LAIR-2, PIK3AP1, VSIG4, SIGLEC10, CD6, SKAP1, FCRL5, CD177, KLRD1, ERBB2IP, MILR1, MIF, SNAP23, NUB1, TIGAR, STAMPB, DSC2, LAIR1, FKBP1B, RASSF2, FATC1, CBL, IgG Fc receptor II-b, GLO1, PVALB, SCAMP3, SLAMF8, STX16, TNF-R1, DFFA, PPP1R2, ANG-1, CCL5, MAP2K6, CRKL, CD38, CXCL5, PILRA, IRAK1, CA13, STX6, PRTN3, IL-5R-alpha, ESM-1, EGLN1, CLEC1B, TYMP, SNAP29, PDGF subunit A, TNFRSF11A, gal-8, GCNT1, STK4, TNC, THBS4, CLEC4D, SIGLEC6, WASF1, WAS, COMT, RETN, SH2D1A, RNASE3, PAR-1, CD69, SIGLEC1, FR-gamma, ADAM 8, AZU1, AREG, SDC4, DCTN2, BID, RELT, CLEC5A, APEX1, PSP-D, FGR, SELE, SELL, MESDC2, IQGAP2, CRTAM, LILRB2, TANK, CPXM1, ARSB, SLAMF1, PEBP1, STIP1, PDGF subunit B, SCARF1, DEFA1, EPHB4, ARHGAP1, CLM-1, DAB2, LYN, CASP-8, APBB1IP, ANXA11, ICAM1, PRKCQ, VCAM1, HDGF, CD2AP, TNFRSF6B, CLEC1A, TNFRSF14, TACC3, MMP-1, NRP1, ZBTB17, NADK, PLXNA4, MMP-9, NCR1, AMIGO2, FES, CD79B, TNXB, TXNDC5, TRANCE, ARG1, PCDH17, LRMP, C1QTNF1, CLM-6, CKAP4, APP, PGLYRP1, LILRA5, CLEC10A, NMNAT1, IL-6RA, ATG4A, TIMP1, COCH, DKN1A, CD1C, DECR1, DAG1, IGFBP-2, RET, GSAP, PILRB, CLEC6A, PECAM-1, PXN, ADGRG1, DPP7, TDRKH, Siglec-9, CD40-L, VEGFC, LYVE1, FADD, FCRL1, EGF, HGF, GZMH, CLEC4G, LY75, PRDX3, COL4A1, CEACAM8, SEMA7A, NUDT5, FCRL6, PAPPA, FASLG, GRN, MATN3, TMPRSS15, CCL11, FAM3B, MMP7, NCAM1, Gal-3, CCL25, THPO, hK14, KIM1, Flt3L, PLIN1, SPON2, Gal-4, FABP4, DNER, GAL, CPM, VWC2, PPY, PAM, PVR, SERPINA5, ST3GAL1, CST5, CES2, CNDP1, CX3CL1, HO-1, PRELP, ADM, VSIG2, FABP2, CEACAM5, SLITRK2, MCP-1, NTRK3, CLUL1, CXCL16, SCF, TMPRSS5, REG4, hK11, SCGB3A1, DKKL1, NEP, CPA2, Ep-CAM, THBS2, GPNMB, ITGB5, GT, APLP1, TACSTD2, NINJ1, REN, GCG, SERPINA9, KAZALD1, SERPINA12, PODXL, AMN, IGF1R, LTBP2, ANGPTL3, SCARA5, B4GAT1, ROBO2, PDGFC, CA12, DDC, EDIL3, XPNPEP2, PRTG, NQO2, AMBP, ERBB2, IL6, MCP-1, VEGFD, GDF-2, MUC-16, KLK10, FAM3C, uPA, AGR2, METRNL, RTN4R, IGF2R, NTRK2, ITGB6, SCARF2, SCGB3A2, RGMB, EZR, PROC, FURIN, PIgR, and SMOC2 in the second biological sample, wherein a reduced concentration in the second biological sample, as compared to the first biological sample, of at least one (e.g., at least 1, 2, 3, 4, 5, 6, 7, 8, 9, 10, 11, 12, 13, 14, 15, 16, 17, 18, 19, or 20) of INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, HAVCR2, CD84, STX8, LY9, ZBTB16, CD200R1, TOP2B, THY 1, PRKRA, ITGB1BP2, CD48, CD244, HCLS1, MPO, SIT1, ICAM3, SOST, DDX58, TNF-R2, TRAF2, SMAD1, LAIR-2, PIK3AP1, VSIG4, SIGLEC10, CD6, SKAP1, FCRL5, CD177, KLRD1, ERBB2IP, MILR1, MIF, SNAP23, NUB1, TIGAR, STAMPB, DSC2, LAIR1, FKBP1B, RASSF2, FATC1, CBL, IgG Fc receptor II-b, GLO1, PVALB, SCAMP3, SLAMF8, STX16, TNF-R1, DFFA, PPP1R2, ANG-1, CCL5, MAP2K6, CRKL, CD38, CXCL5, PILRA, IRAK1, CA13, STX6, PRTN3, IL-5R-alpha, ESM-1, EGLN1, CLEC1B, TYMP, SNAP29, PDGF subunit A, TNFRSF11A, gal-8, GCNT1, STK4, TNC, THBS4, CLEC4D, SIGLEC6, WASF1, WAS, COMT, RETN, SH2D1A, RNASE3, PAR-1, CD69, SIGLEC1, FR-gamma, ADAM 8, AZU1, AREG, SDC4, DCTN2, BID, RELT, CLEC5A, APEX1, PSP-D, FGR, SELE, SELL, MESDC2, IQGAP2, CRTAM, LILRB2, TANK, CPXM1, ARSB, SLAMF1, PEBP1, STIP1, PDGF subunit B, SCARF1, DEFA1, EPHB4, ARHGAP1, CLM-1, DAB2, LYN, CASP-8, APBB1IP, ANXA11, ICAM1, PRKCQ, VCAM1, HDGF, CD2AP, TNFRSF6B, CLEC1A, TNFRSF14, TACC3, MMP-1, NRP1, ZBTB17, NADK, PLXNA4, MMP-9, NCR1, AMIGO2, FES, CD79B, TNXB, TXNDC5, TRANCE, ARG1, PCDH17, LRMP, C1QTNF1, CLM-6, CKAP4, APP, PGLYRP1, LILRA5, CLEC10A, NMNAT1, IL-6RA, ATG4A, TIMP1, COCH, DKN1A, CD1C, DECR1, DAG1, IGFBP-2, RET, GSAP, PILRB, CLEC6A, PECAM-1, PXN, ADGRG1, DPP7, TDRKH, Siglec-9, CD40-L, VEGFC, LYVE1, FADD, FCRL1, EGF, HGF, GZMH, CLEC4G, LY75, PRDX3, COL4A1, CEACAM5, SEMA7A, NUDT5, FCRL6, PAPPA, FASLG, GRN, and/or MATN3, and/or an increased concentration in the second biological sample, as compared to the first biological sample, of at least one (e.g., at least 1, 2, 3, 4, 5, 6, 7, 8, 9, 10, 11, 12, 13, 14, 15, 16, 17, 18, 19, or 20) of TMPRSS15, CCL11, FAM3B, MMP7, NCAM1, Gal-3, CCL25, THPO, hK14, KIM1, Flt3L, PLIN1, SPON2, Gal-4, FABP4, DNER, GAL, CPM, VWC2, PPY, PAM, PVR, SERPINA5, ST3GAL1, CST5, CES2, CNDP1, CX3CL1, HO-1, PRELP, ADM, VSIG2, FABP2, CEACAM5, SLITRK2, MCP-1, NTRK3, CLUL1, CXCL16, SCF, TMPRSS5, REG4, hK11, SCGB3A1, DKKL1, NEP, CPA2, Ep-CAM, THBS2, GPNMB, ITGB5, GT, APLP1, TACSTD2, NINJ1, REN, GCG, SERPINA9, KAZALD1, SERPINA12, PODXL, AMN, IGF1R, LTBP2, ANGPTL3, SCARA5, B4GAT1, ROBO2, PDGFC, CA12, DDC, EDIL3, XPNPEP2, PRTG, NQO2, AMBP, ERBB2, IL6, MCP-1, VEGFD, GDF-2, MUC-16, KLK10, FAM3C, uPA, AGR2, METRNL, RTN4R, IGF2R, NTRK2, ITGB6, SCARF2, SCGB3A2, RGMB, EZR, PROC, FURIN, PIgR, and/or SMOC2 indicates that the human subject has undergone a therapeutic response to the therapy comprising the JAK inhibitor.

In some embodiments, the method includes: measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of TMPRSS15, CCL11, FAM3B, MMP7, NCAM1, Gal-3, CCL25, THPO, hK14, KIM1, Flt3L, PLIN1, SPON2, Gal-4, FABP4, DNER, GAL, CPM, VWC2, PPY, PAM, PVR, SERPINA5, ST3GAL1, CST5, CES2, CNDP1, CX3CL1, HO-1, PRELP, ADM, VSIG2, FABP2, CEACAM5, SLITRK2, MCP-1, NTRK3, CLUL1, CXCL16, SCF, TMPRSS5, REG4, hK11, SCGB3A1, DKKL1, NEP, CPA2, Ep-CAM, THBS2, GPNMB, INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, HAVCR2, CD84, STX8, LY9, ZBTB16, CD200R1, TOP2B, THY 1, PRKRA, ITGB1BP2, CD48, CD244, HCLS1, MPO, SIT1, ICAM3, SOST, DDX58, TNF-R2, TRAF2, SMAD1, LAIR-2, PIK3AP1, VSIG4, SIGLEC10, CD6, SKAP1, FCRL5, CD177, KLRD1, ERBB2IP, MILR1, MIF, SNAP23, NUB1, TIGAR, STAMPB, DSC2, LAIR1, FKBP1B, RASSF2, FATC1, CBL, IgG Fc receptor II-b, GLO1, PVALB, SCAMP3, SLAMF8, STX16, TNF-R1, DFFA, PPP1R2, ANG-1, CCL5, MAP2K6, CRKL, CD38, CXCL5, PILRA, IRAK1, CA13, STX6, PRTN3, IL-5R-alpha, ESM-1, EGLN1, CLEC1B, TYMP, SNAP29, PDGF subunit A, TNFRSF11A, gal-8, GCNT1, STK4, TNC, THBS4, CLEC4D, SIGLEC6, WASF1, WAS, COMT, RETN, SH2D1A, RNASE3, PAR-1, CD69, SIGLEC1, FR-gamma, ADAM 8, AZU1, AREG, SDC4, DCTN2, BID, and RELT in the first biological sample; and measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of TMPRSS15, CCL11, FAM3B, MMP7, NCAM1, Gal-3, CCL25, THPO, hK14, KIM1, Flt3L, PLIN1, SPON2, Gal-4, FABP4, DNER, GAL, CPM, VWC2, PPY, PAM, PVR, SERPINA5, ST3GAL1, CST5, CES2, CNDP1, CX3CL1, HO-1, PRELP, ADM, VSIG2, FABP2, CEACAM5, SLITRK2, MCP-1, NTRK3, CLUL1, CXCL16, SCF, TMPRSS5, REG4, hK11, SCGB3A1, DKKL1, NEP, CPA2, Ep-CAM, THBS2, GPNMB, INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, HAVCR2, CD84, STX8, LY9, ZBTB16, CD200R1, TOP2B, THY 1, PRKRA, ITGB1BP2, CD48, CD244, HCLS1, MPO, SIT1, ICAM3, SOST, DDX58, TNF-R2, TRAF2, SMAD1, LAIR-2, PIK3AP1, VSIG4, SIGLEC10, CD6, SKAP1, FCRL5, CD177, KLRD1, ERBB2IP, MILR1, MIF, SNAP23, NUB1, TIGAR, STAMPB, DSC2, LAIR1, FKBP1B, RASSF2, FATC1, CBL, IgG Fc receptor II-b, GLO1, PVALB, SCAMP3, SLAMF8, STX16, TNF-R1, DFFA, PPP1R2, ANG-1, CCL5, MAP2K6, CRKL, CD38, CXCL5, PILRA, IRAK1, CA13, STX6, PRTN3, IL-5R-alpha, ESM-1, EGLN1, CLEC1B, TYMP, SNAP29, PDGF subunit A, TNFRSF11A, gal-8, GCNT1, STK4, TNC, THBS4, CLEC4D, SIGLEC6, WASF1, WAS, COMT, RETN, SH2D1A, RNASE3, PAR-1, CD69, SIGLEC1, FR-gamma, ADAM 8, AZU1, AREG, SDC4, DCTN2, BID, and RELT, wherein a reduced concentration in the second biological sample, as compared to the first biological sample, of at least one (e.g., at least 1, 2, 3, 4, 5, 6, 7, 8, 9, 10, 11, 12, 13, 14, 15, 16, 17, 18, 19, or 20) of INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, HAVCR2, CD84, STX8, LY9, ZBTB16, CD200R1, TOP2B, THY 1, PRKRA, ITGB1BP2, CD48, CD244, HCLS1, MPO, SIT1, ICAM3, SOST, DDX58, TNF-R2, TRAF2, SMAD1, LAIR-2, PIK3AP1, VSIG4, SIGLEC10, CD6, SKAP1, FCRL5, CD177, KLRD1, ERBB2IP, MILR1, MIF, SNAP23, NUB1, TIGAR, STAMPB, DSC2, LAIR1, FKBP1B, RASSF2, FATC1, CBL, IgG Fc receptor II-b, GLO1, PVALB, SCAMP3, SLAMF8, STX16, TNF-R1, DFFA, PPP1R2, ANG-1, CCL5, MAP2K6, CRKL, CD38, CXCL5, PILRA, IRAK1, CA13, STX6, PRTN3, IL-5R-alpha, ESM-1, EGLN1, CLEC1B, TYMP, SNAP29, PDGF subunit A, TNFRSF11A, gal-8, GCNT1, STK4, TNC, THBS4, CLEC4D, SIGLEC6, WASF1, WAS, COMT, RETN, SH2D1A, RNASE3, PAR-1, CD69, SIGLEC1, FR-gamma, ADAM 8, AZU1, AREG, SDC4, DCTN2, BID, and RELT, and/or an increased concentration in the second biological sample, as compared to the first biological sample, of at least one (e.g., at least 1, 2, 3, 4, 5, 6, 7, 8, 9, 10, 11, 12, 13, 14, 15, 16, 17, 18, 19, or 20) of TMPRSS15, CCL11, FAM3B, MMP7, NCAM1, Gal-3, CCL25, THPO, hK14, KIM1, Flt3L, PLIN1, SPON2, Gal-4, FABP4, DNER, GAL, CPM, VWC2, PPY, PAM, PVR, SERPINA5, ST3GAL1, CST5, CES2, CNDP1, CX3CL1, HO-1, PRELP, ADM, VSIG2, FABP2, CEACAM5, SLITRK2, MCP-1, NTRK3, CLUL1, CXCL16, SCF, TMPRSS5, REG4, hK11, SCGB3A1, DKKL1, NEP, CPA2, Ep-CAM, THBS2, and GPNMB indicates that the human subject has undergone a therapeutic response to the therapy comprising the JAK inhibitor.

In some embodiments, the method includes: measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of TMPRSS15, CCL11, FAM3B, MMP7, NCAM1, Gal-3, CCL25, THPO, hK14, KIM1, INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, and HAVCR2 in the first biological sample; and measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of TMPRSS15, CCL11, FAM3B, MMP7, NCAM1, Gal-3, CCL25, THPO, hK14, KIM1, INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFK-BIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, and HAVCR2 in the second biological sample, wherein a reduced concentration in the second biological sample, as compared to the first biological sample, of at least one (e.g., at least 1, 2, 3, 4, 5, 6, 7, 8, 9, 10, 11, 12, 13, 14, 15, 16, 17, 18, 19, or 20) of INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOSCAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, and HAVCR2, and/or an increased concentration in the second biological sample, as compared to the first biological sample, of at least one (e.g., at least 1, 2, 3, 4, 5, 6, 7, 8, 9, or 10) of TMPRSS15, CCL11, FAM3B, MMP7, NCAM1, Gal-3, CCL25, THPO, hK14, and KIM1 indicates that the human subject has undergone a therapeutic response to the therapy comprising the JAK inhibitor.

In some embodiments, the method includes: measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of TMPRSS15, CCL11, FAM3B, MMP7, NCAM1, Gal-3, CCL25, INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, and CNTNAP2 in the first biological sample; and measuring the concentration of at least one protein (e.g., at least 1, 2, 3, 4, 5, 6, 7, 8, 9, 10, 11, 12, 13, 14, 15, 16, 17, 18, 19, or 20 proteins) selected from the group consisting of TMPRSS15, CCL11, FAM3B, MMP7, NCAM1, Gal-3, CCL25, INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, and CNTNAP2 in the second biological sample, wherein a reduced concentration in the second biological sample, as compared to the first biological sample, of at least one (e.g., at least 1, 2, 3, 4, 5, 6, 7, 8, 9, 10, 11, 12, 13, 14, 15, 16, or 17) of INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, and CNTNAP2, and/or an increased concentration in the second biological sample, as compared to the first biological sample, of at least one (e.g., at least 1, 2, 3, 4, 5, 6, or 7) of TMPRSS15, CCL11, FAM3B, MMP7, NCAM1, Gal-3, and CCL25 indicates that the human subject has undergone a therapeutic response to the therapy comprising the JAK inhibitor.

In some embodiments, the method includes: measuring the concentration of at least one protein (e.g., at least 1, 2, 3, 4, 5, 6, 7, 8, 9, 10, 11, 12, 13, 14, 15, or 16 proteins) selected from the group consisting of TMPRSS15, CCL11, FAM3B, MMP7, NCAM1, INPPL1, LAT2, CLEC7A, PPP1R9B, NEMO, SH2B3, BCR, CD5, DNAJB1, CCL17, and ITGB2 in the first biological sample; and measuring the concentration of at least one protein (e.g., at least 1, 2, 3, 4, 5, 6, 7, 8, 9, 10, 11, 12, 13, 14, 15, or 16 proteins) selected from the group consisting of TMPRSS15, CCL11, FAM3B, MMP7, NCAM1, INPPL1, LAT2, CLEC7A, PPP1R9B, NEMO, SH2B3, BCR, CD5, DNAJB1, CCL17, and ITGB2 in the second biological sample, wherein a reduced concentration in the second biological sample, as compared to the first biological sample, of at least one (e.g., at least 1, 2, 3, 4, 5, 6, 7, 8, 9, 10, or 11) of INPPL1, LAT2, CLEC7A, PPP1R9B, NEMO, SH2B3, BCR, CD5, DNAJB1, CCL17, and ITGB2, and/or an increased concentration in the second biological sample, as compared to the first biological sample, of at least one (e.g., at least 1, 2, 3, 4, or 5) of TMPRSS15, CCL11, FAM3B, MMP7, and NCAM1 indicates that the human subject has undergone a therapeutic response to the therapy comprising the JAK inhibitor.

The disclosure also features a method of treating a human subject having, suspected of having, or at risk of developing GvHD, by administering to the human subject a therapy comprising a JAK inhibitor, wherein the human subject has been previously determined to have (i) a baseline concentration of at least one protein selected from the group consisting of MCP-3, CA5A, IL8, CXCL10, IL6, CCL19, CTSL1, ACE2, ALDH1A1, TNFRSF6B, KYNU, FOSB, ALDH3A1, and DDAH1 in a biological sample obtained from the human subject that is lower than a control, and/or (ii) a baseline concentration of at least one protein selected from the group consisting of PON3, SCF, GH, SRC, and CR2 in a biological sample obtained from the human subject that is higher than a control.

The disclosure also features a method of treating a human subject having, suspected of having, or at risk of developing GvHD by: providing a biological sample obtained from the human subject; measuring in the biological sample a reduced concentration, as compared to a control, of at least one protein selected from the group consisting of MCP-3, CA5A, IL8, CXCL10, IL6, CCL19, CTSL1, ACE2, ALDH1A1, TNFRSF6B, KYNU, FOSB, ALDH3A1, and DDAH1, and/or an increased concentration, as compared to a control, of at least one protein selected from the group consisting of PON3, SCF, GH, SRC, and CR2; and administering a therapy comprising a JAK inhibitor to the human subject.

The disclosure also features a method of predicting the response of a human subject having, suspected of having, or at risk of developing GvHD to a therapy comprising a JAK inhibitor by: providing a biological sample obtained from the subject before the therapy comprising the JAK inhibitor; and measuring the concentration of at least one protein selected from the group consisting of PON3, SCF, GH, SRC, CR2, MCP-3, CA5A, IL8, CXCL10, IL6, CCL19, CTSL1, ACE2, ALDH1A1, TNFRSF6B, KYNU, FOSB, ALDH3A1, and DDAH1 in the biological sample, wherein a reduced concentration, as compared to a control, of MCP-3, CA5A, IL8, CXCL10, IL6, CCL19, CTSL1, ACE2, ALDH1A1, TNFRSF6B, KYNU, FOSB, ALDH3A1, and/or DDAH1, and/or an increased concentration, as compared to a control, of PON3, SCF, GH, SRC, and/or CR2 is predictive that the subject will respond to the therapy comprising the JAK inhibitor.

In some embodiments of the methods described herein, the control is a pre-established cut-off value.

In some embodiments of the methods described herein, the control is the concentration of the protein in a sample or samples obtained from one or more subjects that have not responded to treatment with the JAK inhibitor.

The disclosure also features a method for measuring the amount of a protein in a sample by: providing a biological sample obtained from a human subject having, suspected of having, or at risk of developing GvHD; and measuring the concentration of at least one protein selected from the group consisting of PON3, SCF, GH, SRC, CR2, MCP-3, CA5A, IL8, CXCL10, IL6, CCL19, CTSL1, ACE2, ALDH1A1, TNFRSF6B, KYNU, FOSB, ALDH3A1, and DDAH1 in the biological sample.

In some embodiments of any of the methods described herein, the concentrations of no more than 20 proteins are measured.

In some embodiments of any of the methods described herein, the concentrations of no more than 10 proteins are measured.

In some embodiments of any of the methods described herein, the biological sample is blood, serum, plasma, urine, spinal fluid, saliva, lacrimal fluid, or sweat. In some embodiments, the biological sample is blood, serum, or plasma.

In some embodiments of any of the methods described herein, the concentration of the protein is measured by an immunological method. The immunological method can be, for example, an enzyme-linked immunosorbent assay, enzyme immunoassay, radioimmunoassay, chemiluminescent immunoassay, electrochemiluminescence immunoassay, latex turbidimetric immunoassay, latex photometric immunoassay, immuno-chromatographic assay, or western blotting.

In some embodiments of any of the methods described herein, the concentration of the protein is measured by mass spectrometry.

In some embodiments of any of the methods described herein, the JAK inhibitor is itacitinib.

In some embodiments of any of the methods described herein, the JAK inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide or a pharmaceutically acceptable salt thereof or ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile or a pharmaceutically acceptable salt thereof.

In some embodiments of any of the methods described herein, a second therapeutic agent is administered to the human subject in combination with the JAK inhibitor. The second therapeutic agent can be, for example, a corticosteroid (e.g., methylprednisolone or prednisone), methotrexate, cyclosporine, mycophenolate mofetil, tacrolimus, sirolimus, everolimus, antithymocyte globulin, alemtuzumab, cyclophosphamide, ibrutinib, imatinib, infliximab, etanercept, tocilizumab, alemtuzumab, basiliximab, daclizumab, rituximab, denileukin diftitox, pentostatin, ciclosporin, thalidomide, halofuginone, hydroxychloroquine, or mesenchymal stem cells. The JAK inhibitor and the second therapeutic agent can be administered simultaneously or sequentially.

In some embodiments of any of the methods described herein, the GvHD is acute GvHD.

In some embodiments of any of the methods described herein, the GvHD is chronic GvHD.

The term "baseline concentration" of protein refers to the concentration of a protein in a subject prior to initiation of treatment with a JAK inhibitor.

The term "reduced concentration" means a concentration of the protein being analyzed that is lower than the concentration of that protein in a control or in a previous sample. For example, the concentration of the protein being analyzed can be at least 1.5, 2, 3, 4, 5, 6, 7, 8, 9, 10, 20, 25, 50, 75, or 100 times lower, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% lower, than the concentration of that protein in a control.

The term "increased concentration" means a concentration of the protein being analyzed that is higher than the concentration of that protein in a control or in a previous sample. For example, the concentration of the protein being analyzed can be at least 1.5, 2, 3, 4, 5, 6, 7, 8, 9, 10, 20, 25, 50, 75, or 100 times higher, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% higher, than the concentration of that protein in a control.

The term "respond to a therapy" means that the subject administered with the therapy shows a positive response to the JAK inhibitor therapy provided.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DETAILED DESCRIPTION

This disclosure provides methods and compositions for treating a subject having, suspected of having, or at risk of developing GvHD with a JAK inhibitor. The disclosure provides predictive biomarkers (e.g., protein expression levels) to identify those subjects having, suspected of having, or at risk of developing GvHD for whom administering a therapy comprising a JAK inhibitor is likely to be effective.

Graft Versus Host Disease

GvHD occurs when donor T cells respond to genetically defined proteins (including but not limited to Human Leukocyte Antigens) on host cells. Acute GvHD is generally defined to occur prior to day 100 post-transplant, whereas chronic GvHD occurs after that time.

The clinical manifestations of acute GvHD occur in the skin, gastrointestinal tract, and liver. Skin is the most commonly affected organ in acute GvHD and is usually the first organ involved, often coinciding with engraftment of donor cells. The characteristic maculopapular rash is pruritic and can spread throughout the body. In severe cases, the skin may blister and ulcerate. Other features include dyskeratosis, exocytosis of lymphocytes, satellite lymphocytes adjacent to dyskeratotic epidermal keratinocytes, and a perivascular lymphocytic infiltration in the dermis. Gastrointestinal tract involvement of acute GvHD usually presents as diarrhea but may also include vomiting, anorexia, and/or abdominal pain. The histologic features of liver disease caused by GvHD are endothelialitis, lymphocytic infiltration of the portal areas, pericholangitis, and bile duct destruction.

Chronic GvHD is the major cause of late non-relapse death following hematopoietic cell transplant. Its presentation may be progressive (e.g., acute GvHD merging into chronic GvHD), quiescent (acute GvHD that resolves completely but is later followed by chronic GvHD), or it may occur de novo. Older recipient age and a history of acute GvHD are the greatest risk factors for chronic GvHD. Clinical signs of chronic GvHD often first appear in the buccal mucosa.

Methods of Predicting Responsiveness to a Therapy Comprising a JAK Inhibitor Several proteins have been identified in the Examples whose expression levels are useful in predicting responsiveness (e.g., improvement in disease scores and/or disease resolution) of a subject having GvHD to a therapy comprising a JAK inhibitor. These proteins are listed in Tables 1 and 2.

TABLE 1

Biomarkers Exhibiting Reduced Expression in GvHD Subjects that Respond to Treatment with a JAK inhibitor as Compared to Control Subjects that do not Respond

| Protein |
|---|
| IL8 |
| HAOX1 |
| ENPP7 |
| ACE2 |
| SULT2A1 |
| MCP-3 |
| CES1 |
| MFGE8 |
| PLXNB1 |
| TNFRSF10A |
| CCL15 |
| TNFRSF10A |
| SEMA4C |
| PREB |
| NFATC3 |
| CCL19 |
| DLL1 |
| ENTPD2 |
| IL-4RA |
| EPHA2 |
| FOSB |
| CXCL10 |
| VAMP5 |
| ALDH3A1 |

TABLE 1-continued

Biomarkers Exhibiting Reduced Expression in GvHD Subjects that Respond to Treatment with a JAK inhibitor as Compared to Control Subjects that do not Respond

| Protein |
|---|
| MVK |
| IL12RB1 |
| CALCA |
| AHCY |
| PRSS2 |
| LILRB4 |
| DDAH1 |
| IL-1ra |
| NECTIN2 |
| PDCD1 |
| CD74 |
| PD-L1 |
| REG3A |
| CA5A |
| N2DL-2 |
| CDCP1 |
| U-PAR |
| SIGLEC7 |
| ANGPTL4 |
| ALDH1A1 |
| SPINK1 |
| HTRA2 |
| PRDX6 |
| IL-1RT2 |
| IGFBP-1 |
| HNMT |
| TRAIL-R2 |
| CXADR |
| CTSL1 |
| IFN-gamma-R1 |
| IL-18R1 |
| KRT19 |
| KYNU |
| TGM2 |

TABLE 2

Biomarkers Exhibiting Increased Expression in GvHD Subjects that Respond to Treatment with a JAK inhibitor as Compared to Control Subjects that do not Respond

| Protein |
|---|
| PON3 |
| CNTN1 |
| IGFBP3 |
| LEP |
| Notch 3 |
| TN-R |
| HSD11B1 |
| FAM19A5 |
| NCAN |
| F11 |
| GDF-8 |
| CCL28 |
| GALNT10 |
| BCAN |
| TIMP4 |
| CRISP2 |
| CD207 |
| WNT9A |
| MBL2 |
| EN-RAGE |
| TWEAK |
| CR2 |
| MFAP5 |
| KIT |
| GH |
| PFKM |
| CDSN |
| CRH |

TABLE 2-continued

Biomarkers Exhibiting Increased Expression in GvHD Subjects that Respond to Treatment with a JAK inhibitor as Compared to Control Subjects that do not Respond Protein

GCP5
KLK6
DRAXIN

A reduced protein concentration compared to a control of one or more (e.g., at least 1, 2, 3, 4, 5, 6, 7, 8, 9, 10, 11, 12, 13, or 14) proteins listed in Table 1 is indicative/predictive that a subject that has, is suspected of having, or is at risk of developing GvHD will respond to a therapy comprising a JAK inhibitor. For example, low concentrations (compared to a control) of CXCL10 protein in a biological sample obtained from a subject prior to treatment with the therapy comprising a JAK inhibitor are predictive that the subject will respond to the therapy comprising a JAK inhibitor.

An increased protein concentration compared to a control of one or more (e.g., at least 1, 2, 3, 4, or 5) proteins listed in Table 2 is indicative/predictive that a subject that has, is suspected of having, or is at risk of developing GvHD will respond to a therapy comprising a JAK inhibitor. For example, increased concentrations (compared to a control) of PON3 protein in a biological sample obtained from a subject prior to treatment with the therapy comprising a JAK inhibitor are predictive that the subject will respond to the therapy comprising a JAK inhibitor.

A reduced protein concentration compared to a control of one or more (e.g., at least 1, 2, 3, 4, 5, 6, 7, 8, 9, 10, 11, 12, 13, or 14) proteins listed in Table 1 combined with an increased protein concentration compared to a control of one or more (e.g., at least 1, 2, 3, 4, or 5) proteins listed in Table 2 is indicative/predictive that a subject that has, is suspected of having, or is at risk of developing GvHD will respond to a therapy comprising a JAK inhibitor. For example, low concentrations (compared to a control) of CXCL10 protein and increased concentrations (compared to a control) of PON3 protein in a biological sample obtained from a subject prior to treatment with the therapy comprising a JAK inhibitor are predictive that the subject will respond to the therapy comprising a JAK inhibitor. In another example, low concentrations (compared to a control) of MCP-3, CA5A, IL8, CXCL10, IL6, CCL19, CTSL1, ACE2, ALDH1A1, TNFRSF6B, KYNU, FOSB, ALDH3A1, and DDAH1 proteins and increased concentrations (compared to a control) of PON3, SCF, GH, SRC, and CR2 proteins in a biological sample obtained from a subject prior to treatment with the therapy comprising a JAK inhibitor are predictive that the subject will respond to the therapy comprising a JAK inhibitor.

In some embodiments, the GvHD is acute GvHD. In other embodiments, the GvHD is chronic GvHD.

Controls

As described above, the methods of the present invention can involve, measuring the concentration of one or more proteins (e.g., one or more proteins depicted in Table 1 and/or Table 2) in a biological sample from a subject having, suspected of having or at risk of developing GvHD, wherein the concentration of one or more proteins, compared to a control, predicts the response of a subject to treatment comprising a JAK inhibitor. In certain embodiments, when the concentration of a protein in Table 1 in a biological sample from a subject having, suspected of having or at risk of developing GvHD is lower than the control, the subject is identified as likely to respond to a therapy comprising a JAK inhibitor. In other embodiments, when the concentration of a protein in Table 2 in a biological sample from a subject having, suspected of having or at risk of developing GvHD is higher than the control, the subject is identified as likely to respond to a therapy comprising a JAK inhibitor. In this context, the term "control" includes a sample (from the same tissue type) obtained from a subject who is known to not respond to a therapy comprising a JAK inhibitor. The term "control" also includes a sample (from the same tissue type) obtained in the past from a subject who is known to not respond to a therapy comprising a JAK inhibitor and used as a reference for future comparisons to test samples taken from subjects for which therapeutic responsiveness is to be predicted. The "control" expression level/concentration for a particular protein in a particular cell type or tissue may be pre-established by an analysis of protein expression in one or more (e.g., 2, 3, 4, 5, 6, 7, 8, 9, 10, 15, 20, 25, 30, 35, or 40 or more) subjects, of the same species, that have not responded to treatment with a JAK inhibitor. This pre-established reference value (which may be an average or median expression level/concentration taken from multiple subjects that have not responded to the therapy) may then be used for the "control" concentration/expression level of the protein in the comparison with the test sample. In such a comparison, the subject is predicted to respond to a therapy comprising a JAK inhibitor if the expression level of the protein being analyzed is lower (Table 1) or higher (Table 2) than the pre-established reference.

The "control" concentration for a particular protein in a particular cell type or tissue may alternatively be pre-established by an analysis of protein expression in one or more subjects that have responded to treatment with a JAK inhibitor. This pre-established reference value (which may be an average or median expression level taken from multiple subjects that have responded to the therapy) may then be used as the "control" expression level in the comparison with the test sample. In such a comparison, the subject is predicted to respond to a therapy comprising a JAK inhibitor if the concentration of the protein being analyzed is the same as, or comparable to (e.g., at least 85% but less than 100% of), the pre-established reference.

In certain embodiments, the "control" is a pre-established cut-off value. A cut-off value is typically a concentration of a protein above or below which is considered predictive of responsiveness of a subject to a therapy of interest. Thus, in accordance with the methods and compositions described herein, a reference protein concentration (e.g., of a protein of Table 1 or Table 2) is identified as a cut-off value, above or below of which is predictive of responsiveness to a therapy comprising a JAK inhibitor. Cut-off values determined for use in the methods described herein can be compared with, e.g., published ranges of concentrations but can be individualized to the methodology used and patient population.

In some embodiments, the concentration of the protein being analyzed is reduced as compared to the concentration of that protein in a control. For example, the concentration of the protein being analyzed can be at least 1.5, 2, 3, 4, 5, 6, 7, 8, 9, 10, 20, 25, 50, 75, or 100 times lower, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% lower, than the concentration of that protein in a control.

In some embodiments, the concentration of the protein being analyzed is increased as compared to the concentration of that protein in a control. For example, the concentration of the protein being analyzed can be at least 1.5, 2, 3, 4, 5, 6, 7, 8, 9, 10, 20, 25, 50, 75, or 100 times higher, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% higher, than the concentration of that protein in a control.

Methods of Identifying Therapeutic Responsiveness to a Therapy Comprising a JAK Inhibitor Several proteins have been identified in the Examples whose expression levels, in subjects who respond to treatment with a JAK inhibitor, change during the course of treatment and are therefore useful in identifying therapeutic responsiveness (e.g., improvement in disease scores and/or disease resolution) of a subject having GvHD to a therapy comprising a JAK inhibitor. These proteins are identified in Table 13.

A reduced protein concentration in a biological sample obtained from a subject after treatment with a JAK inhibitor, as compared to the baseline expression level in a biological sample obtained from the subject before treatment with a JAK inhibitor, of one or more (e.g., at least 1, 2, 3, 4, 5, 6, 7, 8, 9, 10, 11, 12, 13, 14, 15, 16, 17, 18, 19, or 20) of INPPL1, LAT2, CLEC7A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOS-CAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, HAVCR2, CD84, STX8, LY9, ZBTB16, CD200R1, TOP2B, THY 1, PRKRA, ITGB1BP2, CD48, CD244, HCLS1, MPO, SIT1, ICAM3, SOST, DDX58, TNF-R2, TRAF2, SMAD1, LAIR-2, PIK3AP1, VSIG4, SIGLEC10, CD6, SKAP1, FCRL5, CD177, KLRD1, ERBB2IP, MILR1, MIF, SNAP23, NUB1, TIGAR, STAMPB, DSC2, LAIR1, FKBP1B, RASSF2, FATC1, CBL, IgG Fc receptor II-b, GLO1, PVALB, SCAMP3, SLAMF8, STX16, TNF-R1, DFFA, PPP1R2, ANG-1, CCL5, MAP2K6, CRKL, CD38, CXCL5, PILRA, IRAK1, CA13, STX6, PRTN3, IL-5R-alpha, ESM-1, EGLN1, CLEC1B, TYMP, SNAP29, PDGF subunit A, TNFRSF11A, gal-8, GCNT1, STK4, TNC, THBS4, CLEC4D, SIGLEC6, WASF1, WAS, COMT, RETN, SH2D1A, RNASE3, PAR-1, CD69, SIGLEC1, FR-gamma, ADAM 8, AZU1, AREG, SDC4, DCTN2, BID, RELT, CLEC5A, APEX1, PSP-D, FGR, SELE, SELL, MESDC2, IQGAP2, CRTAM, LILRB2, TANK, CPXM1, ARSB, SLAMF1, PEBP1, STIP1, PDGF subunit B, SCARF1, DEFA1, EPHB4, ARHGAP1, CLM-1, DAB2, LYN, CASP-8, APBB1IP, ANXA11, ICAM1, PRKCQ, VCAM1, HDGF, CD2AP, TNFRSF6B, CLEC1A, TNFRSF14, TACC3, MMP-1, NRP1, ZBTB17, NADK, PLXNA4, MMP-9, NCR1, AMIGO2, FES, CD79B, TNXB, TXNDC5, TRANCE, ARG1, PCDH17, LRMP, C1QTNF1, CLM-6, CKAP4, APP, PGLYRP1, LILRA5, CLEC10A, NMNAT1, IL-6RA, ATG4A, TIMP1, COCH, DKN1A, CD1C, DECR1, DAG1, IGFBP-2, RET, GSAP, PILRB, CLEC6A, PECAM-1, PXN, ADGRG1, DPP7, TDRKH, Siglec-9, CD40-L, VEGFC, LYVE1, FADD, FCRL1, EGF, HGF, GZMH, CLEC4G, LY75, PRDX3, COL4A1, CEACAM8, SEMA7A, NUDT5, FCRL6, PAPPA, FASLG, GRN, and/or MATN3 is indicative that the subject has undergone a therapeutic response to the JAK inhibitor.

An increased protein concentration in a biological sample obtained from a subject after treatment with a JAK inhibitor, as compared to the baseline expression level in a biological sample obtained from the subject before treatment with a JAK inhibitor, of one or more (e.g., at least 1, 2, 3, 4, 5, 6, 7, 8, 9, 10, 11, 12, 13, 14, 15, 16, 17, 18, 19, or 20) of TMPRSS15, CCL11, FAM3B, MMP7, NCAM1, Gal-3, CCL25, THPO, CCL11, hK14, KIM1, Flt3L, PLIN1, SPON2, Gal-4, FABP4, DNER, GAL, CPM, VWC2, PPY, PAM, PVR, SERPINA5, ST3GAL1, CST5, CES2, CNDP1, CX3CL1, HO-1, PRELP, ADM, VSIG2, FABP2, CEACAM5, SLITRK2, MCP-1, NTRK3, CLUL1, CXCL16, SCF, TMPRSS5, REG4, hK11, SCGB3A1, DKKL1, NEP, CPA2, Ep-CAM, THBS2, GPNMB, ITGB5, GT, APLP1, TACSTD2, NINJ1, REN, GCG, SERPINA9, KAZALD1, SERPINA12, PODXL, AMN, IGF1R, LTBP2, ANGPTL3, SCARA5, B4GAT1, ROBO2, PDGFC, CA12, DDC, EDIL3, XPNPEP2, PRTG, NQO2, AMBP, ERBB2, IL6, MCP-1, VEGFD, GDF-2, MUC-16, KLK10, FAM3C, uPA, AGR2, METRNL, RTN4R, IGF2R, NTRK2, ITGB6, SCARF2, SCGB3A2, RGMB, EZR, PROC, FURIN, PIgR, and/or SMOC2 is indicative that the subject has undergone a therapeutic response to the JAK inhibitor.

A reduced protein concentration in a biological sample obtained from a subject after treatment with a JAK inhibitor, as compared to the baseline expression level in a biological sample obtained from the subject before treatment with a JAK inhibitor, of one or more (e.g., at least 1, 2, 3, 4, 5, 6, 7, 8, 9, 10, 11, 12, 13, 14, 15, 16, 17, 18, 19, or 20) of INPPL1, LAT2, CLEC5A, PPP1R9B, NEMO, SH2B3, BCR, CD5, DNAJB1, CCL17, ITGB2, BANK1, TPSAB1, YES1, LAMP3, GM-CSF-R-alpha, CNTNAP2, ZBTB16, CD163, TXLNA, MEPE, BACH1, MAX, NFKBIE, hOS-CAR, LAT, PTPRJ, SIRT2, SIRPB1, AXIN1, EIF4G1, PTX3, TRIM5, IDUA, NCF2, SELP, ARHGEF12, CASP-3, CD27, MAP4K5, DAPP1, PRDX5, TLT-2, PARK7, IL2-RA, FOXO1, ST1A1, GRAP2, NBN, CD93, FCGR2A, DCTN1, IRF9, HAVCR2, CD84, STX8, LY9, ZBTB16, CD200R1, TOP2B, THY 1, PRKRA, ITGB1BP2, CD48, CD244, HCLS1, MPO, SIT1, ICAM3, SOST, DDX58, TNF-R2, TRAF2, SMAD1, LAIR-2, PIK3AP1, VSIG4, SIGLEC10, CD6, SKAP1, FCRL5, CD177, KLRD1, ERBB2IP, MILR1, MIF, SNAP23, NUB1, TIGAR, STAMPB, DSC2, LAIR1, FKBP1B, RASSF2, FATC1, CBL, IgG Fc receptor II-b, GLO1, PVALB, SCAMP3, SLAMF8, STX16, TNF-R1, DFFA, PPP1R2, ANG-1, CCL5, MAP2K6, CRKL, CD38, CXCL5, PILRA, IRAK1, CA13, STX6, PRTN3, IL-5R-alpha, ESM-1, EGLN1, CLEC1B, TYMP, SNAP29, PDGF subunit A, TNFRSF11A, gal-8, GCNT1, STK4, TNC, THBS4, CLEC4D, SIGLEC6, WASF1, WAS, COMT, RETN, SH2D1A, RNASE3, PAR-1, CD69, SIGLEC1, FR-gamma, ADAM 8, AZU1, AREG, SDC4, DCTN2, BID, RELT, CLEC5A, APEX1, PSP-D, FGR, SELE, SELL, MESDC2, IQGAP2, CRTAM, LILRB2, TANK, CPXM1, ARSB, SLAMF1, PEBP1, STIP1, PDGF subunit B, SCARF1, DEFA1, EPHB4, ARHGAP1, CLM-1, DAB2, LYN, CASP-8, APBB1IP, ANXA11, ICAM1, PRKCQ, VCAM1, HDGF, CD2AP, TNFRSF6B, CLEC1A, TNFRSF14, TACC3, MMP-1, NRP1, ZBTB17, NADK, PLXNA4, MMP-9, NCR1, AMIGO2, FES, CD79B, TNXB, TXNDC5, TRANCE, ARG1, PCDH17, LRMP, C1QTNF1, CLM-6, CKAP4, APP, PGLYRP1, LILRA5, CLEC10A, NMNAT1, IL-6RA, ATG4A, TIMP1, COCH, DKN1A, CD1C, DECR1, DAG1, IGFBP-2, RET, GSAP, PILRB, CLEC6A, PECAM-1, PXN, ADGRG1, DPP7, TDRKH, Siglec-9, CD40-L, VEGFC, LYVE1, FADD, FCRL1, EGF, HGF, GZMH, CLEC4G, LY75, PRDX3, COL4A1, CEACAM8, SEMA7A, NUDT5, FCRL6, PAPPA, FASLG, GRN, and/or MATN3 combined with an increased protein concentration in a biological sample obtained from the subject after treatment with a JAK inhibitor, as compared to the baseline expression level in a biological sample obtained from the subject before treatment with a JAK inhibitor, of one or more (e.g., at least 1, 2, 3, 4, 5, 6, 7, 8, 9, 10, 11, 12, 13, 14, 15, 16, 17, 18, 19, or 20) of TMPRSS15, CCL11, FAM3B, MMP7, NCAM1, Gal-3, CCL25, THPO, CCL11, hK14, KIM1, Flt3L, PLIN1, SPON2, Gal-4, FABP4, DNER, GAL, CPM, VWC2, PPY, PAM, PVR, SERPINA5, ST3GAL1, CST5, CES2, CNDP1, CX3CL1, HO-1, PRELP, ADM, VSIG2, FABP2, CEACAM5, SLITRK2, MCP-1, NTRK3, CLUL1, CXCL16, SCF, TMPRSS5, REG4, hK11, SCGB3A1, DKKL1, NEP, CPA2, Ep-CAM, THBS2, GPNMB, ITGB5, GT, APLP1, TACSTD2, NINE, REN, GCG, SERPINA9, KAZALD1, SERPINA12, PODXL, AMN, IGF1R, LTBP2, ANGPTL3, SCARA5, B4GAT1, ROBO2, PDGFC, CA12, DDC, EDIL3, XPNPEP2, PRTG, NQO2, AMBP, ERBB2, IL6, MCP-1, VEGFD, GDF-2, MUC-16, KLK10, FAM3C, uPA, AGR2, METRNL, RTN4R, IGF2R, NTRK2, ITGB6, SCARF2, SCGB3A2, RGMB, EZR, PROC, FURIN, PIgR, and/or SMOC2 is indicative that the subject has undergone a therapeutic response to the JAK inhibitor.

In some embodiments, the GvHD is acute GvHD. In other embodiments, the GvHD is chronic GvHD.

Biological Samples

Suitable biological samples for the methods described herein include any biological fluid, cell, tissue, or fraction thereof, which includes proteins of interest. A biological sample can be, for example, a specimen obtained from a human subject or can be derived from such a subject. For example, a biological sample can be a biological fluid such as blood, serum, plasma, urine, spinal fluid, saliva, lacrimal fluid, or sweat, or such a sample absorbed onto a substrate (e.g., glass, polymer, or paper).

A biological sample can be obtained from a subject having, suspected of having, or at risk of developing, GvHD. In certain embodiments, the subject has acute GvHD. In some embodiments, the subject has chronic GvHD.

Methods for obtaining and/or storing samples that preserve the activity or integrity of molecules (e.g., proteins) in the sample are well known to those skilled in the art. For example, a biological sample can be further contacted with one or more additional agents such as buffers and/or inhibitors, including one or more of nuclease, protease, and phosphatase inhibitors, which preserve or minimize changes in the molecules in the sample.

Determining Expression Levels/Concentrations of Biomarkers

The presence or expression level (amount) of a gene can be determined by detecting and/or measuring the level of protein expression of the gene.

In one embodiment, the expression of a gene can be determined by detecting and/or measuring expression or concentration of a protein encoded by the gene. Methods of determining protein expression/concentration are well known in the art. A generally used method involves the use of antibodies specific for the target protein of interest. For example, methods of determining protein expression include, but are not limited to, western blot or dot blot analysis, immunohistochemistry (e.g., quantitative immunohistochemistry), immunocytochemistry, enzyme-linked immunosorbent assay (ELISA), enzyme-linked immunosorbent spot (ELISPOT; Coligan, J. E., et al., eds. (1995) Current Protocols in Immunology. Wiley, New York), radio-immunoassay, chemiluminescent immunoassay, electro-chemiluminescence immunoassay, latex turbidimetric immunoassay, latex photometric immunoassay, immuno-chromatographic assay, and antibody array analysis (see, e.g., U.S. Publication Nos. 20030013208 and 2004171068, the disclosures of each of which are incorporated herein by reference in their entirety).

In one example, the presence or amount of protein expression of a gene (e.g., a gene depicted in Table 1, Table 2, or Table 13) can be determined using a western blotting technique. For example, a lysate can be prepared from a biological sample, or the biological sample itself, can be contacted with Laemmli buffer and subjected to sodium-dodecyl sulfate polyacrylamide gel electrophoresis (SDS-PAGE). SDS-PAGE-resolved proteins, separated by size, can then be transferred to a filter membrane (e.g., nitrocellulose) and subjected to immunoblotting techniques using a detectably-labeled antibody specific to the protein of interest. The presence or amount of bound detectably-labeled antibody indicates the presence or amount of protein in the biological sample.

In another example, an immunoassay can be used for detecting and/or measuring the protein expression of a gene (e.g., a gene depicted in Table 1, Table 2, or Table 13). As above, for the purposes of detection, an immunoassay can be performed with an antibody that bears a detection moiety (e.g., a fluorescent agent or enzyme). Proteins from a biological sample can be conjugated directly to a solid-phase matrix (e.g., a multi-well assay plate, nitrocellulose, agarose, sepharose, encoded particles, or magnetic beads) or it can be conjugated to a first member of a specific binding pair (e.g., biotin or streptavidin) that attaches to a solid-phase matrix upon binding to a second member of the specific binding pair (e.g., streptavidin or biotin). Such attachment to a solid-phase matrix allows the proteins to be purified away from other interfering or irrelevant components of the biological sample prior to contact with the detection antibody and also allows for subsequent washing of unbound antibody. Here as above, the presence or amount of bound detectably-labeled antibody indicates the presence or amount of protein in the biological sample.

There is no particular restriction as to the form of the antibody and the present disclosure includes polyclonal antibodies, as well as monoclonal antibodies. The antiserum obtained by immunizing animals, such as rabbits with a protein or fragment thereof (i.e., a protein or an immunological fragment thereof from Table 1, Table 2, or Table 13), as well polyclonal and monoclonal antibodies of all classes, human antibodies, and humanized antibodies produced by genetic recombination, are also included. Antibodies or antibody fragments specific for a protein encoded by one or more biomarkers can also be generated by in vitro methods such as phage display. Moreover, the antibody may be an antibody fragment or modified-antibody, so long as it binds to a protein encoded by a biomarker of the invention. For instance, Fab, F (ab') 2, Fv, or single chain Fv (scFv) in which the H chain Fv and the L chain Fv are suitably linked by a linker (Huston et al., *Proc. Natl. Acad. Sci. USA*, 85:5879-5883, (1988)) can be given as antibody fragments.

The antibodies may be conjugated to various molecules, such as fluorescent substances, radioactive substances, and luminescent substances. Methods to attach such moieties to an antibody are already established and conventional in the field (see, e.g., U.S. Pat. Nos. 5,057,313 and 5,156,840).

Examples of methods that assay the antigen-binding activity of the antibodies include, for example, measurement of absorbance, enzyme-linked immunosorbent assay (ELISA), enzyme immunoassay (EIA), radioimmunoassay (RIA), and/or immunofluorescence. For example, when using ELISA, a protein encoded by a biomarker of the invention is added to a plate coated with the antibodies of the present disclosure, and then, the antibody sample, for example, culture supernatants of antibody-producing cells, or purified antibodies are added. Then, secondary antibody recognizing the primary antibody, which is labeled by alkaline phosphatase and such enzymes, is added, the plate is incubated and washed, and the absorbance is measured to evaluate the antigen-binding activity after adding an enzyme substrate such as p-nitrophenyl phosphate. As the protein, a protein fragment, for example, a fragment comprising a C-terminus, or a fragment comprising an N-terminus may be used. To evaluate the activity of the antibody of the invention, BIAcore (GE Healthcare) may be used.

By using these methods, the antibody and a sample presumed to contain a protein of interest are contacted, and the protein encoded by a biomarker of the invention is detected or assayed by detecting or assaying the immune complex formed between the above-mentioned antibody and the protein.

Mass spectrometry based quantitation assay methods, for example, but not limited to, multiple reaction monitoring (MRM)-based approaches in combination with stable-isotope labeled internal standards, are an alternative to immunoassays for quantitative measurement of proteins. These approaches do not require the use of antibodies (see, for example, Addona et al., *Nat. Biotechnol.*, 27:633-641, 2009; Kuzyk et al., *Mol. Cell Proteomics*, 8:1860-1877, 2009; Paulovich et al., *Proteomics Clin. Appl.*, 2:1386-1402, 2008). In addition, MRM offers superior multiplexing capabilities, allowing for the simultaneous quantification of numerous proteins in parallel. The basic theory of these methods has been well-established and widely utilized for drug metabolism and pharmacokinetics analysis of small molecules.

In some embodiments, the concentration of two proteins, three proteins, four proteins, five proteins, six proteins, seven proteins, eight proteins, nine proteins, 10 proteins, 11 proteins, 12 proteins, 13 proteins, or 14 proteins, or at least two proteins, at least three proteins, at least four proteins, at least five proteins, at least six proteins, at least seven proteins, at least eight proteins, at least nine proteins, at least 10 proteins, at least 11 proteins, at least 12 proteins, at least 13 proteins, or at least 14 proteins from Table 1 can be assessed and/or measured.

In some embodiments, the concentration of two proteins, three proteins, four proteins, or five proteins, or at least two proteins, at least three proteins, at least four proteins, or at least five proteins from Table 2 can be assessed and/or measured.

In some embodiments, the concentration of two proteins, three proteins, four proteins, five proteins, six proteins, seven proteins, eight proteins, nine proteins, 10 proteins, 11 proteins, 12 proteins, 13 proteins, 14 proteins, 15 proteins, 16 proteins, 17 proteins, 18 proteins, 19 proteins, or 20 proteins, or at least two proteins, at least three proteins, at least four proteins, at least five proteins, at least six proteins, at least seven proteins, at least eight proteins, at least nine proteins, at least 10 proteins, at least 11 proteins, at least 12 proteins, at least 13 proteins, at least 14 proteins, at least 15 proteins, at least 16 proteins, at least 17 proteins, at least 18 proteins, at least 19 proteins, or at least 20 proteins from Table 13 can be assessed and/or measured.

In some embodiments of the methods described herein, the method includes measuring a concentration of MCP-3 that is below 15 pg/ml, below 10 pg/ml, below 9 pg/ml, below 8 pg/ml, below 7 pg/ml, below 6 pg/ml, below 5 pg/ml, below 4 pg/ml, or below 3 pg/ml.

In some embodiments of the methods described herein, the method includes measuring a concentration of Reg3A that is below 45,000 pg/ml, below 40,000 pg/ml, below 35,000 pg/ml, below 30,000 pg/ml, below 25,000 pg/ml, below 20,000 pg/ml, below 15,000 pg/ml, or below 10,000 pg/ml.

In some embodiments of the methods described herein, the method includes measuring a concentration of TNFRSF6B that is below 400 pg/ml, below 350 pg/ml, below 300 pg/ml, below 250 pg/ml, or below 200 pg/ml.

In some embodiments of the methods described herein, the method includes measuring a concentration of SCF that is above 350 pg/ml, above 400 pg/ml, above 450 pg/ml, above 500 pg/ml, above 600 pg/ml, or above 650 pg/ml.

In some embodiments of the methods described herein, the method includes measuring a concentration of CXCL10 that is below 900 pg/ml, below 800 pg/ml, below 700 pg/ml, below 600 pg/ml, below 500 pg/ml, or below 400 pg/ml.

In some embodiments of the methods described herein, the method includes measuring a concentration of IL-8 that is below 40 pg/ml, below 35 pg/ml, below 30 pg/ml, below 25 pg/ml, below 20 pg/ml, below 15 pg/ml, or below 10 pg/ml.

In some embodiments of the methods described herein, the method includes measuring a concentration of ST2 that is below 140,000 pg/ml, below 130,000 pg/ml, below 120,000 pg/ml, below 110,000 pg/ml, below 100,000 pg/ml, below 90,000 pg/ml, below 80,000 pg/ml, or below 70,000 pg/ml.

In some embodiments of the methods described herein, the method includes measuring a concentration of CALCA that is below 3,000 pg/ml, below 2,900 pg/ml, below 2,800 pg/ml, below 2,700 pg/ml, below 2,600 pg/ml, below 2,500 pg/ml, below 2,400 pg/ml, below 2,300 pg/ml, below 2,200 pg/ml, below 2,100 pg/ml, or below 2,000 pg/ml.

In some embodiments of the methods described herein, the method includes measuring a concentration of TNF-R1 that is below 12,000 pg/ml, below 11,500 pg/ml, below 11,000 pg/ml, below 10,500 pg/ml, below 10,000 pg/ml, or below 9,500 pg/ml.

In some embodiments of the methods described herein, the method includes measuring a concentration of IL-6 that is below 3.5 pg/ml, below 3 pg/ml, below 2.5 pg/ml, below 2 pg/ml, or below 1.5 pg/ml.

In some embodiments of the methods described herein, the method includes measuring a concentration of CCL19 that is below 1,000 pg/ml, below 900 pg/ml, below 800 pg/ml, below 700 pg/ml, below 600 pg/ml, or below 500 pg/ml.

In some embodiments of the methods described herein, the method includes measuring a concentration of PON3 that is above 150,000 pg/ml, above 200,000 pg/ml, above 250,000 pg/ml, above 300,000 pg/ml, above 350,000 pg/ml, or above 400,000 pg/ml.

JAK Inhibitors

In some embodiments, the JAK inhibitor is a compound that inhibits JAK1, JAK2, JAK3, and/or TYK2. In some embodiments, the JAK inhibitor is selective for JAK1 and JAK2 over JAK3 and TYK2. In some embodiments, the JAK inhibitor is selective for JAK1 over JAK2, JAK3, and TYK2. For example, some of the compounds described herein, or a pharmaceutically acceptable salt thereof, preferentially inhibit JAK1 over one or more of JAK2, JAK3, and TYK2. In some embodiments, the compounds or salts inhibit JAK1 preferentially over JAK2 (e.g., have a JAK2/JAK1 $IC_{50}$ ratio>1). In some embodiments, the compounds or salts are about 10-fold more selective for JAK1 over JAK2. In some embodiments, the compounds or salts are about 3-fold, about 5-fold, about 10-fold, about 15-fold, or about 20-fold more selective for JAK1 over JAK2 as calculated by measuring IC$_{50}$ at 1 mM ATP.

In some embodiments, the JAK inhibitor is 3-cyclopentyl-3-[4-(7H-pyrrolo[2,3-d]pyrimidin-4-yl)-1H-pyrazol-1-yl]propanenitrile.

In some embodiments, the JAK inhibitor is (3R)-3-cyclopentyl-3-[4-(7H-pyrrolo[2,3-d]pyrimidin-4-yl)-1H-pyrazol-1-yl]propanenitrile (ruxolitinib; also known as INCB018424).

3-Cyclopentyl-3-[4-(7H-pyrrolo[2,3-d]pyrimidin-4-yl)-1H-pyrazol-1-yl]propanenitrile and ruxolitinib can be made by the procedure described in U.S. Pat. No. 7,598,257 (Example 67), filed Dec. 12, 2006, which is incorporated herein by reference in its entirety.

In some embodiments, the JAK inhibitor is (3R)-3-cyclopentyl-3-[4-(7H-pyrrolo[2,3-d]pyrimidin-4-yl)-1H-pyrazol-1-yl]propanenitrile phosphoric acid salt.

In some embodiments, the JAK inhibitor is baricitinib, tofacitinib, oclacitinib, filgotinib, gandotinib, lestaurtinib, momelotinib, bacritinib, PF-04965842, upadacitinib, peficitinib, fedratinib, cucurbitacin I, ATI-501 (Aclaris), ATI-502 (Aclaris), JTE052 (Leo Pharma and Japan Tobacco), or CHZ868.

In some embodiments, the JAK inhibitor can be an isotopically-labeled compound, or a pharmaceutically acceptable salt thereof. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I and $^{131}$I. For example, one or more hydrogen atoms in a compound of the present disclosure can be replaced by deuterium atoms (e.g., one or more hydrogen atoms of a C$_{1-6}$ alkyl group of Formula (I) can be optionally substituted with deuterium atoms, such as —CD$_3$ being substituted for —CH$_3$).

One or more constituent atoms of the compounds described herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. Med. Chem. 2011, 54, 201-210; R. Xu et. al. J. Label Compd. Radiopharm. 2015, 58, 308-312). In particular, substitution at one or more metabolism sites may afford one or more of the therapeutic advantages.

Accordingly, in some embodiments, the JAK inhibitor is a compound, wherein one or more hydrogen atoms in the compound are replaced by deuterium atoms, or a pharmaceutically acceptable salt thereof.

In some embodiments, the JAK inhibitor is ruxolitinib, wherein one or more hydrogen atoms are replaced by deuterium atoms, or a pharmaceutically acceptable salt thereof. In some embodiments, the JAK inhibitor is any of the compounds in U.S. Pat. No. 9,249,149 (which is incorporated herein by reference in its entirety), or a pharmaceutically acceptable salt thereof. In some embodiments, the JAK inhibitor is CTP-543, or a pharmaceutically acceptable salt thereof. In some embodiments, the compound is a compound of Formula I:

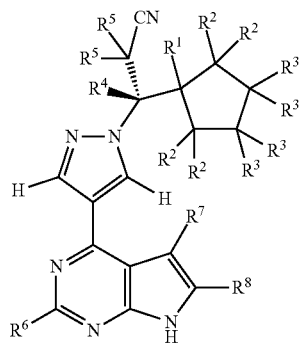

or a pharmaceutically acceptable salt thereof, wherein:

R$^1$ is selected from H and D;

each R$^2$ is independently selected from H and D, provided that each R$^2$ attached to a common carbon is the same;

each R$^3$ is independently selected from H and D, provided that each R$^3$ attached to a common carbon is the same;

R$^4$ is selected from H and D;

each R$^5$ is the same and is selected from H and D; and

R$^6$, R$^7$, and R$^8$ are each independently selected from H and D; provided that when R$^1$ is H, each R$^2$ and each R$^3$ are H, R$^4$ is H, and each of R$^6$, R$^7$, and R$^8$ is H, then each R$^5$ is D.

In some embodiments, the JAK inhibitor is a compound of Formula I selected from the following compounds 100-130 in the table below (wherein R$^6$, R$^7$, and R$^8$ are each H), or a pharmaceutically acceptable salt thereof. In some embodiments, the JAK inhibitor is a compound of Formula I selected from the following compounds 200-231 in the table below (wherein R$^6$, R$^7$, and R$^8$ are each D), or a pharmaceutically acceptable salt thereof.

| Compound | R$^1$ | Each R$^2$ | Each R$^3$ | R$^4$ | Each R$^5$ |
|---|---|---|---|---|---|
| 100 | H | H | H | D | H |
| 101 | H | H | H | H | D |
| 102 | H | H | H | D | D |
| 103 | H | H | D | H | H |
| 104 | H | H | D | D | H |
| 105 | H | H | D | H | D |
| 106 | H | H | D | D | D |
| 107 | H | D | H | H | H |
| 108 | H | D | H | D | H |

-continued

| Compound | R¹ | Each R² | Each R³ | R⁴ | Each R⁵ |
|---|---|---|---|---|---|
| 109 | H | D | H | H | D |
| 110 | H | D | H | D | D |
| 111 | H | D | D | H | H |
| 112 | H | D | D | D | H |
| 113 | H | D | D | H | D |
| 114 | H | D | D | D | D |
| 115 | D | H | H | H | H |
| 116 | D | H | H | D | H |
| 117 | D | H | H | H | D |
| 118 | D | H | H | D | D |
| 119 | D | H | D | H | H |
| 120 | D | H | D | D | H |
| 121 | D | H | D | H | D |
| 122 | D | H | D | D | D |
| 123 | D | D | H | H | H |
| 124 | D | D | H | D | H |
| 125 | D | D | H | H | D |
| 126 | D | D | H | D | D |
| 127 | D | D | D | H | H |
| 128 | D | D | D | D | H |
| 129 | D | D | D | H | D |
| 130 | D | D | D | D | D |
| 200 | H | H | H | D | H |
| 201 | H | H | H | H | D |
| 202 | H | H | H | D | D |
| 203 | H | H | D | H | H |
| 204 | H | H | D | D | H |
| 205 | H | H | D | H | D |
| 206 | H | H | D | D | D |
| 207 | H | D | H | H | H |
| 208 | H | D | H | D | H |
| 209 | H | D | H | H | D |
| 210 | H | D | H | D | D |
| 211 | H | D | D | H | H |
| 212 | H | D | D | D | H |
| 213 | H | D | D | H | D |
| 214 | H | D | D | D | D |
| 215 | D | H | H | H | H |
| 216 | D | H | H | D | H |
| 217 | D | H | H | H | D |
| 218 | D | H | H | D | D |
| 219 | D | H | D | H | H |
| 220 | D | H | D | D | H |
| 221 | D | H | D | H | D |
| 222 | D | H | D | D | D |
| 223 | D | D | H | H | H |
| 224 | D | D | H | D | H |
| 225 | D | D | H | H | D |
| 226 | D | D | H | D | D |
| 227 | D | D | D | H | H |
| 228 | D | D | D | D | H |
| 229 | D | D | D | H | D |
| 230 | D | D | D | D | D |
| 231 | H | H | H | H | H |

In some embodiments, the JAK inhibitor is baricitinib, wherein one or more hydrogen atoms are replaced by deuterium atoms, or a pharmaceutically acceptable salt thereof. In some embodiments, the JAK inhibitor is any of the compounds in U.S. Pat. No. 9,540,367 (which is incorporated herein by reference in its entirety), or a pharmaceutically acceptable salt thereof.

In some embodiments, the JAK inhibitor is a compound of Table 3, or a pharmaceutically acceptable salt thereof. The compounds in Table 3 are selective JAK1 inhibitors (selective over JAK2, JAK3, and TYK2).

TABLE 3

Examples of JAK inhibitors

| Comp. No. | Prep. | Name | Structure |
|---|---|---|---|
| 1 | US 2011/ 0224190 (Example 1) | {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile (itacitinib;; also known as INCB039110) | 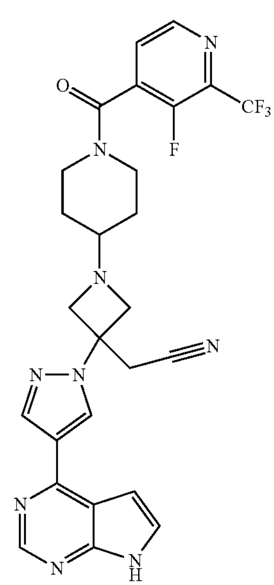 [SMILES: N#CCC1(n2cc(-c3ncnc4[nH]ccc34)cn2)CN(C2CCN(C(=O)c3ccnc(C(F)(F)F)c3F)CC2)C1] |

TABLE 3-continued

Examples of JAK inhibitors

| Comp. No. | Prep. | Name | Structure |
|---|---|---|---|
| 2 | US 2011/ 0224190 (Example 154) | 4-{3-(Cyano-methyl)-3-[4-(7H-pyrrolo [2,3-d]pyrimidin-4-yl)-1H-pyrazol-1-yl] azetidin-1-yl}-N-[4-fluoro-2-(trifluoromethyl) phenyl] piperidine-1-carboxamide | 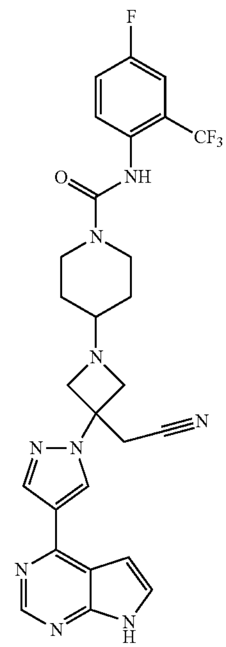 [SMILES: N#CCC1(n2cc(-c3ncnc4[nH]ccc34)cn2)CN(C2CCN(C(=O)Nc3ccc(F)cc3C(F)(F)F)CC2)C1] |
| 3 | US 2011/ 0224190 (Example 85) | [3-[4-(7H-pyrrolo[2,3-d] pyrimidin-4-yl)-1H-pyrazol-1-yl]-1-(1-{[2-(trifluoromethyl) pyrimidin-4-yl] carbonyl}piperidin-4-yl)azetidin-3-yl]acetonitrile | 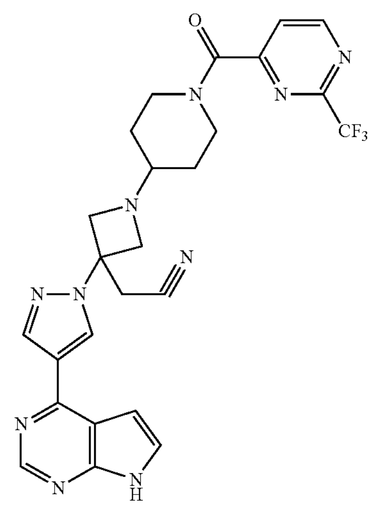 [SMILES: N#CCC1(n2cc(-c3ncnc4[nH]ccc34)cn2)CN(C2CCN(C(=O)c3ccnc(C(F)(F)F)n3)CC2)C1] |
| 4 | US 2014/0343030 (Example 7) | 4-[3-(cyanomethyl)-3-(3',5'-dimethyl-1H,1'H-4,4'-bipyrazol-1-yl) azetidin-1-yl] 2,5-difluoro-N-[(1S)-2,2,2-trifluoro-1-methylethyl] benzamide | 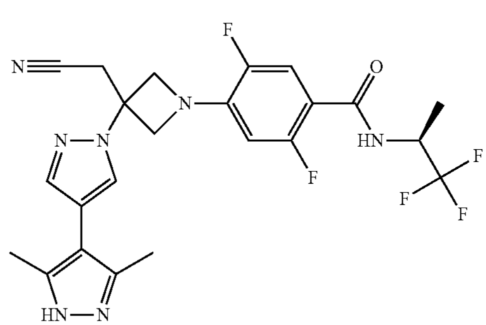 [SMILES: Cc1n[nH]c(C)c1-c1cnn(C2(CC#N)CN(c3cc(F)c(C(=O)N[C@@H](C)C(F)(F)F)cc3F)C2)c1] |

TABLE 3-continued

Examples of JAK inhibitors

| Comp. No. | Prep. | Name | Structure |
|---|---|---|---|
| 5 | US 2014/0121198 (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 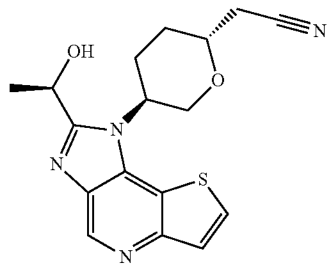 [SMILES: C[C@@H](O)c1nc2cnc3ccsc3c2n1[C@H]1CC[C@H](CC#N)OC1] |
| 6 | US 2010/0298334 (Example 2) | 3-[1-(6-chloro-pyridin-2-yl)pyrrolidin-3-yl]-3-[4-(7H-pyrrolo[2,3-d]pyrimidin-4-yl)-1H-pyrazol-1-yl]propanenitrile | 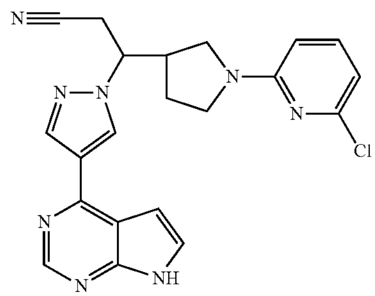 [SMILES: N#CCC(C1CCN(c2cccc(Cl)n2)C1)n1cc(-c2ncnc3[nH]ccc23)cn1] |
| 7 | US 2010/0298334 (Example 13c) | 3-(1-[1,3]oxazolo[5,4-b]pyridin-2-yl-pyrrolidin-3-yl)-3-[4-(7H-pyrrolo[2,3-d]pyrimidin-4-yl)-1H-pyrazol-1-yl]propanenitrile | 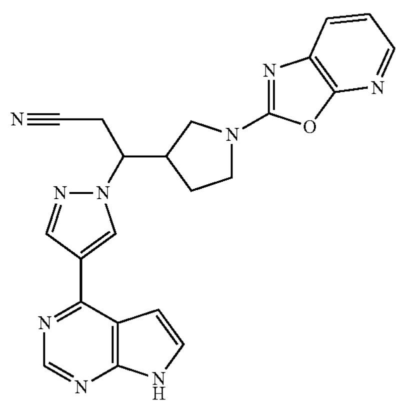 [SMILES: N#CCC(C1CCN(c2nc3cccnc3o2)C1)n1cc(-c2ncnc3[nH]ccc23)cn1] |
| 8 | US 2011/0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluoro-benzonitrile | 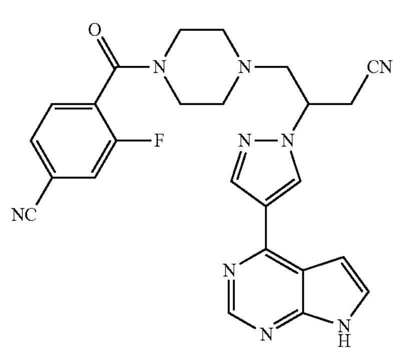 [SMILES: N#CCC(CN1CCN(C(=O)c2ccc(C#N)cc2F)CC1)n1cc(-c2ncnc3[nH]ccc23)cn1] |

TABLE 3-continued

Examples of JAK inhibitors

| Comp. No. | Prep. | Name | Structure |
|---|---|---|---|
| 9 | US 2011/0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 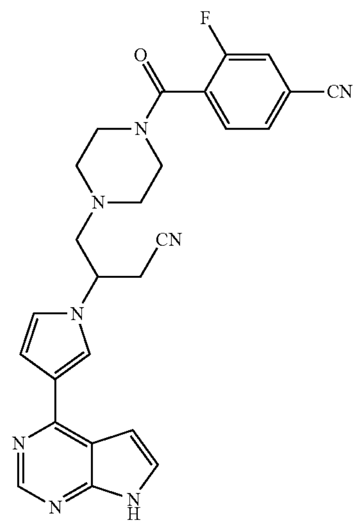 [SMILES: N#CCC(CN1CCN(C(=O)c2ccc(C#N)cc2F)CC1)n1ccc(-c2ncnc3[nH]ccc23)c1] |
| 10 | US 2012/0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 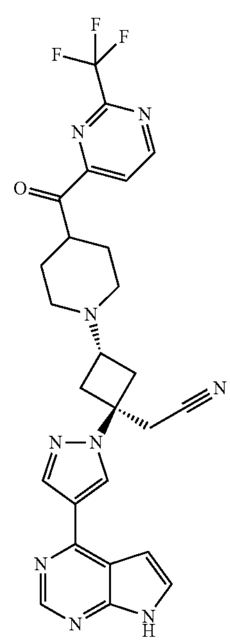 [SMILES: N#CC[C@]1(n2cc(-c3ncnc4[nH]ccc34)cn2)C[C@H](N2CCC(C(=O)c3ccnc(C(F)(F)F)n3)CC2)C1] |

TABLE 3-continued

Examples of JAK inhibitors

| Comp. No. | Prep. | Name | Structure |
|---|---|---|---|
| 11 | US 2012/0149681 (Example 157) | {trans-3-(4-{[4-[(3-hydroxy-azetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 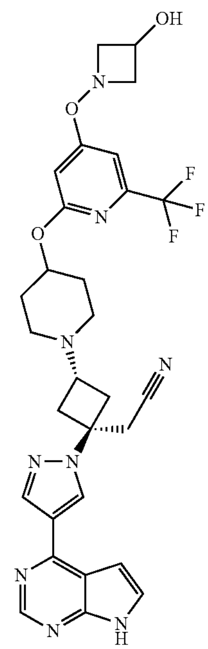 [SMILES: N#CC[C@]1(n2cc(-c3ncnc4[nH]ccc34)cn2)C[C@H](N2CCC(Oc3cc(ON4CC(O)C4)cc(C(F)(F)F)n3)CC2)C1] |
| 12 | US 2012/0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 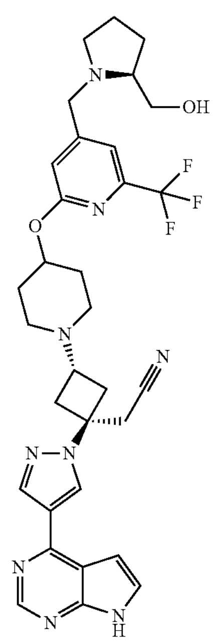 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] |

TABLE 3-continued

Examples of JAK inhibitors

| Comp. No. | Prep. | Name | Structure |
|---|---|---|---|
| 13 | US 2012/ 0149681 (Example 162) | {trans-3-(4-{[4-{[(2R)-2-(hydroxymethyl) pyrrolidin-1-yl] methyl}-6-(trifluoromethyl) pyridin-2-yl] oxy}piperidin-1-yl)-1-[4-(7H-pyrrolo [2,3-d] pyrimidin-4-yl)-1H-pyrazol-1-yl] cyclobutyl} acetonitrile | 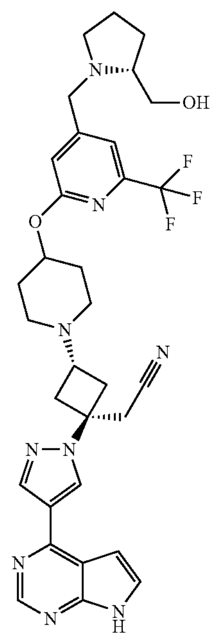 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] |
| 14 | US 2012/ 0149682 (Example 20) | 4-(4-{3-[(dimethylamino) methyl]-5-fluorophenoxy} piperidin-1-yl)-3-[4-(7H-pyrrolo[2,3-d] pyrimidin-4-yl)-1H-pyrazol-1-yl] butanenitrile | 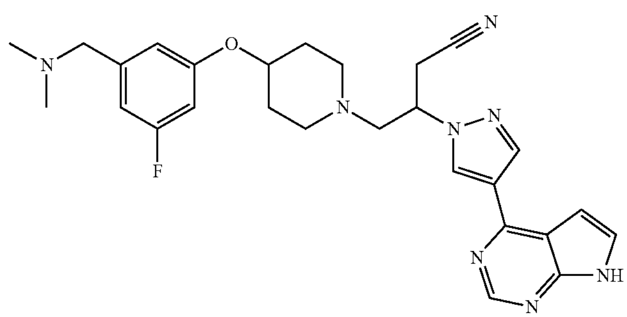 [SMILES: CN(C)Cc1cc(F)cc(OC2CCN(CC(CC#N)n3cc(-c4ncnc5[nH]ccc45)cn3)CC2)c1] |
| 15 | US 2013/ 0018034 (Example 18) | 5-{3-(cyano-methyl)-3-[4-(7H-pyrrolo [2,3-d]pyrimidin-4-yl)-1H-pyrazol-1-yl] azetidin-1-yl}-N-isopropyl-pyrazine-2-carboxamide | 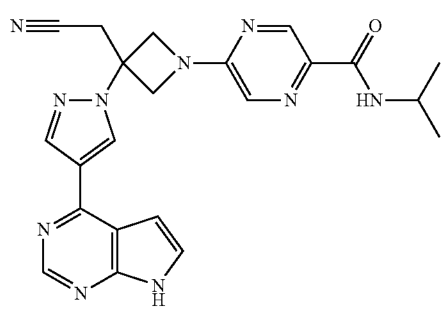 [SMILES: CC(C)NC(=O)c1cnc(N2CC(CC#N)(n3cc(-c4ncnc5[nH]ccc45)cn3)C2)cn1] |

TABLE 3-continued

Examples of JAK inhibitors

| Comp. No. | Prep. | Name | Structure |
|---|---|---|---|
| 16 | US 2013/0018034 (Example 28) | 4-{3-(cyano-methyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 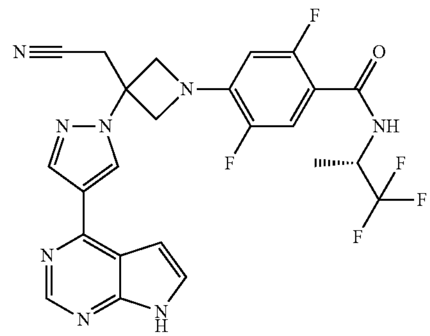 [SMILES: C[C@H](NC(=O)c1cc(F)c(N2CC(CC#N)(n3cc(-c4ncnc5[nH]ccc45)cn3)C2)cc1F)C(F)(F)F] |
| 17 | US 2013/0018034 (Example 34) | 5-{3-(cyano-methyl)-3-[4-(1H-pyrrolo[2,3-b]pyridin-4-yl)-1H-pyrazol-1-yl]azetidin-1-yl}-N-isopropyl-pyrazine-2-carboxamide | 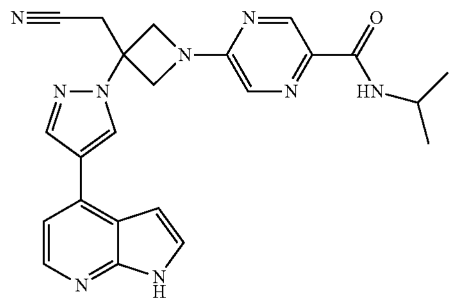 [SMILES: CC(C)NC(=O)c1cnc(N2CC(CC#N)(n3cc(-c4ccnc5[nH]ccc45)cn3)C2)cn1] |
| 18 | US 2013/0045963 (Example 45) | {1-(cis-4-{[6-(2-hydroxy-ethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 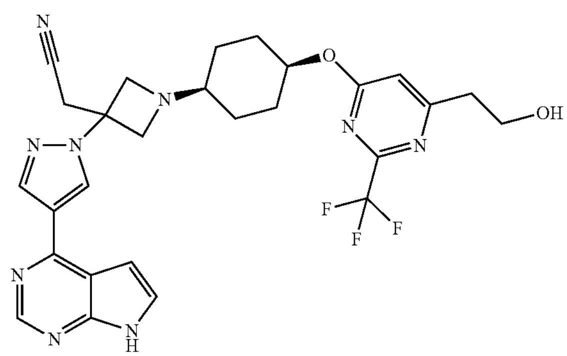 [SMILES: N#CCC1(n2cc(-c3ncnc4[nH]ccc34)cn2)CN([C@H]2CC[C@@H](Oc3cc(CCO)nc(C(F)(F)F)n3)CC2)C1] |
| 19 | US 2013/0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 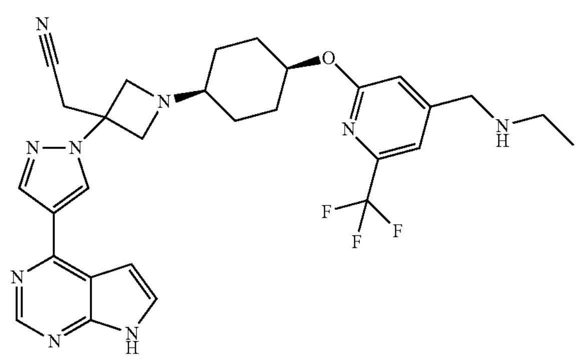 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] |

TABLE 3-continued

Examples of JAK inhibitors

| Comp. No. | Prep. | Name | Structure |
|---|---|---|---|
| 20 | US 2013/ 0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 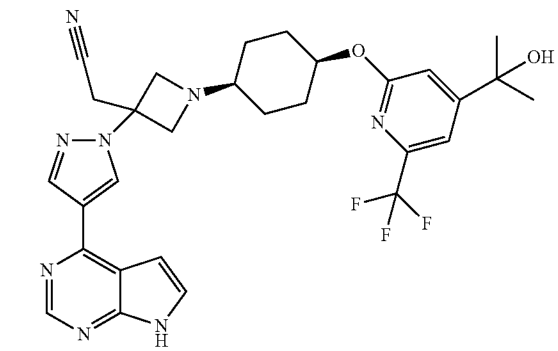 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] |
| 21 | US 2013/ 0045963 (Example 95) | {1-(cis-4-{[4-{[(3R)-3-hydroxy-pyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 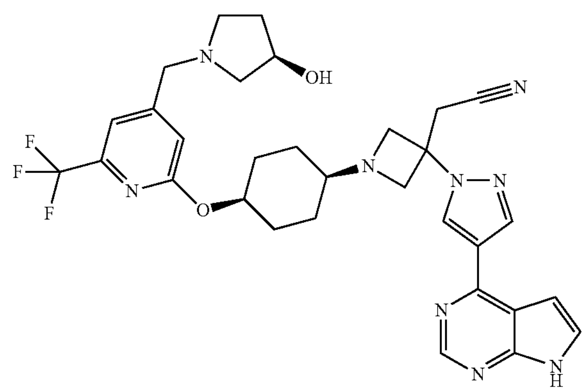 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] |
| 22 | US 2013/ 0045963 (Example 95) | {1-(cis-4-{[4-{[(3S)-3-hydroxy-pyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 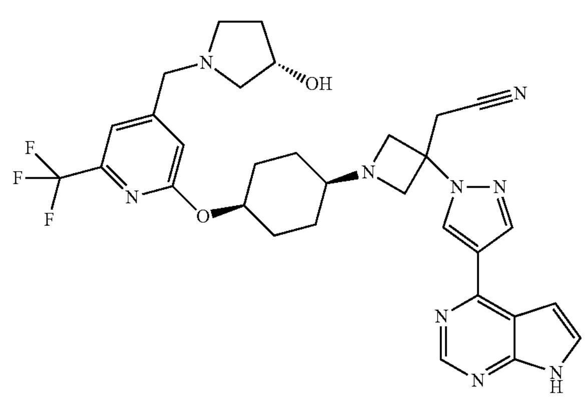 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] |

TABLE 3-continued

Examples of JAK inhibitors

| Comp. No. | Prep. | Name | Structure |
|---|---|---|---|
| 23 | US 2014/ 0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 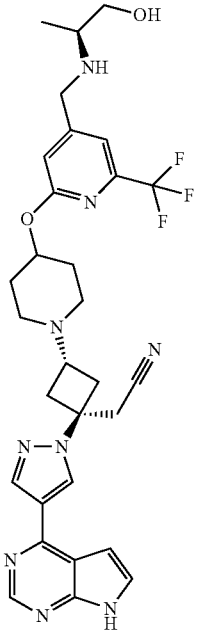 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] |
| 24 | US 2014/ 0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 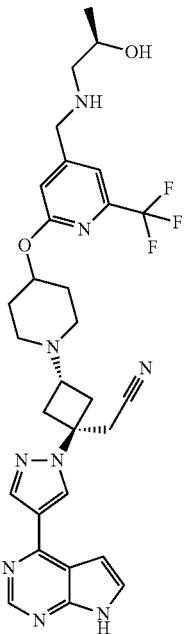 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] |

TABLE 3-continued

Examples of JAK inhibitors

| Comp. No. | Prep. | Name | Structure |
|---|---|---|---|
| 25 | US 2014/ 0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 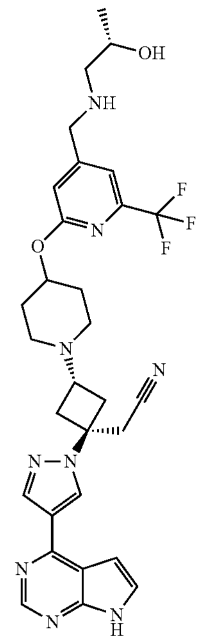 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] |
| 26 | US 2014/ 0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 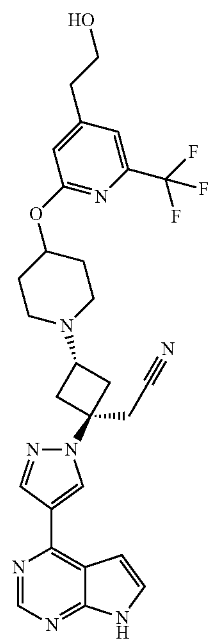 [SMILES: N#CC[C@]1(n2cc(-c3ncnc4[nH]ccc34)cn2)C[C@H](N2CCC(Oc3cc(CCO)cc(C(F)(F)F)n3)CC2)C1] |

In some embodiments, the JAK inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the JAK inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

The synthesis and preparation of {1-{1-[3-fluoro-2-(trifluoromethyl)isonicotinoyl]piperidin-4-yl}-3 [4-(7H-pyrrolo[2,3-d]pyrimidin-4-yl)-1H-pyrazol-1-yl]azetidin-3-yl}acetonitrile and the adipic acid salt of the same can be found, e.g., in US Patent Publ. No. 2011/0224190, filed Mar. 9, 2011, US Patent Publ. No. 2013/0060026, filed Sep. 6, 2012, and US Patent Publ. No. 2014/0256941, filed Mar. 5, 2014, each of which is incorporated herein by reference in its entirety.

In some embodiments, the JAK inhibitor is 4-[3-(cyanomethyl)-3-(3',5'-dimethyl-1H,1'H-4,4'-bipyrazol-1-yl)

azetidin-1-yl]-2,5-difluoro-N-[(1S)-2,2,2-trifluoro-1-methylethyl]benzamide, or a pharmaceutically acceptable salt thereof.

In some embodiments, the JAK inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt.

The synthesis and preparation of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide and the phosphoric acid salt of the same can be found, e.g., in US Patent Publ. No. US 2014/0343030, filed May 16, 2014, which is incorporated herein by reference in its entirety.

In some embodiments, the JAK inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile monohydrate.

Synthesis of ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile and characterization of the anhydrous and monohydrate forms of the same are described in US Patent Publ. No. 2014/0121198, filed Oct. 31, 2013 and US Patent Publ. No. 2015/0344497, filed Apr. 29, 2015, each of which is incorporated herein by reference in its entirety.

In some embodiments, the compounds of Table 3 are prepared by the synthetic procedures described in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, JAK inhibitor is selected from the compounds, or pharmaceutically acceptable salts thereof, of US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

Methods of Treatment

The methods disclosed herein enable the assessment of whether or not a subject having, suspected of having or at risk of developing GvHD is likely to respond (e.g., likely to have greater improvement in disease as evidenced by reduced disease severity and/or disease remission/resolution) to a therapy comprising a JAK inhibitor. A subject having, suspected of having or at risk of developing GvHD who is likely to respond to a JAK inhibitor can be administered a JAK inhibitor (e.g., itacitinib). Conversely, a subject having, suspected of having or at risk of developing GvHD who is less likely to respond to a JAK inhibitor (e.g., itacitinib) can be administered an additional therapy that is suitable for treatment of GvHD.

The methods of this disclosure also enable the stratification of subjects having, suspected of having or at risk of developing GvHD into groups of subjects that are more likely to benefit, and groups of subjects that are less likely to benefit, from treatment comprising a JAK inhibitor. The ability to select such subjects from a pool of GvHD subjects who are being considered for treatment with a JAK inhibitor is beneficial for administering an effective treatment to the subject.

In one embodiment, the subject to be treated with a JAK inhibitor (e.g., itacitinib) has, is suspected of having, or is likely to develop GvHD. In certain embodiments, the subject to be treated with a therapy comprising a JAK inhibitor (e.g., itacitinib) has, is suspected of having, or is likely to develop acute GvHD. In other embodiments, the subject to be treated with a therapy comprising a JAK inhibitor (e.g., itacitinib) has, is suspected of having, or is likely to develop chronic GvHD.

If the subject having GvHD is more likely to respond to a therapy comprising a JAK inhibitor (based on concentrations of one or more of the biomarkers described above (see Tables 1 and 2)), the subject can then be administered an effective amount of the JAK inhibitor (e.g., itacitinib). An effective amount of the JAK inhibitor can suitably be determined by a health care practitioner taking into account, for example, the characteristics of the patient (age, sex, weight, race, etc.), the progression of the disease, and prior exposure to the drug. If the subject is less likely to respond to a therapy comprising a JAK inhibitor, the subject can then be optionally administered a therapy that does not comprise a JAK inhibitor.

The methods can also be applied to individuals at risk of developing GvHD. Such individuals include those who (i) have undergone a transplant (e.g., a hematopoietic stem cell transplant) but have not developed GvHD, or (ii) are preparing for receipt of a transplant (e.g., a hematopoietic stem cell transplant).

After stratifying or selecting a subject based on whether the subject will be more likely or less likely to respond to a JAK inhibitor, a medical practitioner (e.g., a doctor) can administer the appropriate therapeutic modality to the subject. Methods of administering a JAK inhibitor are well known in the art.

In cases where the subject having GvHD and predicted to respond to a JAK inhibitor has been previously administered one or more non-JAK inhibitor therapies, the therapy comprising a JAK inhibitor can replace or augment a previously or currently administered therapy. For example, upon treating with the therapy comprising a JAK inhibitor, administration of the one or more non-JAK inhibitor therapies can cease or diminish, e.g., be administered at lower levels. Administration of the previous therapy can be maintained while the therapy comprising a JAK inhibitor is administered. In some embodiments, a previous therapy can be maintained until the level of the therapy comprising a JAK inhibitor reaches a level sufficient to provide a therapeutic effect.

A subject treated with a JAK inhibitor (e.g., itacitinib) according to the methods described herein can be treated in combination with one or more additional compositions that are effective for treatment of GvHD. Examples of compositions that can be used in such combination treatment include corticosteroids (e.g., methylprednisolone or prednisone), methotrexate, cyclosporine, mycophenolate mofetil, tacrolimus, sirolimus, everolimus, antithymocyte globulin, alemtuzumab, cyclophosphamide, ibrutinib, imatinib, infliximab, etanercept, tocilizumab, alemtuzumab, basiliximab, daclizumab, rituximab, denileukin diftitox, pentostatin, ciclosporin, thalidomide, halofuginone, hydroxychloroquine, and mesenchymal stem cells.

The following are examples of the practice of the invention. They are not to be construed as limiting the scope of the invention in any way.

EXAMPLES

Example 1: Identification of Proteins Differentially Expressed in Patients with Acute Graft-Versus-Host Disease that are Complete Responders to Treatment with Itacitinib Plasma samples were collected from individuals enrolled in a study of itacitinib in combination with corticosteroids for the treatment of Acute Graft-Versus-Host Disease (GvHD). All subjects underwent a first allogeneic hematopoietic stem cell transplantation from any donor source (matched unrelated donor, sibling, haploidentical) using bone marrow, peripheral blood stem cells, or cord blood for hematologic malignancies. The subjects exhibited clinically suspected Grades IIB to IVD acute GvHD, occurring after the allogeneic hematopoietic stem cell transplant. All subjects consented to the blood collection.

Once collected, plasma samples underwent broad proteomic profiling using OLINK™, which allows analysis of >1000 proteins. Samples were separated into the following groups based on the clinical response to treatment with itacitinib (INCB039110). Specifically, samples were classified as "complete responder" (CR), "partial/mixed responder", or "progressive disease/death" (PD/Death) based on their therapeutic response at day 28 of treatment.

Broad proteomic analysis of plasma identified a total of 118 differentially expressed proteins between the CR and PD/Death groups of subjects. Differentially expressed proteins were those that showed a statistically significant difference (p<0.05) and at least a 1.2 fold change between baselines of complete responders and progressive disease/death cohorts. Fold change in this example represents the change of a baseline protein expression level between complete responders and progressive disease/death groups of subjects. Fifty-three proteins were increased and 65 proteins were decreased in CR compared to PD/Death (Table 4). Down-regulated proteins are proteins whose expression decreased over time, while up-regulated proteins are proteins whose expression increased over time. Fold change in expression is shown for each protein, which is a ratio of protein expression level post-treatment to expression level pre-treatment (baseline). Values greater than 1 indicate an increase from baseline, whereas values less than 1 indicate a decrease from baseline.

TABLE 4

Differentially Expressed Proteins at Baseline in the Plasma of Complete Responders Compared to the Progressive Disease/Death Groups

| Up-Regulated in CR Compared to PD/Death | | | Down-Regulated in CR Compared to PD/Death | | |
|---|---|---|---|---|---|
| Protein | Fold Change | Raw P Value | Protein | Fold Change | Raw P Value |
| PON3 | 3.9728 | 0.0005 | MCP-3 | −6.0399 | 0.0004 |
| GCG | 3.481 | 0.0022 | CA5A | −4.5712 | 0.0085 |
| SCF | 3.0746 | 0.003 | CALCA | −4.4035 | 0.0349 |
| PDGF subunit B | 3.0721 | 0.0188 | HAOX1 | −4.3448 | 0.0251 |
|  |  |  | IL8 | −4.0642 | 0.0216 |
| LEP | 3.0194 | 0.0441 | IL6 | −3.8938 | 0.0207 |
| FKBP1B | 2.9644 | 0.0357 | SPINK1 | −3.8821 | 0.012 |
| MBL2 | 2.9639 | 0.0094 | CXCL10 | −3.8124 | 0.0065 |
| SCF | 2.9526 | 0.0026 | SULT2A1 | −3.5143 | 0.0149 |
| GAL | 2.936 | 0.0119 | IL6 | −3.4705 | 0.0258 |
| SCF | 2.9112 | 0.003 | ENPP7 | −3.3791 | 0.0388 |
| ITGB1BP2 | 2.7985 | 0.0306 | PLXNB1 | −2.99 | 0.0105 |
| PVALB | 2.6979 | 0.0084 | VAMP5 | −2.9842 | 0.0315 |
| THPO | 2.6532 | 0.0056 | CCL19 | −2.9578 | 0.0041 |
| CD40-L | 2.645 | 0.041 | CTSL1 | −2.9056 | 0.0018 |
| ANG-1 | 2.6308 | 0.0116 | ACE2 | −2.8742 | 0.0054 |
| SCGB3A1 | 2.5332 | 0.0093 | IL6 | −2.8377 | 0.0121 |
| CD69 | 2.4963 | 0.0119 | CRTAM | −2.6741 | 0.0312 |
| FAM3B | 2.481 | 0.0235 | ALDH1A1 | −2.6667 | 0.0141 |
| GH | 2.4121 | 0.0155 | SIGLEC10 | −2.5993 | 0.0148 |
| CCL5 | 2.3402 | 0.0064 | KRT19 | −2.5964 | 0.0312 |
| MANF | 2.3026 | 0.0174 | SLAMF8 | −2.5417 | 0.0189 |
| SRC | 2.1146 | 0.036 | IL6 | −2.5189 | 0.0141 |
| CRISP2 | 2.0487 | 0.0148 | CDCP1 | −2.4173 | 0.0113 |
| SAA4 | 2.0164 | 0.0348 | N2DL-2 | −2.3079 | 0.0075 |
| CR2 | 2.0089 | 0.0197 | GZMB | −2.307 | 0.0289 |
| SERPINA5 | 2.0067 | 0.0044 | TNFRSF6B | −2.3053 | 0.0037 |
| PFKM | 1.9756 | 8.93E−05 | KYNU | −2.2368 | 0.0217 |
| APOM | 1.9231 | 0.0255 | FOSB | −2.2367 | 0.0169 |
| DCTN2 | 1.8684 | 0.0304 | ALDH3A1 | −2.1808 | 0.0104 |
| HSD11B1 | 1.8131 | 0.0173 | IGFBP-1 | −2.1383 | 0.0472 |
| PDGF subunit A | 1.7697 | 0.0424 | CLM-1 | −2.1323 | 0.012 |
|  |  |  | NFATC3 | −2.0978 | 0.0189 |
| IGFBP3 | 1.7304 | 0.0287 | HAVCR2 | −2.0933 | 0.0196 |
| HS3ST3B1 | 1.7175 | 0.0355 | TNF-R2 | −2.0374 | 0.0091 |
| CDSN | 1.7055 | 0.0227 | DDAH1 | −2.036 | 0.0289 |
| APP | 1.7003 | 0.0484 | CD74 | −1.9824 | 0.0051 |
| TWEAK | 1.6972 | 0.0338 | CKAP4 | −1.9573 | 0.0069 |
| TN-R | 1.653 | 0.0321 | NINJ1 | −1.9125 | 0.0043 |
| AMBP | 1.6302 | 0.0127 | ENTPD2 | −1.8643 | 0.0227 |
| CNTN1 | 1.5831 | 0.0275 | TNFRSF9 | −1.8239 | 0.0276 |
| GCP5 | 1.5583 | 0.0383 | SIGLEC1 | −1.8208 | 0.0229 |
| CNDP1 | 1.555 | 0.0034 | PREB | −1.8178 | 0.0327 |
| NCAM1 | 1.5413 | 0.0011 | AHCY | −1.7883 | 0.043 |
| PROC | 1.514 | 0.0289 | IL12RB1 | −1.7236 | 0.0186 |
| F11 | 1.489 | 0.008 | TNFRSF10A | −1.7188 | 0.0133 |
| NCAN | 1.4147 | 0.0259 | SIRPB1 | −1.7175 | 0.0467 |
| NTRK3 | 1.3885 | 0.0255 | DSC2 | −1.6964 | 0.0261 |
| TIMP4 | 1.3827 | 0.044 | U-PAR | −1.687 | 0.0422 |
| VEGFD | 1.3649 | 0.0365 | TNFRSF4 | −1.677 | 0.0423 |
| HSP 27 | 1.3522 | 0.0446 | TNFRSF10A | −1.6687 | 0.0145 |
| GALNT10 | 1.3452 | 0.0207 | IL-18R1 | −1.668 | 0.0121 |
| CCL11 | 1.3225 | 0.0111 | IL-1ra | −1.6559 | 0.0334 |
| LY75 | 1.2722 | 0.0376 | CLEC7A | −1.6558 | 0.0316 |
| DKKL1 | 1.2291 | 0.0499 | SIGLEC7 | −1.5857 | 0.0148 |
|  |  |  | COL4A1 | −1.5794 | 0.0156 |
|  |  |  | TLR3 | −1.5753 | 0.0412 |
|  |  |  | PD-L1 | −1.5245 | 0.0139 |
|  |  |  | IL-18BP | −1.4932 | 0.0342 |
|  |  |  | PILRA | −1.4815 | 0.0341 |
|  |  |  | CCL15 | −1.4614 | 0.0279 |
|  |  |  | uPA | −1.4223 | 0.0314 |
|  |  |  | DLL1 | −1.2888 | 0.0194 |
|  |  |  | THBS2 | −1.2178 | 0.004 |
|  |  |  | SPON2 | −1.1748 | 0.0105 |

Example 2: Characterization of Protein Expression During the Course of Treatment Plasma samples were collected from individuals enrolled in the clinical study of Example 1 at baseline and at day 28.

Table 5 lists proteins that were significantly modulated by treatment between baseline and day 28. Table 6 lists proteins that were stably expressed throughout the study and were not significantly modulated by treatment between baseline and day 28.

Table 5 identifies proteins that changed in complete responders between day 1 (baseline) to day 28. Fold change in this example represents the change of a protein level between day 1 (baseline) versus day 28. A paired t test was used to compare the relative change between level of a protein between day 1 and day 28. Table 5 identifies biomarkers of therapeutic response.

TABLE 5

Proteins Significantly Modulated in Complete Responders Between Baseline and Day 28

| Increased Expression from Baseline to Day 28 | | | Decreased Expression from Baseline to Day 28 | | |
|---|---|---|---|---|---|
| Protein Change | Fold | Raw P Value | Protein | Fold Change | Raw P Value |
| GCG | 2.3961 | 0.0168 | PDGF subunit B | -2.7388 | 0.001 |
| GAL | 2.0603 | 0.0052 | | | |
| THPO | 1.8262 | 0.0094 | FKBP1B | -2.5654 | 0.0036 |
| FAM3B | 1.7937 | 0.0011 | ITGB1BP2 | -2.1159 | 0.0047 |
| CNDP1 | 1.5692 | 0.0134 | CD69 | -2.1102 | 0.0016 |
| CCL11 | 1.401 | 0.0013 | ANG-1 | -2.0923 | 0.0062 |
| SERP1NA5 | 1.3313 | 0.0089 | PVALB | -2.0632 | 0.0145 |
| DKKL1 | 1.2705 | 0.0014 | CD40-L | -1.9741 | 0.0256 |
| NCAM1 | 1.2481 | 0.0284 | CCL5 | -1.9502 | 0.0065 |
| SPON2 | 1.1003 | 0.0106 | HS3ST3B1 | -1.9303 | 0.0193 |
| THBS2 | 1.0834 | 0.0051 | MBL2 | -1.9284 | 0.0215 |
| GCG | 2.3961 | 0.0168 | CLEC7A | -1.8985 | 0.0006 |
| GAL | 2.0603 | 0.0052 | APP | -1.8356 | 0.0053 |
| THPO | 1.8262 | 0.0094 | PDGF subunit A | -1.7507 | 0.0068 |
| FAM3B | 1.7937 | 0.0011 | | | |
| CNDP1 | 1.5692 | 0.0134 | DCTN2 | -1.6367 | 0.0274 |
| CCL11 | 1.401 | 0.0013 | SLAMF8 | -1.5899 | 0.0244 |
| SERPINA5 | 1.3313 | 0.0089 | VAMP5 | -1.5851 | 0.0053 |
| DKKL1 | 1.2705 | 0.0014 | SIGLEC10 | -1.4859 | 0.0226 |
| NCAM1 | 1.2481 | 0.0284 | CLM-1 | -1.4729 | 0.0319 |
| SPON2 | 1.1003 | 0.0106 | DSC2 | -1.4423 | 0.0017 |
| THBS2 | 1.0834 | 0.0051 | HAVCR2 | -1.3876 | 0.0126 |
| | | | SIRPB1 | -1.3861 | 0.0072 |
| | | | COL4A1 | -1.3412 | 0.0369 |
| | | | PILRA | -1.2552 | 0.0282 |
| | | | LY75 | -1.2217 | 0.024 |

Table 6 identifies proteins that did not modulate in complete responders between baseline (day 1) and day 28. Therefore, these proteins are designated as baseline predictive biomarkers.

TABLE 6

Proteins Stably Expressed in Complete Responders Between Day 1 and Day 28

| Proteins Increased But Not Significant | | | Proteins Decreased But Not Significant | | |
|---|---|---|---|---|---|
| Protein | Fold Change | Raw P Value | Protein | Fold Change | Raw P Value |
| IL6 | 1.7545 | 0.1382 | MANF | -1.6753 | 0.0584 |
| HAOX1 | 1.7169 | 0.0995 | SRC | -1.6394 | 0.0535 |
| IGFBP-1 | 1.6812 | 0.1999 | TWEAK | -1.4741 | 0.1325 |
| IL6 | 1.6701 | 0.1579 | CR2 | -1.4025 | 0.0966 |
| IL6 | 1.5995 | 0.1953 | SIGLEC1 | -1.3628 | 0.0991 |
| ENPP7 | 1.5432 | 0.1385 | TNF-R2 | -1.3591 | 0.0931 |
| IL6 | 1.5407 | 0.2577 | TNFRSF6B | -1.3442 | 0.1025 |
| SCF | 1.5147 | 0.0799 | AHCY | -1.3275 | 0.0854 |
| SCGB3A1 | 1.5084 | 0.0863 | CRTAM | -1.3192 | 0.3574 |

TABLE 6-continued

Proteins Stably Expressed in Complete Responders Between Day 1 and Day 28

| Proteins Increased But Not Significant | | | Proteins Decreased But Not Significant | | |
|---|---|---|---|---|---|
| Protein | Fold Change | Raw P Value | Protein | Fold Change | Raw P Value |
| SCF | 1.4346 | 0.0961 | CKAP4 | -1.2761 | 0.1239 |
| SCF | 1.3988 | 0.1184 | CA5A | -1.267 | 0.3739 |
| PON3 | 1.3708 | 0.0631 | CALCA | -1.2236 | 0.6545 |
| MCP-3 | 1.3171 | 0.2406 | IL-1ra | -1.2159 | 0.3242 |
| IL8 | 1.286 | 0.2913 | TNFRSF9 | -1.2128 | 0.2866 |
| NINJ1 | 1.239 | 0.0994 | DDAH1 | -1.1849 | 0.2464 |
| NTRK3 | 1.2351 | 0.0846 | HSP 27 | -1.1778 | 0.1094 |
| CNTN1 | 1.2158 | 0.1831 | SAA4 | -1.1593 | 0.5157 |
| ACE2 | 1.2118 | 0.4374 | PFKM | -1.1575 | 0.2464 |
| IGFBP3 | 1.1814 | 0.3669 | TIMP4 | -1.1371 | 0.2962 |
| GH | 1.1727 | 0.676 | LEP | -1.1316 | 0.6995 |
| CCL15 | 1.1726 | 0.2308 | IL-18BP | -1.1268 | 0.5792 |
| SULT2A1 | 1.169 | 0.6268 | CDSN | -1.1137 | 0.2888 |
| uPA | 1.1545 | 0.1665 | PD-L1 | -1.0969 | 0.4905 |
| FOSB | 1.1542 | 0.1953 | IL-18R1 | -1.0806 | 0.2996 |
| PLXNB1 | 1.1495 | 0.1726 | N2DL-2 | -1.0683 | 0.695 |
| PREB | 1.1356 | 0.1311 | CCL19 | -1.061 | 0.8598 |
| CXCL10 | 1.133 | 0.805 | ALDH3A1 | -1.0553 | 0.5588 |
| PROC | 1.1313 | 0.4097 | U-PAR | -1.054 | 0.6793 |
| TNFRSF4 | 1.1251 | 0.4331 | SPINK1 | -1.038 | 0.8215 |
| KYNU | 1.1183 | 0.5652 | TNFRSF10A | -1.0214 | 0.7961 |
| AMBP | 1.1176 | 0.3079 | CTSL1 | -1.0209 | 0.9115 |
| VEGFD | 1.1116 | 0.1912 | F11 | -1.0199 | 0.8362 |
| DLL1 | 1.1055 | 0.2106 | SIGLEC7 | -1.015 | 0.9064 |
| NCAN | 1.0964 | 0.0631 | KRT19 | -1.0136 | 0.9496 |
| TN-R | 1.0934 | 0.5608 | IL12RB1 | -1.0129 | 0.9484 |
| GALNT10 | 1.064 | 0.5285 | CRISP2 | -1.0113 | 0.8654 |
| NFATC3 | 1.0637 | 0.7243 | TNFRSF10A | -1.0093 | 0.9187 |
| CDCP1 | 1.0579 | 0.7832 | ALDH1A1 | -1.0018 | 0.9927 |
| HSD11B1 | 1.0468 | 0.7981 | | | |
| APOM | 1.0434 | 0.8235 | | | |
| ENTPD2 | 1.0429 | 0.3761 | | | |
| TLR3 | 1.035 | 0.5615 | | | |
| GCP5 | 1.0249 | 0.7675 | | | |
| GZMB | 1.0134 | 0.9703 | | | |
| CD74 | 1.0118 | 0.8996 | | | |

Example 3: Identification of Proteins that do or do not Correlate with REG3α, TNFR1, and ST2

Several inflammatory mediators have been identified and associated with increased risk of acute GvHD in steroid treated subjects that have received a hematopoietic stem cell transplant. These inflammatory mediators include REG3α, TNFR1, and ST2 (Hartwell et al., "An early-biomarker algorithm predicts lethal graft-versus-host disease and survival, JCI Insight, 2(3):e89798). Using plasma samples from subjects enrolled in the clinical study of Example 1, proteins were evaluated for their correlation with REG3α, TNFR1, and ST2 levels at baseline. Correlation refers to potential biomarkers showing similar change or distribution as REG3α, TNFR1, and ST2. Table 7 identifies proteins that significantly (p<0.1) correlate with REG3α, TNFR1, and ST2 at baseline. Table 8 identifies proteins that do not significantly (p>0.1) correlate with REG3α, TNFR1, and ST2 at baseline.

TABLE 7

Proteins that Significantly Correlate with REG3α, TNFR1, and ST2

| Proteins that correlate with REG3A | | | Proteins that correlate with TNFR1 | | | Proteins that correlate with ST2 | | |
| --- | --- | --- | --- | --- | --- | --- | --- | --- |
| Protein | Correlation | P Value | Protein | Correlation | P Value | Protein | Correlation | P Value |
| CD74 | 0.9158 | 0.0002 | FAM3B | 0.7439 | 0.0136 | HAOX1 | 0.7127 | 0.0207 |
| CALCA | 0.8675 | 0.0011 | TIMP4 | 0.7076 | 0.0221 | VAMP5 | 0.5498 | 0.0996 |
| N2DL-2 | 0.8435 | 0.0022 | AMBP | 0.6938 | 0.0261 | TLR3 | −0.7273 | 0.0171 |
| SPINK1 | 0.8116 | 0.0044 | GCG | 0.6566 | 0.0392 | HS3ST3B1 | −0.6144 | 0.0588 |
| CKAP4 | 0.7651 | 0.0099 | MANF | 0.621 | 0.0553 | NCAM1 | −0.6032 | 0.0648 |
| NFATC3 | 0.7568 | 0.0113 | VAMP5 | 0.6094 | 0.0614 | SCGB3A1 | −0.5909 | 0.072 |
| SLAMF8 | 0.7158 | 0.0199 | LEP | 0.5986 | 0.0675 | | | |
| DSC2 | 0.7037 | 0.0231 | IGFBP-1 | 0.5712 | 0.0846 | | | |
| PLXNB1 | 0.701 | 0.0239 | F11 | 0.5683 | 0.0865 | | | |
| VEGFD | 0.6982 | 0.0247 | PD-L1 | 0.5512 | 0.0987 | | | |
| HAVCR2 | 0.6898 | 0.0273 | ENPP7 | −0.5962 | 0.0689 | | | |
| KRT19 | 0.6864 | 0.0284 | | | | | | |
| PILRA | 0.6774 | 0.0314 | | | | | | |
| IL-18BP | 0.659 | 0.0382 | | | | | | |
| TNF-R2 | 0.6456 | 0.0438 | | | | | | |
| CDCP1 | 0.6439 | 0.0445 | | | | | | |
| U-PAR | 0.6349 | 0.0486 | | | | | | |
| CLEC7A | 0.6315 | 0.0502 | | | | | | |
| CCL15 | 0.6276 | 0.0521 | | | | | | |
| IL-1ra | 0.6237 | 0.054 | | | | | | |
| SAA4 | 0.607 | 0.0627 | | | | | | |
| IL-18R1 | 0.6039 | 0.0645 | | | | | | |
| TNFRSF9 | 0.5953 | 0.0694 | | | | | | |
| CLM-1 | 0.5886 | 0.0734 | | | | | | |
| ITGB1BP2 | 0.5683 | 0.0865 | | | | | | |
| APOM | 0.5667 | 0.0876 | | | | | | |
| IL12RB1 | 0.5528 | 0.0975 | | | | | | |
| CRISP2 | −0.6654 | 0.0357 | | | | | | |

TABLE 8

Proteins that do not Significantly Correlate with REG3α, TNFR1, and ST2

| Proteins that do not correlate with REG3A | | | Proteins that do not correlate with TNFR1 | | | Proteins that do not correlate with ST2 | | |
| --- | --- | --- | --- | --- | --- | --- | --- | --- |
| Protein | Correlation | P Value | Protein | Correlation | P Value | Protein | Correlation | P Value |
| CDSN | 0.5421 | 0.1055 | SCF | 0.5327 | 0.1129 | SRC | 0.5154 | 0.1273 |
| SIRPB1 | 0.5295 | 0.1155 | SCF | 0.5302 | 0.1149 | FOSB | 0.4886 | 0.1519 |
| TNFRSF4 | 0.5048 | 0.1368 | CCL15 | 0.5161 | 0.1267 | SULT2A1 | 0.4758 | 0.1645 |
| CCL5 | 0.5026 | 0.1387 | DCTN2 | 0.5131 | 0.1293 | KYNU | 0.4712 | 0.1692 |
| SIGLEC10 | 0.5024 | 0.1389 | DDAH1 | 0.5114 | 0.1309 | SIGLEC10 | 0.4656 | 0.1751 |
| SIGLEC7 | 0.4969 | 0.144 | DLL1 | 0.5068 | 0.1349 | CTSL1 | 0.4628 | 0.1781 |
| MANF | 0.4955 | 0.1453 | SIRPB1 | 0.5053 | 0.1363 | CA5A | 0.4588 | 0.1823 |
| SIGLEC1 | 0.4867 | 0.1537 | COL4A1 | 0.5019 | 0.1393 | COL4A1 | 0.4535 | 0.188 |
| APP | 0.4833 | 0.1571 | SRC | 0.4937 | 0.147 | MANF | 0.4374 | 0.2062 |
| CTSL1 | 0.4797 | 0.1606 | TNFRSF4 | 0.4851 | 0.1553 | MCP-3 | 0.4227 | 0.2236 |
| PDGF subunit A | 0.4733 | 0.1671 | ALDH3A1 | 0.4831 | 0.1572 | FAM3B | 0.4091 | 0.2405 |
| IGFBP-1 | 0.4368 | 0.2069 | SULT2A1 | 0.4796 | 0.1607 | GCG | 0.4017 | 0.2499 |
| SPON2 | 0.4365 | 0.2072 | SERPINA5 | 0.4683 | 0.1723 | CCL15 | 0.3789 | 0.2802 |
| SRC | 0.4349 | 0.209 | CLEC7A | 0.4674 | 0.1731 | DDAH1 | 0.3768 | 0.2832 |
| GCP5 | 0.4261 | 0.2196 | TNF-R2 | 0.4671 | 0.1734 | AHCY | 0.3758 | 0.2845 |
| CRTAM | 0.42 | 0.2269 | CNTN1 | 0.4106 | 0.2386 | PD-L1 | 0.3545 | 0.3149 |
| TLR3 | 0.4143 | 0.2339 | FKBP1B | 0.404 | 0.247 | SPON2 | 0.3342 | 0.3452 |
| PD-L1 | 0.4068 | 0.2434 | CLM-1 | 0.39 | 0.2652 | KRT19 | 0.3166 | 0.3727 |
| MCP-3 | 0.4 | 0.252 | SIGLEC1 | 0.3765 | 0.2835 | CRTAM | 0.3123 | 0.3797 |
| CXCL10 | 0.3944 | 0.2594 | SCF | 0.3748 | 0.2858 | ALDH1A1 | 0.3079 | 0.3868 |
| IL8 | 0.3778 | 0.2818 | MBL2 | 0.3728 | 0.2887 | ITGB1BP2 | 0.2858 | 0.4233 |
| CNTN1 | 0.3588 | 0.3086 | GALNT10 | 0.3583 | 0.3093 | NFATC3 | 0.2854 | 0.4242 |
| PDGF subunit B | 0.3581 | 0.3096 | TNFRSF9 | 0.351 | 0.3201 | IL6 | 0.2821 | 0.4298 |
| FKBP1B | 0.3529 | 0.3172 | PILRA | 0.3496 | 0.322 | ALDH3A1 | 0.2716 | 0.4477 |
| CD69 | 0.3487 | 0.3235 | CD40-L | 0.3423 | 0.3329 | ACE2 | 0.2692 | 0.452 |
| ENPP7 | 0.3255 | 0.3587 | IL-18BP | 0.3311 | 0.3501 | IL8 | 0.2651 | 0.4591 |
| LY75 | 0.3251 | 0.3594 | GCP5 | 0.3298 | 0.352 | IL6 | 0.2604 | 0.4675 |
| uPA | 0.3224 | 0.3636 | CD69 | 0.3237 | 0.3616 | DCTN2 | 0.2494 | 0.4871 |
| DCTN2 | 0.3165 | 0.373 | U-PAR | 0.3234 | 0.362 | SPINK1 | 0.2493 | 0.4872 |
| VAMP5 | 0.3128 | 0.3788 | TWEAK | 0.3205 | 0.3666 | IL6 | 0.2411 | 0.5022 |

TABLE 8-continued

Proteins that do not Significantly Correlate with REG3α, TNFR1, and ST2

| Proteins that do not correlate with REG3A | | | Proteins that do not correlate with TNFR1 | | | Proteins that do not correlate with ST2 | | |
|---|---|---|---|---|---|---|---|---|
| Protein | Correlation | P Value | Protein | Correlation | P Value | Protein | Correlation | P Value |
| ANG-1 | 0.308 | 0.3866 | DSC2 | 0.3192 | 0.3687 | CD69 | 0.2244 | 0.533 |
| CD40-L | 0.3077 | 0.3871 | HSD11B1 | 0.3159 | 0.374 | VEGFD | 0.2227 | 0.5363 |
| TIMP4 | 0.302 | 0.3964 | HSP 27 | 0.2988 | 0.4018 | PLXNB1 | 0.222 | 0.5377 |
| CA5A | 0.2969 | 0.4049 | NTRK3 | 0.2821 | 0.4297 | SIRPB1 | 0.2111 | 0.5582 |
| TNFRSF6B | 0.2891 | 0.4179 | ITGB1BP2 | 0.2648 | 0.4597 | MBL2 | 0.2088 | 0.5627 |
| GCG | 0.2604 | 0.4675 | CA5A | 0.2477 | 0.4901 | TIMP4 | 0.2085 | 0.5633 |
| DDAH1 | 0.2571 | 0.4733 | SPINK1 | 0.2403 | 0.5037 | IL6 | 0.2063 | 0.5675 |
| KYNU | 0.2506 | 0.485 | FOSB | 0.2371 | 0.5096 | SIGLEC7 | 0.2015 | 0.5767 |
| GH | 0.2433 | 0.4982 | IL12RB1 | 0.22 | 0.5414 | TNF-R2 | 0.1932 | 0.5928 |
| IL6 | 0.2424 | 0.4998 | LY75 | 0.1997 | 0.5802 | FKBP1B | 0.1822 | 0.6143 |
| MBL2 | 0.2384 | 0.5071 | CCL19 | 0.195 | 0.5893 | CNDP1 | 0.1782 | 0.6223 |
| TNFRSF10A | 0.2273 | 0.5277 | ENTPD2 | 0.1913 | 0.5964 | GAL | 0.1763 | 0.6262 |
| ACE2 | 0.222 | 0.5377 | APOM | 0.1908 | 0.5975 | DLL1 | 0.1665 | 0.6458 |
| IL6 | 0.2185 | 0.5442 | SPON2 | 0.1893 | 0.6004 | DSC2 | 0.1661 | 0.6464 |
| TNFRSF10A | 0.2081 | 0.564 | CKAP4 | 0.1813 | 0.6162 | SIGLEC1 | 0.1642 | 0.6503 |
| IGFBP3 | 0.2074 | 0.5653 | CCL5 | 0.1799 | 0.619 | CLEC7A | 0.161 | 0.6568 |
| IL6 | 0.1987 | 0.5821 | PROC | 0.1767 | 0.6254 | HAVCR2 | 0.1598 | 0.6592 |
| HSP 27 | 0.191 | 0.5972 | CTSL1 | 0.1592 | 0.6604 | U-PAR | 0.1579 | 0.6632 |
| ALDH3A1 | 0.1869 | 0.6052 | HAVCR2 | 0.1576 | 0.6636 | CALCA | 0.1474 | 0.6844 |
| CNDP1 | 0.1755 | 0.6276 | GAL | 0.1471 | 0.6851 | CRISP2 | 0.1461 | 0.6872 |
| IL6 | 0.1694 | 0.64 | PON3 | 0.1353 | 0.7094 | PILRA | 0.1439 | 0.6916 |
| GZMB | 0.1604 | 0.658 | TNFRSF10A | 0.1328 | 0.7146 | PROC | 0.1351 | 0.7098 |
| SCGB3A1 | 0.1596 | 0.6597 | CDSN | 0.1261 | 0.7286 | NCAN | 0.1245 | 0.7318 |
| CCL19 | 0.1423 | 0.6949 | TNFRSF6B | 0.125 | 0.7308 | PDGF subunit A | 0.124 | 0.7328 |
| ALDH1A1 | 0.1224 | 0.7363 | TNFRSF10A | 0.1009 | 0.7815 | IL-1ra | 0.1166 | 0.7483 |
| FOSB | 0.1068 | 0.769 | CRISP2 | 0.0895 | 0.8057 | LEP | 0.1156 | 0.7504 |
| HAOX1 | 0.0985 | 0.7865 | KYNU | 0.0889 | 0.8071 | GCP5 | 0.095 | 0.794 |
| AHCY | 0.0951 | 0.7938 | PDGF subunit B | 0.084 | 0.8176 | SLAMF8 | 0.0876 | 0.8099 |
| NTRK3 | 0.0842 | 0.8171 | ANG-1 | 0.079 | 0.8284 | CD74 | 0.0855 | 0.8142 |
| FAM3B | 0.0842 | 0.8172 | CRTAM | 0.0665 | 0.8552 | ENPP7 | 0.0743 | 0.8384 |
| COL4A1 | 0.0703 | 0.8469 | MCP-3 | 0.0537 | 0.8828 | IGFBP-1 | 0.0727 | 0.8419 |
| THPO | 0.0603 | 0.8685 | THBS2 | 0.0536 | 0.8831 | CD40-L | 0.0692 | 0.8494 |
| PROC | 0.0564 | 0.877 | SIGLEC7 | 0.0485 | 0.8942 | TNFRSF10A | 0.0606 | 0.8679 |
| NCAM1 | 0.0319 | 0.9304 | CR2 | 0.0378 | 0.9175 | F11 | 0.0544 | 0.8813 |
| NCAN | 0.0227 | 0.9504 | SAA4 | 0.0183 | 0.96 | uPA | 0.0506 | 0.8896 |
| PON3 | 0.0187 | 0.9591 | PREB | 0 | 1 | GALNT10 | 0.0387 | 0.9154 |
| DLL1 | 0.0146 | 0.9681 | NINJ1 | 0 | 1 | THBS2 | 0.0387 | 0.9155 |
| NINJ1 | 0 | 1 | THPO | −0.0005 | 0.9989 | CDCP1 | 0.0266 | 0.9418 |
| PREB | 0 | 1 | PLXNB1 | −0.0028 | 0.9938 | PDGF subunit B | 0.0201 | 0.956 |
| SULT2A1 | −0.0321 | 0.9298 | NFATC3 | −0.0033 | 0.9928 | SCF | 0.004 | 0.9913 |
| TN-R | −0.0585 | 0.8724 | PDGF subunit A | −0.01 | 0.9781 | NTRK3 | 0.0026 | 0.9942 |
| AMBP | −0.0823 | 0.8211 | N2DL-2 | −0.0164 | 0.9641 | SCF | 0.0018 | 0.9961 |
| GALNT10 | −0.081 | 0.8194 | HAOX1 | −0.0276 | 0.9396 | CCL5 | 0.0015 | 0.9968 |
| TWEAK | −0.1065 | 0.7697 | GZMB | −0.0298 | 0.9349 | PREB | 0 | 1 |
| DKKL1 | −0.1125 | 0.7569 | uPA | −0.03 | 0.9343 | NINJ1 | 0 | 1 |
| PVALB | −0.118 | 0.7454 | SLAMF8 | −0.0371 | 0.919 | TNFRSF10A | −0.0047 | 0.9896 |
| PFKM | −0.1796 | 0.6196 | CDCP1 | −0.0431 | 0.9058 | TNFRSF9 | −0.0047 | 0.9896 |
| HSD11B1 | −0.1829 | 0.6131 | PVALB | −0.0674 | 0.8533 | CLM-1 | −0.0066 | 0.9855 |
| ENTPD2 | −0.1832 | 0.6124 | CXCL10 | −0.0675 | 0.853 | CDSN | −0.0137 | 0.97 |
| HS3ST3B1 | −0.2478 | 0.49 | SIGLEC10 | −0.1138 | 0.7543 | IL-18BP | −0.0184 | 0.9598 |
| F11 | −0.249 | 0.4879 | IL-1ra | −0.1167 | 0.7481 | CCL19 | −0.0194 | 0.9576 |
| CR2 | −0.2631 | 0.4626 | IGFBP3 | −0.1316 | 0.7171 | N2DL-2 | −0.0203 | 0.9556 |
| GAL | −0.2958 | 0.4067 | CCL11 | −0.1433 | 0.6928 | TNFRSF4 | −0.0231 | 0.9495 |
| SCF | −0.3195 | 0.3681 | CALCA | −0.1562 | 0.6666 | SCF | −0.0345 | 0.9246 |
| SCF | −0.3198 | 0.3677 | NCAN | −0.1632 | 0.6523 | HSD11B1 | −0.0653 | 0.8578 |
| SERPINA5 | −0.3358 | 0.3427 | TN-R | −0.1766 | 0.6254 | APOM | −0.0674 | 0.8532 |
| SCF | −0.3513 | 0.3196 | PFKM | −0.1914 | 0.5963 | CCL11 | −0.0699 | 0.8479 |
| THBS2 | −0.3725 | 0.2892 | DKKL1 | −0.2137 | 0.5532 | GZMB | −0.0739 | 0.8393 |
| LEP | −0.3739 | 0.2872 | CD74 | −0.2144 | 0.5519 | CKAP4 | −0.0951 | 0.7938 |
| CCL11 | −0.4076 | 0.2423 | ALDH1A1 | −0.2245 | 0.5329 | AMBP | −0.122 | 0.7371 |
| | | | SCGB3A1 | −0.2297 | 0.5233 | THPO | −0.1323 | 0.7156 |
| | | | NCAM1 | −0.2349 | 0.5135 | LY75 | −0.1404 | 0.6989 |
| | | | IL6 | −0.249 | 0.4878 | IL-18R1 | −0.1526 | 0.6738 |
| | | | CNDP1 | −0.2571 | 0.4734 | ENTPD2 | −0.1561 | 0.6667 |
| | | | IL6 | −0.2641 | 0.4609 | ANG-1 | −0.1586 | 0.6618 |
| | | | IL6 | −0.2755 | 0.441 | APP | −0.1633 | 0.6521 |
| | | | KRT19 | −0.278 | 0.4368 | IL12RB1 | −0.1745 | 0.6296 |
| | | | ACE2 | −0.2926 | 0.4119 | SAA4 | −0.1783 | 0.6221 |
| | | | IL-18R1 | −0.3026 | 0.3954 | SERPINA5 | −0.1971 | 0.5852 |

TABLE 8-continued

Proteins that do not Significantly Correlate with REG3α, TNFR1, and ST2

| Proteins that do not correlate with REG3A | | | Proteins that do not correlate with TNFR1 | | | Proteins that do not correlate with ST2 | | |
|---|---|---|---|---|---|---|---|---|
| Protein | Correlation | P Value | Protein | Correlation | P Value | Protein | Correlation | P Value |
| | | | APP | −0.3215 | 0.365 | HSP 27 | −0.2018 | 0.5762 |
| | | | TLR3 | −0.3408 | 0.3352 | TN-R | −0.204 | 0.5719 |
| | | | AHCY | −0.353 | 0.317 | PFKM | −0.2317 | 0.5196 |
| | | | IL6 | −0.3819 | 0.2762 | TNFRSF6B | −0.2566 | 0.4742 |
| | | | VEGFD | −0.4069 | 0.2432 | PON3 | −0.2767 | 0.4389 |
| | | | IL8 | −0.4509 | 0.1909 | IGFBP3 | −0.2965 | 0.4054 |
| | | | HS3ST3B1 | −0.4519 | 0.1898 | PVALB | −0.306 | 0.3899 |
| | | | GH | −0.5459 | 0.1026 | DKKL1 | −0.3744 | 0.2865 |
| | | | | | | CNTN1 | −0.3974 | 0.2555 |
| | | | | | | CXCL10 | −0.4139 | 0.2344 |
| | | | | | | GH | −0.4141 | 0.2342 |
| | | | | | | TWEAK | −0.471 | 0.1695 |
| | | | | | | CR2 | −0.5445 | 0.1036 |

Example 4: Selection of Proteins Capable of Predicting Positive Therapeutic Response with JAK Inhibition in GvHD Data from the previous examples identified several proteins at baseline that predict a positive therapeutic response, as evidenced by classification as CR at day 28. Proteins listed in (but not limited to) Table 9 were found to be: (1) differentially expressed between the CR and PD/Death treatment groups; (2) stable between baseline and day 28; and (3) not correlated with REG3α, TNFR1, and ST2.

TABLE 9

Proteins Differentially Expressed Between the CR and PD/Death Treatment Groups, Stable Between Baseline and Day 28, and not Correlated with REG3α, TNFR1, and ST2

| Proteins Increased in CR | | | Proteins Decreased in CR | | |
|---|---|---|---|---|---|
| Protein | Fold Change | Raw P Value | Protein | Fold Change | Raw P Value |
| PON3 | 3.9728 | 0.0005 | MCP-3 | −6.0399 | 0.0004 |
| SCF | 3.0746 | 0.003 | CA5A | −4.5712 | 0.0085 |
| SCF | 2.9526 | 0.0026 | IL8 | −4.0642 | 0.0216 |
| SCF | 2.9112 | 0.003 | CXCL10 | −3.8124 | 0.0065 |
| GH | 2.4121 | 0.0155 | SULT2A1 | −3.5143 | 0.0149 |
| SRC | 2.1146 | 0.036 | IL6 | −3.4705 | 0.0258 |
| CR2 | 2.0089 | 0.0197 | CCL19 | −2.9578 | 0.0041 |
| PFKM | 1.9756 | 8.93E−05 | CTSL1 | −2.9056 | 0.0018 |
| HSD11B1 | 1.8131 | 0.0173 | ACE2 | −2.8742 | 0.0054 |
| IGFBP3 | 1.7304 | 0.0287 | IL6 | −2.8377 | 0.0121 |
| CDSN | 1.7055 | 0.0227 | CRTAM | −2.6741 | 0.0312 |
| TWEAK | 1.6972 | 0.0338 | ALDH1A1 | −2.6667 | 0.0141 |
| TN-R | 1.653 | 0.0321 | IL6 | −2.5189 | 0.0141 |
| CNTN1 | 1.5831 | 0.0275 | GZMB | −2.307 | 0.0289 |
| GCP5 | 1.5583 | 0.0383 | TNFRSF6B | −2.3053 | 0.0037 |
| PROC | 1.514 | 0.0289 | KYNU | −2.2368 | 0.0217 |
| NCAN | 1.4147 | 0.0259 | FOSB | −2.2367 | 0.0169 |
| NTRK3 | 1.3885 | 0.0255 | ALDH3A1 | −2.1808 | 0.0104 |
| HSP 27 | 1.3522 | 0.0446 | DDAH1 | −2.036 | 0.0289 |
| GALNT10 | 1.3452 | 0.0207 | NINJA | −1.9125 | 0.0043 |
| | | | ENTPD2 | −1.8643 | 0.0227 |
| | | | SIGLEC1 | −1.8208 | 0.0229 |
| | | | PREB | −1.8178 | 0.0327 |
| | | | AHCY | −1.7883 | 0.043 |
| | | | TNFRSF10A | −1.7188 | 0.0133 |
| | | | TNFRSF4 | −1.677 | 0.0423 |
| | | | SIGLEC7 | −1.5857 | 0.0148 |
| | | | uPA | −1.4223 | 0.0314 |
| | | | DLL1 | −1.2888 | 0.0194 |

Using a more stringent cutoff of 2 (absolute number), the number of predictive proteins was further reduced (Table 10).

TABLE 10

Selected Proteins Capable of Predicting Positive Therapeutic Response to JAK Inhibition in GvHD

| Protein | Fold Change CR vs PD/Death | Raw P Value |
|---|---|---|
| PON3 | 3.9728 | 0.0005 |
| SCF | 3.0746 | 0.003 |
| SCF | 2.9526 | 0.0026 |
| SCF | 2.9112 | 0.003 |
| GH | 2.4121 | 0.0155 |
| SRC | 2.1146 | 0.036 |
| CR2 | 2.0089 | 0.0197 |
| MCP-3 | −6.0399 | 0.0004 |
| CA5A | −4.5712 | 0.0085 |
| IL8 | −4.0642 | 0.0216 |
| CXCL10 | −3.8124 | 0.0065 |
| IL6 | −3.4705 | 0.0258 |
| CCL19 | −2.9578 | 0.0041 |
| CTSL1 | −2.9056 | 0.0018 |
| ACE2 | −2.8742 | 0.0054 |
| IL6 | −2.8377 | 0.0121 |
| ALDH1A1 | −2.6667 | 0.0141 |
| IL6 | −2.5189 | 0.0141 |
| TNFRSF6B | −2.3053 | 0.0037 |
| KYNU | −2.2368 | 0.0217 |
| FOSB | −2.2367 | 0.0169 |
| ALDH3A1 | −2.1808 | 0.0104 |
| DDAH1 | −2.036 | 0.0289 |

Example 5: Identification of Proteins Differentially Expressed in Patients with Acute Graft-Versus-Host Disease that are Complete Responders to Treatment with Itacitinib The combination of itacitinib with corticosteroids was evaluated in a parallel-cohort phase 1 trial and improved overall responses for both steroid naïve and refractory aGvHD patients. A broad proteomic analysis identified predictive, prognostic, and pharmacodynamic biomarkers of response to the combination treatment.

Ten steroid-naive and eighteen steroid-refractory subjects with aGvHD were enrolled in the clinical trial. Plasma samples were collected from all 28 subjects prior to treatment (screening/baseline) and at day 28 following treatment. All subjects provided written consent prior to enrollment and sample collection. Based on the Center for International Blood and Marrow Transplant Research (CIBMTR) response criteria at day 28, subjects were separated into responders and non-responders. Responders included complete responders (CR; n=10), very good partial responders (VGPR; n=1), and partial responders (PR; n=8). Non-responders included mixed responders (n=2) and progressive disease/death (PD/Death; n=7).

Subjects were treated with corticosteroids in combination with either 200 mg (N=14) or 300 mg (N=14) of itacitinib once daily (QD). Clinical response was not significantly different between the two itacitinib doses; therefore, data from both cohorts were combined. Due to the limited sample size, steroid-naive (N=10) and steroid-refractory (N=18) patients were combined for further analysis. Broad proteomic analysis of over 1000 proteins was conducted by OLINK Proteomics (Watertown, Mass.) using a proximity extension assay as described by the manufacturer. Data are presented as normalized protein expression (NPX) in log 2 scale. Statistical differences were evaluated using unpaired and paired t tests, one-way analysis of covariance (ANOVA), and Pearson Correlation. Significance was conferred when $P<0.05$.

Proteins were identified based on significant differences between the complete responder and progressive disease/death cohorts at baseline that achieved at least a 1.2 fold change between cohorts. See Table 11. Because some patients were re-classified based on their day 28 response, Table 11 represents an updated list of proteins originally shown in Example 1, Table 4.

A total of 146 differentially expressed proteins between the CR and PD/Death groups of subjects were identified. Fifty-seven proteins were increased and 89 proteins were decreased in CR compared to PD/Death. See Table 11.

TABLE 11

Differentially Expressed Proteins at Baseline in the Plasma of Complete Responders Compared to the Progressive Disease/Death Groups

| Up-Regulated in CR Compared to PD/Death | | | Down-Regulated in CR Compared to PD/Death | | |
|---|---|---|---|---|---|
| Protein | Fold Change | Raw P Value | Protein | Fold Change | Raw P Value |
| CCL17 | 6.4545 | 0.0014 | MCP-3 | −7.865 | 0.000012941 |
| PON3 | 4.8594 | 0.0005 | HAOX1 | −7.846 | 0.0027 |
| LEP | 4.402 | 0.0191 | CA5A | −7.4693 | 0.001 |
| GCG | 3.904 | 0.0031 | CALCA | −5.4107 | 0.0339 |
| MBL2 | 3.7419 | 0.0014 | IL8 | −5.0031 | 0.0006 |
| SCF | 3.5978 | 0.0006 | AREG | −4.8443 | 0.0377 |
| SCF | 3.5041 | 0.0008 | SULT2A1 | −4.7009 | 0.0062 |
| SCF | 3.2594 | 0.0024 | VAMP5 | −4.3186 | 0.0064 |
| SCGB3A1 | 3.1352 | 0.0051 | SPINK1 | −4.2632 | 0.0171 |
| GAL | 3.0034 | 0.0179 | SIGLEC10 | −3.8434 | 0.0002 |
| FAM3B | 2.8141 | 0.0165 | ENPP7 | −3.804 | 0.032 |
| THPO | 2.7391 | 0.007 | ACE2 | −3.7433 | 0.0021 |
| GH | 2.6866 | 0.0085 | CTSL1 | −3.7378 | 0.0004 |
| PVALB | 2.6266 | 0.0194 | PRSS2 | −3.6787 | 0.0454 |
| ANG-1 | 2.3398 | 0.0462 | CXCL10 | −3.5343 | 0.0192 |
| GDF-8 | 2.2804 | 0.0377 | NEP | −3.4607 | 0.033 |
| EN-RAGE | 2.2642 | 0.0432 | MFGE8 | −3.4384 | 0.014 |
| CRISP2 | 2.2475 | 0.0149 | KRT19 | −3.2722 | 0.0153 |
| CR2 | 2.1595 | 0.0321 | SLAMF8 | −3.2642 | 0.0053 |
| CCL5 | 2.1066 | 0.0342 | CRTAM | −3.2086 | 0.0232 |
| SERPINA5 | 2.0891 | 0.0079 | IL6 | −3.1755 | 0.0065 |
| IGFBP3 | 1.9044 | 0.0219 | ALDH1A1 | −3.168 | 0.0096 |
| PFKM | 1.8788 | 0.0007 | CES1 | −2.9707 | 0.0286 |
| TN-R | 1.8732 | 0.0227 | REG3A | −2.9432 | 0.0499 |
| KLK6 | 1.8647 | 0.0002 | KYNU | −2.9203 | 0.0061 |
| AMBP | 1.8381 | 0.003 | IL-4RA | −2.8507 | 0.0018 |
| SCGB3A2 | 1.8338 | 0.029 | CDCP1 | −2.792 | 0.0097 |
| TWEAK | 1.8183 | 0.0426 | IL6 | −2.781 | 0.0086 |
| FAM19A5 | 1.813 | 0.0186 | IL6 | −2.7351 | 0.0088 |
| CNTN1 | 1.791 | 0.0131 | MVK | −2.6813 | 0.0346 |
| VWC2 | 1.7842 | 0.0316 | FOSB | −2.6284 | 0.0075 |
| CD207 | 1.7751 | 0.0153 | NFATC3 | −2.5865 | 0.0042 |
| HSD11B1 | 1.7507 | 0.0446 | N2DL-2 | −2.5399 | 0.0032 |
| KIT | 1.7369 | 0.0439 | IL6 | −2.5099 | 0.0151 |
| Notch 3 | 1.7306 | 0.0281 | DDAH1 | −2.5062 | 0.0089 |
| GCP5 | 1.7126 | 0.0062 | IGFBP-1 | −2.4965 | 0.0315 |
| BCAN | 1.6911 | 0.0092 | ALDH3A1 | −2.477 | 0.003 |
| CDSN | 1.6718 | 0.0496 | CXADR | −2.4672 | 0.0111 |
| hK14 | 1.6607 | 0.0429 | HAVCR2 | −2.4468 | 0.0022 |
| DRAXIN | 1.6547 | 0.0226 | CKAP4 | −2.3793 | 0.0008 |
| NCAM1 | 1.6306 | 0.0012 | PLXNB1 | −2.3572 | 0.0015 |
| F11 | 1.5723 | 0.0109 | NINJA | −2.3018 | 0.0004 |
| CNDP1 | 1.5685 | 0.0117 | TNFRSF6B | −2.24 | 0.0093 |
| TIMP4 | 1.5269 | 0.0151 | CLM-1 | −2.2069 | 0.0188 |
| NCAN | 1.5261 | 0.0216 | CD74 | −2.2017 | 0.0012 |
| WNT9A | 1.5125 | 0.0206 | ENTPD2 | −2.1935 | 0.0084 |
| MFAP5 | 1.4911 | 0.0342 | PREB | −2.1563 | 0.0115 |
| CCL28 | 1.4765 | 0.0365 | CCL19 | −2.1313 | 0.0252 |
| GALNT10 | 1.4483 | 0.0079 | SIGLEC1 | −2.0772 | 0.0067 |

TABLE 11-continued

Differentially Expressed Proteins at Baseline in the Plasma of Complete Responders Compared to the Progressive Disease/Death Groups

| Up-Regulated in CR Compared to PD/Death | | | Down-Regulated in CR Compared to PD/Death | | |
|---|---|---|---|---|---|
| Protein | Fold Change | Raw P Value | Protein | Fold Change | Raw P Value |
| VEGFD | 1.4176 | 0.0439 | Gal-4 | −2.0631 | 0.0322 |
| DNER | 1.4054 | 0.0481 | HNMT | −2.0614 | 0.0081 |
| CRH | 1.4003 | 0.0285 | HTRA2 | −2.0308 | 0.002 |
| CCL11 | 1.3644 | 0.0126 | VSIG4 | −2.0226 | 0.0258 |
| PAM | 1.3347 | 0.0078 | IL-1RT2 | −2.0162 | 0.013 |
| LY75 | 1.3276 | 0.0287 | TNF-R2 | −2.0135 | 0.0104 |
| CCL11 | 1.3163 | 0.0439 | IL-18R1 | −2.0003 | 0.0005 |
| KLK10 | 1.2844 | 0.0448 | SIRPB1 | −1.9684 | 0.02 |
| | | | TNFRSF10A | −1.9427 | 0.0055 |
| | | | AHCY | −1.8767 | 0.038 |
| | | | DSC2 | −1.8695 | 0.0132 |
| | | | IL12RB1 | −1.8353 | 0.0184 |
| | | | TNFRSF10A | −1.8332 | 0.0075 |
| | | | LILRB4 | −1.832 | 0.0435 |
| | | | TRAIL-R2 | −1.8307 | 0.0191 |
| | | | EPHA2 | −1.7981 | 0.0105 |
| | | | U-PAR | −1.7842 | 0.0224 |
| | | | LAIR1 | −1.7352 | 0.0179 |
| | | | SEMA4C | −1.7209 | 0.0178 |
| | | | CLEC7A | −1.7189 | 0.0411 |
| | | | ANGPTL4 | −1.7097 | 0.0494 |
| | | | RTN4R | −1.6966 | 0.0441 |
| | | | CD163 | −1.6749 | 0.013 |
| | | | VCAM1 | −1.6662 | 0.0161 |
| | | | COL4A1 | −1.663 | 0.0168 |
| | | | PDCD1 | −1.6537 | 0.0108 |
| | | | IFN-gamma-R1 | −1.6515 | 0.0152 |
| | | | IL-1ra | −1.6115 | 0.021 |
| | | | CCL15 | −1.6016 | 0.0159 |
| | | | TGM2 | −1.5838 | 0.0286 |
| | | | DAG1 | −1.58 | 0.0345 |
| | | | NECTIN2 | −1.5594 | 0.049 |
| | | | PILRA | −1.5248 | 0.0281 |
| | | | PD-L1 | −1.5023 | 0.0147 |
| | | | SIGLEC7 | −1.4749 | 0.0364 |
| | | | PRDX6 | −1.4644 | 0.0461 |
| | | | DLL1 | −1.4438 | 0.0003 |
| | | | EDIL3 | −1.2737 | 0.0246 |
| | | | THBS2 | −1.2257 | 0.0104 |
| | | | SPON2 | −1.212 | 0.0024 |

A total of 89 proteins from Table 11 were identified that did not modulate in complete responders between baseline (Day 1) and Day 28. Table 12 represents an updated list of proteins originally shown in Example 2, Table 6. These proteins are designated as baseline predictive biomarkers.

TABLE 12

Proteins from Table 11 that were Stably Expressed in Complete Responders Between Days 1 and 28

| Up-Regulated in CR Compared to PD/Death | | | Down-Regulated in CR Compared to PD/Death | | |
|---|---|---|---|---|---|
| Protein | Fold Change (D1 vs D28) | Raw P Value (D1 vs D28) | Protein | Fold Change (D1 vs D28) | Raw P Value (D1 vs D28) |
| PON3 | 1.3014 | 0.0529 | IL8 | 1.6324 | 0.0814 |
| CNTN1 | 1.1978 | 0.0872 | HAOX1 | 1.5747 | 0.09 |
| IGFBP3 | 1.1493 | 0.1918 | ENPP7 | 1.4178 | 0.1392 |
| LEP | 1.133 | 0.5306 | ACE2 | 1.301 | 0.072 |
| Notch 3 | 1.1259 | 0.1626 | SULT2A1 | 1.2251 | 0.42 |
| TN-R | 1.1234 | 0.2461 | MCP-3 | 1.1945 | 0.3631 |
| HSD11B1 | 1.1146 | 0.3215 | CES1 | 1.1821 | 0.2881 |
| FAM19A5 | 1.0841 | 0.4593 | MFGE8 | 1.1591 | 0.3239 |
| NCAN | 1.0838 | 0.1333 | PLXNB1 | 1.1347 | 0.069 |
| F11 | 1.0834 | 0.2439 | TNFRSF10A | 1.1052 | 0.2863 |
| GDF-8 | 1.0733 | 0.6406 | CCL15 | 1.1003 | 0.3286 |
| CCL28 | 1.0625 | 0.2987 | TNFRSF10A | 1.0972 | 0.2337 |
| GALNT10 | 1.0608 | 0.3706 | SEMA4C | 1.079 | 0.4031 |
| BCAN | 1.0439 | 0.6251 | PREB | 1.0663 | 0.2 |
| TIMP4 | 1.0265 | 0.8344 | NFATC 3 | 1.0623 | 0.7203 |
| CRISP2 | 1.0244 | 0.7055 | CCL19 | 1.0575 | 0.9296 |
| CD207 | 1.0177 | 0.9042 | DLL1 | 1.0479 | 0.5388 |
| WNT9A | 1.0058 | 0.9334 | ENTPD2 | 1.0197 | 0.7027 |
| MBL2 | −1.439 | 0.0693 | IL-4RA | 1.0166 | 0.8889 |

TABLE 12-continued

Proteins from Table 11 that were Stably Expressed in Complete Responders Between Days 1 and 28

| | Up-Regulated in CR Compared to PD/Death | | | Down-Regulated in CR Compared to PD/Death | |
|---|---|---|---|---|---|
| Protein | Fold Change (D1 vs D28) | Raw P Value (D1 vs D28) | Protein | Fold Change (D1 vs D28) | Raw P Value (D1 vs D28) |
| EN-RAGE | −1.3322 | 0.1832 | EPHA2 | 1.0139 | 0.8348 |
| TWEAK | −1.2551 | 0.1314 | FOSB | 1.0051 | 0.9581 |
| CR2 | −1.1488 | 0.312 | CXCL10 | −1.6949 | 0.2429 |
| MFAP5 | −1.1215 | 0.1239 | VAMP5 | −1.3344 | 0.0888 |
| KIT | −1.0943 | 0.3754 | ALDH3A1 | −1.292 | 0.1504 |
| GH | −1.0614 | 0.7936 | MVK | −1.2699 | 0.0932 |
| PFKM | −1.052 | 0.5545 | IL12RB1 | −1.2335 | 0.1735 |
| CDSN | −1.05 | 0.6182 | CALCA | −1.2293 | 0.4153 |
| CRH | −1.0445 | 0.6559 | AHCY | −1.1994 | 0.1462 |
| GCP5 | −1.0404 | 0.6364 | PRSS2 | −1.1946 | 0.2577 |
| KLK6 | −1.0386 | 0.6672 | LILRB4 | −1.1845 | 0.114 |
| DRAXIN | −1.0356 | 0.6586 | DDAH1 | −1.1714 | 0.1479 |
| | | | IL-1ra | −1.1696 | 0.2023 |
| | | | NECTIN2 | −1.1579 | 0.1167 |
| | | | PDCD1 | −1.1485 | 0.0783 |
| | | | CD74 | −1.1483 | 0.1266 |
| | | | PD-L1 | −1.1361 | 0.181 |
| | | | REG3A | −1.1314 | 0.1677 |
| | | | CA5A | −1.1295 | 0.5551 |
| | | | N2DL-2 | −1.1284 | 0.2413 |
| | | | CDCP1 | −1.1249 | 0.5025 |
| | | | U-PAR | −1.0962 | 0.2869 |
| | | | SIGLEC7 | −1.0923 | 0.3111 |
| | | | ANGPTL4 | −1.088 | 0.618 |
| | | | ALDH1A1 | −1.0791 | 0.6027 |
| | | | SPINK1 | −1.0709 | 0.7767 |
| | | | HTRA2 | −1.0707 | 0.4567 |
| | | | PRDX6 | −1.061 | 0.5849 |
| | | | IL-1RT2 | −1.0504 | 0.6889 |
| | | | IGFBP-1 | −1.0455 | 0.8818 |
| | | | HNMT | −1.0338 | 0.5282 |
| | | | TRAIL-R2 | −1.0337 | 0.6738 |
| | | | CXADR | −1.0305 | 0.484 |
| | | | CTSL1 | −1.0288 | 0.8442 |
| | | | IFN-gamma-R1 | −1.0268 | 0.6494 |
| | | | IL-18R1 | −1.0192 | 0.5615 |
| | | | KRT19 | −1.0142 | 0.9196 |
| | | | KYNU | −1.0138 | 0.9268 |
| | | | TGM2 | −1.0122 | 0.9074 |

Example 6: Characterization of Protein Expression During the Course of Treatment Longitudinal differences in protein expression were analyzed by evaluating plasma samples from baseline/screening and day 28. Proteins were identified that were significantly modulated by treatment between screening/baseline and day 28 in responders, including CR, VGPR, and PR patients (N=19). A total of 353 proteins were identified, and are shown in Table 13. From this list, 105 proteins were significantly elevated, and 248 proteins were significantly reduced between baseline and day 28. The list of proteins in Table 13 includes proteins included in Example 2, Table 5, and includes proteins modulated by treatment in CR, VGPR, and PR patients. Table 13 identifies biomarkers of therapeutic response.

TABLE 13

Proteins Significantly Modulated in Responders (CR, VGPR, PR; n = 19) Between Baseline and Day 28

| | Increased Expression from Baseline to Day 28 | | | Decreased Expression from Baseline to Day 28 | |
|---|---|---|---|---|---|
| Protein | Fold Change | Raw P Value | Protein | Fold Change | Raw P Value |
| TMPRSS15 | 3.0633 | 7.04E−07 | INPPL1 | 4.7131 | 8.25E−06 |
| CCL11 | 1.3146 | 4.74E−06 | LAT2 | −1.7755 | 1.01E−05 |
| FAM3B | 1.7951 | 1.23E−05 | CLEC7A | −1.8103 | 1.39E−05 |
| MMP7 | 1.3986 | 2.15E−05 | PPP1R9B | −1.6445 | 2.13E−05 |
| NCAM1 | 1.3216 | 9.44E−05 | NEMO | −1.7984 | 2.56E−05 |
| Gal-3 | 1.3504 | 0.0001 | SH2B3 | 4.7273 | 3.46E−05 |
| CCL25 | 2.106 | 0.0001 | BCR | −1.8219 | 5.51E−05 |
| THPO | 1.867 | 0.0002 | CD5 | −1.9942 | 6.02E−05 |
| CCL11 | 1.2818 | 0.0003 | DNAJB1 | −1.7332 | 8.26E−05 |
| hK14 | 1.5574 | 0.0004 | CCL17 | −3.059 | 8.32E−05 |
| KIM1 | 1.7741 | 0.0004 | ITGB2 | −1.6877 | 8.97E−05 |
| Flt3L | 2.3423 | 0.0004 | BANK1 | −2.0084 | 0.0001 |
| PLIN1 | 2.4338 | 0.0005 | TPSAB 1 | −1.9835 | 0.0001 |
| SPON2 | 1.095 | 0.0006 | YES1 | −1.9824 | 0.0001 |
| Gal-4 | 1.4274 | 0.0006 | LAMP3 | −1.7705 | 0.0001 |
| FABP4 | 1.6926 | 0.0006 | GM-CSF-R-alpha | −1.4489 | 0.0001 |
| DNER | 1.2957 | 0.0007 | | | |
| GAL | 1.6888 | 0.0008 | CNTNAP2 | −1.3091 | 0.0001 |
| KIM1 | 1.757 | 0.0009 | ZBTB16 | −1.9166 | 0.0002 |
| CPM | 1.1479 | 0.0011 | CD163 | −1.7206 | 0.0002 |
| VWC2 | 1.3331 | 0.0011 | TXLNA | −1.5277 | 0.0002 |
| PPY | 1.9703 | 0.0012 | MEPE | −1.4941 | 0.0002 |
| PAM | 1.1653 | 0.0014 | BACH1 | −1.4794 | 0.0002 |
| PVR | 1.1964 | 0.0015 | MAX | −1.449 | 0.0002 |
| SERPINA5 | 1.2683 | 0.0015 | NFKBIE | −1.2885 | 0.0002 |

TABLE 13-continued

Proteins Significantly Modulated in Responders (CR, VGPR, PR; n = 19) Between Baseline and Day 28

| Increased Expression from Baseline to Day 28 | | | Decreased Expression from Baseline to Day 28 | | |
|---|---|---|---|---|---|
| Protein | Fold Change | Raw P Value | Protein | Fold Change | Raw P Value |
| ST3GAL1 | 1.3415 | 0.0016 | hOSCAR | −1.2603 | 0.0002 |
| CST5 | 1.3521 | 0.002 | LAT | −2.049 | 0.0003 |
| CES2 | 1.4212 | 0.0022 | PTPRJ | −1.7421 | 0.0003 |
| CNDP1 | 1.3856 | 0.0024 | SIRT2 | −1.6014 | 0.0003 |
| CX3CL1 | 1.5454 | 0.0024 | SIRPB1 | −1.3991 | 0.0003 |
| HO-1 | 1.3293 | 0.0028 | AXIN1 | −1.8046 | 0.0004 |
| PRELP | 1.1833 | 0.0029 | EIF4G1 | −1.5969 | 0.0004 |
| ADM | 1.2035 | 0.003 | PTX3 | −1.5567 | 0.0004 |
| VSIG2 | 1.2163 | 0.0031 | TRIM5 | −1.4743 | 0.0004 |
| FABP2 | 3.5893 | 0.0031 | IDUA | −1.3887 | 0.0004 |
| CEACAM5 | 1.6422 | 0.0039 | NCF2 | −2.4951 | 0.0005 |
| SLITRK2 | 1.2986 | 0.004 | SELP | −1.9244 | 0.0005 |
| MCP-1 | 1.6302 | 0.0044 | ARHGEF12 | −1.8347 | 0.0005 |
| NTRK3 | 1.2526 | 0.0045 | CASP-3 | −1.787 | 0.0005 |
| CLUL1 | 1.3108 | 0.0046 | CD27 | −1.6873 | 0.0005 |
| CXCL16 | 1.2028 | 0.0053 | MAP4K5 | −1.658 | 0.0005 |
| SCF | 1.4714 | 0.0056 | DAPP1 | −1.3805 | 0.0005 |
| TMPRSS5 | 1.3307 | 0.0057 | PRDX5 | −2.0131 | 0.0006 |
| REG4 | 2.1118 | 0.0059 | TLT-2 | −1.8372 | 0.0006 |
| hK11 | 1.2975 | 0.0061 | PARK7 | −1.4104 | 0.0006 |
| SCF | 1.3943 | 0.0061 | IL2-RA | −2.2452 | 0.0007 |
| SCGB3A1 | 1.5691 | 0.0061 | FOXO1 | −1.3557 | 0.0007 |
| DKKL1 | 1.1495 | 0.0071 | ST1A1 | −1.9523 | 0.0008 |
| NEP | 1.8376 | 0.0077 | GRAP2 | −1.6468 | 0.0008 |
| CPA2 | 1.7185 | 0.0088 | NBN | −1.5879 | 0.0008 |
| Ep-CAM | 1.403 | 0.0089 | CD93 | −1.3029 | 0.0008 |
| THBS2 | 1.0963 | 0.0091 | FCGR2A | −1.5278 | 0.0009 |
| GPNMB | 1.2117 | 0.0092 | DCTN1 | −1.4726 | 0.0009 |
| ITGB5 | 1.229 | 0.0104 | IRF9 | −1.4384 | 0.0009 |
| GT | 1.8699 | 0.0104 | HAVCR2 | −1.312 | 0.0009 |
| APLP1 | 1.4933 | 0.0117 | CD84 | −1.7208 | 0.001 |
| TACSTD2 | 1.1931 | 0.0119 | STX8 | −1.4796 | 0.001 |
| NINJA | 1.2723 | 0.012 | LY9 | −1.4447 | 0.001 |
| SCF | 1.4058 | 0.0123 | ZBTB16 | −1.9288 | 0.0011 |
| REN | 1.4074 | 0.0137 | CD200R1 | −1.4752 | 0.0011 |
| GCG | 1.8922 | 0.0137 | TOP2B | −1.7634 | 0.0012 |
| SERPINA9 | 1.5418 | 0.0151 | THY 1 | −1.2913 | 0.0012 |
| KAZALD1 | 1.2609 | 0.0154 | PRKRA | −1.2761 | 0.0012 |
| SERPINA12 | 1.567 | 0.0155 | ITGB1BP2 | −1.8787 | 0.0013 |
| PODXL | 1.2014 | 0.0163 | CD48 | −1.6022 | 0.0013 |
| AMN | 1.2517 | 0.017 | CD244 | −1.5176 | 0.0014 |
| IGF1R | 1.2432 | 0.0171 | HCLS1 | −1.455 | 0.0014 |
| LTBP2 | 1.1874 | 0.0175 | MPO | −1.8431 | 0.0015 |
| ANGPTL3 | 1.2673 | 0.0177 | SIT1 | −1.5501 | 0.0015 |
| SCARA5 | 1.1342 | 0.0179 | ICAM3 | −1.464 | 0.0015 |
| B4GAT1 | 1.2795 | 0.0179 | SOST | −1.3214 | 0.0015 |
| ROBO2 | 1.249 | 0.0181 | DDX58 | −1.6381 | 0.0016 |
| PDGFC | 1.223 | 0.0199 | TNF-R2 | −1.5017 | 0.0016 |
| CA12 | 1.247 | 0.0199 | TRAF2 | −1.4472 | 0.0016 |
| DDC | 1.5485 | 0.0203 | SMAD1 | −1.3807 | 0.0016 |
| EDIL3 | 1.12 | 0.0237 | LAIR-2 | −1.8117 | 0.0017 |
| XPNPEP2 | 1.285 | 0.0268 | PIK3AP1 | −1.7193 | 0.0018 |
| PRTG | 1.1026 | 0.0278 | VSIG4 | −1.5046 | 0.0018 |
| NQO2 | 1.0895 | 0.0282 | SIGLEC10 | −1.4974 | 0.0019 |
| AMBP | 1.1635 | 0.0282 | CD6 | −1.758 | 0.002 |
| ERBB2 | 1.1968 | 0.0283 | SKAP1 | −1.8075 | 0.0021 |
| IL6 | 2.0047 | 0.0286 | FCRL5 | −1.3113 | 0.0021 |
| IL6 | 1.8649 | 0.0297 | CD177 | −1.768 | 0.0022 |
| MCP-1 | 1.4322 | 0.0301 | KLRD1 | −1.8117 | 0.0023 |
| VEGFD | 1.147 | 0.0314 | ERBB2IP | −1.7337 | 0.0023 |
| GDF-2 | 1.3656 | 0.0326 | MILR1 | −1.3829 | 0.0023 |
| MUC-16 | 1.6356 | 0.0334 | MIF | −1.7486 | 0.0024 |
| KLK10 | 1.2102 | 0.0341 | SNAP23 | −1.5751 | 0.0024 |
| FAM3C | 1.3109 | 0.0341 | NUB1 | −1.4966 | 0.0025 |
| uPA | 1.1411 | 0.0346 | TIGAR | −1.3733 | 0.0026 |
| IL6 | 1.7278 | 0.0347 | STAMPB | −1.3721 | 0.0026 |
| AGR2 | 1.4472 | 0.0376 | DSC2 | −1.3652 | 0.0028 |
| METRNL | 1.2013 | 0.039 | LAIR1 | −1.3173 | 0.0028 |
| RTN4R | 1.195 | 0.0391 | FKBP1B | −1.9994 | 0.0029 |
| IGF2R | 1.1734 | 0.0395 | RASSF2 | −1.5477 | 0.003 |
| NTRK2 | 1.118 | 0.0399 | FATC1 | −1.5044 | 0.0031 |

TABLE 13-continued

Proteins Significantly Modulated in Responders (CR, VGPR, PR; n = 19) Between Baseline and Day 28

| Increased Expression from Baseline to Day 28 | | | Decreased Expression from Baseline to Day 28 | | |
|---|---|---|---|---|---|
| Protein | Fold Change | Raw P Value | Protein | Fold Change | Raw P Value |
| ITGB6 | 1.152 | 0.0422 | CBL | −1.7183 | 0.0033 |
| SCARF2 | 1.1639 | 0.0422 | IgG Fc receptor II-b | −1.3893 | 0.0033 |
| SCGB3A2 | 1.3677 | 0.0439 | | | |
| RGMB | 1.1254 | 0.0449 | GLO1 | −1.2571 | 0.0034 |
| EZR | 1.1031 | 0.0454 | PVALB | −2.0291 | 0.0035 |
| PROC | 1.243 | 0.0456 | SCAMP3 | −1.7405 | 0.0035 |
| FURIN | 1.2365 | 0.0464 | SLAMF8 | −1.492 | 0.0035 |
| PIgR | 1.1476 | 0.049 | STX16 | −1.4673 | 0.0035 |
| SMOC2 | 1.2842 | 0.0494 | TNF-R1 | −1.3972 | 0.0035 |
| | | | DFFA | −1.31 | 0.0038 |
| | | | PPP1R2 | −1.3339 | 0.0039 |
| | | | ANG-1 | −1.7898 | 0.004 |
| | | | CCL5 | −1.6357 | 0.0044 |
| | | | MAP2K6 | −1.8184 | 0.0046 |
| | | | CRKL | −1.8003 | 0.0047 |
| | | | CD38 | −1.4181 | 0.0048 |
| | | | CXCL5 | −1.7254 | 0.0052 |
| | | | PILRA | −1.2582 | 0.0052 |
| | | | IRAK1 | −1.2986 | 0.0053 |
| | | | CA13 | −1.8816 | 0.0054 |
| | | | STX6 | −1.4715 | 0.0055 |
| | | | PRTN3 | −1.7658 | 0.0056 |
| | | | IL-5R-alpha | −1.6599 | 0.0058 |
| | | | ESM-1 | −1.4178 | 0.0058 |
| | | | EGLN1 | −1.3184 | 0.0062 |
| | | | CLEC1B | −1.7033 | 0.0063 |
| | | | TYMP | −1.7313 | 0.0066 |
| | | | SNAP29 | −1.6325 | 0.0067 |
| | | | PDGF subunit A | −1.6021 | 0.0069 |
| | | | TNFRSF11A | −1.3519 | 0.007 |
| | | | gal-8 | −1.3154 | 0.007 |
| | | | GCNT1 | −1.3034 | 0.0071 |
| | | | STK4 | −1.8393 | 0.0072 |
| | | | TNC | −1.6915 | 0.0073 |
| | | | THBS4 | −1.7307 | 0.0075 |
| | | | CLEC4D | −1.7084 | 0.0076 |
| | | | SIGLEC6 | −1.9024 | 0.0078 |
| | | | WASF1 | −1.5354 | 0.0078 |
| | | | WAS | −2.133 | 0.0079 |
| | | | COMT | −1.4304 | 0.0082 |
| | | | RETN | −1.8687 | 0.0084 |
| | | | SH2D1A | −1.1574 | 0.0084 |
| | | | RNASE3 | −2.6612 | 0.0087 |
| | | | PAR-1 | −1.2074 | 0.0088 |
| | | | CD69 | −1.7621 | 0.0089 |
| | | | SIGLEC1 | −1.3842 | 0.0089 |
| | | | FR-gamma | −1.2115 | 0.009 |
| | | | ADAM8 | −1.3896 | 0.0091 |
| | | | AZU1 | −2.0976 | 0.0093 |
| | | | AREG | −1.5881 | 0.0093 |
| | | | SDC4 | −1.4678 | 0.0094 |
| | | | DCTN2 | −1.5624 | 0.0096 |
| | | | BID | −1.382 | 0.0097 |
| | | | RELT | −1.3317 | 0.0099 |
| | | | CLEC5A | −1.3618 | 0.0102 |
| | | | APEX1 | −1.5431 | 0.0103 |
| | | | PSP-D | −1.2426 | 0.0106 |
| | | | FGR | −1.4406 | 0.0108 |
| | | | SELE | −1.5291 | 0.0112 |
| | | | SELL | −1.4428 | 0.0112 |
| | | | MESDC2 | −1.7056 | 0.0114 |
| | | | IQGAP2 | −1.5317 | 0.012 |
| | | | AREG | −1.5142 | 0.0121 |
| | | | CRTAM | −1.5805 | 0.0124 |
| | | | LILRB2 | −1.2555 | 0.0126 |
| | | | TANK | −1.3124 | 0.0127 |
| | | | CPXM1 | −1.4779 | 0.0131 |
| | | | ARSB | −1.3432 | 0.0131 |
| | | | SLAMF1 | −1.2218 | 0.0133 |
| | | | PEBP1 | −1.307 | 0.0135 |
| | | | STIP1 | −1.2812 | 0.0144 |

TABLE 13-continued

Proteins Significantly Modulated in Responders (CR, VGPR, PR; n = 19) Between Baseline and Day 28

| Increased Expression from Baseline to Day 28 | | | Decreased Expression from Baseline to Day 28 | | |
|---|---|---|---|---|---|
| Protein | Fold Change | Raw P Value | Protein | Fold Change | Raw P Value |
| | | | PDGF subunit B | −1.9124 | 0.0145 |
| | | | SCARF1 | −1.3509 | 0.0146 |
| | | | DEFA1 | −1.9173 | 0.0148 |
| | | | EPHB4 | −1.2339 | 0.015 |
| | | | ARHGAP1 | −1.6039 | 0.0155 |
| | | | CLM-1 | −1.3921 | 0.0156 |
| | | | DAB2 | −1.2548 | 0.0158 |
| | | | LYN | −1.2337 | 0.0158 |
| | | | CASP-8 | −1.4795 | 0.016 |
| | | | APBB1IP | −1.4021 | 0.0161 |
| | | | ANXA11 | −1.3456 | 0.0167 |
| | | | ICAM1 | −1.354 | 0.017 |
| | | | PRKCQ | −1.3251 | 0.0171 |
| | | | VCAM1 | −1.2102 | 0.0173 |
| | | | HDGF | −1.3392 | 0.0174 |
| | | | CD2AP | −1.3188 | 0.0175 |
| | | | TNFRSF6B | −1.3504 | 0.0177 |
| | | | CLEC1A | −1.2841 | 0.0179 |
| | | | TNFRSF14 | −1.2658 | 0.0179 |
| | | | TACC3 | −1.7676 | 0.0181 |
| | | | MMP-1 | −1.4112 | 0.0186 |
| | | | NRP1 | −1.1237 | 0.0187 |
| | | | ZBTB17 | −1.2333 | 0.0189 |
| | | | NADK | −1.3493 | 0.019 |
| | | | PLXNA4 | −1.405 | 0.0193 |
| | | | MMP-9 | −1.9306 | 0.0198 |
| | | | NCR1 | −1.3726 | 0.0202 |
| | | | AMIGO2 | −1.1962 | 0.0202 |
| | | | FES | −1.4934 | 0.0204 |
| | | | CD79B | −1.2372 | 0.0206 |
| | | | TNXB | −1.156 | 0.0216 |
| | | | TXNDC5 | −1.4081 | 0.0217 |
| | | | TRANCE | −1.4034 | 0.0222 |
| | | | ARG1 | −1.3036 | 0.0225 |
| | | | PCDH17 | −1.232 | 0.0228 |
| | | | LRMP | −1.6365 | 0.0231 |
| | | | C1QTNF1 | −1.2979 | 0.0231 |
| | | | CLM-6 | −1.1356 | 0.0232 |
| | | | CKAP4 | −1.1904 | 0.0237 |
| | | | APP | −1.5208 | 0.0244 |
| | | | PGLYRP1 | −1.6181 | 0.0255 |
| | | | LILRA5 | −1.342 | 0.0271 |
| | | | CLEC10A | −1.274 | 0.028 |
| | | | NMNAT1 | −1.4212 | 0.0286 |
| | | | IL-6RA | −1.1901 | 0.0287 |
| | | | ATG4A | −1.3651 | 0.0289 |
| | | | TIMP1 | −1.2337 | 0.029 |
| | | | COCH | −1.22 | 0.0294 |
| | | | DKN1A | −1.4302 | 0.0303 |
| | | | CD1C | −1.5651 | 0.0305 |
| | | | DECR1 | −1.4327 | 0.0316 |
| | | | DAG1 | −1.2406 | 0.0317 |
| | | | IGFBP-2 | −1.2058 | 0.0321 |
| | | | RET | −1.4592 | 0.0329 |
| | | | GSAP | −1.4153 | 0.0338 |
| | | | PILRB | −1.3019 | 0.0338 |
| | | | CLEC6A | −1.3248 | 0.0343 |
| | | | PECAM-1 | −1.2009 | 0.0347 |
| | | | PXN | −1.329 | 0.0359 |
| | | | ADGRG1 | −1.1823 | 0.0378 |
| | | | DPP7 | −1.1582 | 0.038 |
| | | | TDRKH | −1.2785 | 0.0385 |
| | | | Siglec-9 | −1.1514 | 0.0387 |
| | | | CD40-L | −1.5868 | 0.0388 |
| | | | VEGFC | −1.1727 | 0.04 |
| | | | LYVE1 | −1.227 | 0.0403 |
| | | | FADD | −1.546 | 0.041 |
| | | | FCRL1 | −1.3733 | 0.0416 |
| | | | EGF | −1.7729 | 0.0419 |
| | | | HGF | −1.5542 | 0.0426 |
| | | | GZMH | −1.494 | 0.0428 |

TABLE 13-continued

Proteins Significantly Modulated in Responders (CR, VGPR, PR; n = 19) Between Baseline and Day 28

| | Increased Expression from Baseline to Day 28 | | Decreased Expression from Baseline to Day 28 | | |
|---|---|---|---|---|---|
| Protein | Fold Change | Raw P Value | Protein | Fold Change | Raw P Value |
| | | | CLEC4G | −1.1865 | 0.045 |
| | | | LY75 | −1.1401 | 0.0452 |
| | | | PRDX3 | −1.199 | 0.0465 |
| | | | COL4A1 | −1.2699 | 0.0466 |
| | | | CEACAM8 | −1.6177 | 0.0471 |
| | | | SEMA7A | −1.1335 | 0.0475 |
| | | | NUDT5 | −1.5449 | 0.0476 |
| | | | FCRL6 | −1.3556 | 0.0476 |
| | | | PAPPA | −1.3491 | 0.0485 |
| | | | FASLG | −1.3614 | 0.0486 |
| | | | GRN | −1.2448 | 0.0486 |
| | | | MATN3 | −1.3384 | 0.049 |

Example 7: Protein Expression Levels for Selected Biomarkers in Complete Responder and Progressive Disease/Death Populations Targeted proteomic analysis of MCP-3 (CCL7), Reg3A, TNFRSF6B, SCF, CXCL10, IL-8, ST2, CALCA, TNF-R1, IL-6, CCL19, IL-2Ra, and PON3 was conducted using the OLINK proximity extension assay platform. Table 14 provides expression information for each of the proteins within the Complete Responder (CR) and Progressive Disease/Death (PD/Death) groups. For each protein, Table 14 includes the median and mean protein expression levels (pg/ml) within each group, standard error, range, and statistical differences between the CR and PD/Death groups. Statistical differences between the groups were identified using an unpaired T test.

TABLE 14

Protein Expression in Complete Responder and Progressive Disease/Death Populations

| | CR (N = 10) (pg/ml) | | | | PD/Death (N = 7) (pg/ml) | | | | p value (unpaired t test) |
|---|---|---|---|---|---|---|---|---|---|
| Analyte | median | mean | SEM | range | median | mean | SEM | range | |
| MCP-3 (CCL7) | 2.343 | 2.613 | 0.4318 | 0.7949-4.862 | 16.66 | 21.35 | 5.705 | 3.907-42.27 | 0.0013 |
| Reg3A | 4150 | 9252 | 3597 | 728.8-28209 | 49259 | 47951 | 8907 | 19613-81454 | 0.0006 |
| TNFRSF6B | 159 | 184.7 | 26.38 | 67.97-308.7 | 413.6 | 411.9 | 72.41 | 203-681.7 | 0.0043 |
| SCF | 627.6 | 639 | 90.92 | 185.2-1171 | 318.4 | 283.7 | 38.16 | 151.2-398.6 | 0.0071 |
| CXCL10 | 200.6 | 307.2 | 81.94 | 96.17-879.4 | 941.8 | 920.4 | 231.6 | 147.6-1991 | 0.0121 |
| IL-8 | 5.332 | 9.346 | 2.458 | 2.629-23 | 42.87 | 54.49 | 17.53 | 15.03-155.7 | 0.0079 |
| ST2 | 47037 | 70902 | 19650 | 24630-205075 | 142056 | 163519 | 38569 | 55016-318173 | 0.0339 |
| CALCA | 1456 | 1826 | 392.6 | 858.5-5026 | 3130 | 5996 | 2494 | 1375-19759 | 0.0669 |
| TNF-R1 | 9199 | 8822 | 1056 | 3713-15630 | 12659 | 13129 | 1265 | 10015-20208 | 0.0195 |
| IL-6 | 1.068 | 0.9521 | 0.1724 | 0.1551-1.791 | 3.753 | 7.156 | 4.24 | 0.9551-32.2 | 0.0969 |
| CCL19 | 439.1 | 484.9 | 80.79 | 156.5-973.4 | 1036 | 1751 | 663.3 | 203.6-5450 | 0.0377 |
| IL-2Ra | 355 | 469.8 | 94.9 | 63.64-1178 | 612.6 | 577.4 | 96.43 | 213.8-856.9 | 0.4771 |
| PON3 | 386584 | 438566 | 61426 | 254507-885782 | 93702 | 148321 | 37162 | 50041-284920 | 0.0025 |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a human subject having Graft-Versus-Host Disease (GvHD), comprising administering to the human subject a therapy comprising a JAK inhibitor, wherein the human subject has been previously determined to have (i) a baseline concentration of at least one protein selected from the group consisting of IL8, HAOX1, ENPP7, ACE2, SULT2A1, MCP-3, CES1, MFGE8, PLXNB1, TNFRSF10A, CCL15, SEMA4C, PREB, NFATC3, CCL19, DLL1, ENTPD2, IL-4RA, EPHA2, FOSB, CXCL10, VAMP5, ALDH3A1, MVK, IL12RB1, CALCA, AHCY, PRSS2, LILRB4, DDAH1, IL-1ra, NECTIN2, PDCD1, CD74, PD-L1, REG3A, CASA, N2DL-2, CDCP1, U-PAR, SIGLEC7, ANGPTL4, ALDH1A1, SPINK1, HTRA2, PRDX6, IL-1RT2, IGFBP-1, HNMT, TRAIL-R2, CXADR, CTSL1, IFN-gamma-R1, IL-18R1, KRT19, KYNU, and TGM2 in a biological sample obtained from the human subject that is lower than a control, and/or (ii) a baseline concentration of at least one protein selected from the group consisting of PON3, CNTN1, IGFBP3, LEP, Notch 3, TN-R, HSD11B1, FAM19A5, NCAN, F11, GDF-8, CCL28, GALNT10, BCAN, TIMP4, CRISP2, CD207, WNT9A, MBL2, EN-RAGE, TWEAK, CR2, MFAP5, KIT, GH, PFKM, CDSN, CRH, GCP5, KLK6, and DRAXIN in a biological sample obtained from the human subject that is higher than a control,
wherein the control is the concentration of the protein in a sample or samples obtained from one or more subjects that have not responded to treatment with the JAK inhibitor.

2. The method of claim 1, wherein the human subject has been previously determined to have (i) a baseline concentration of at least one protein selected from the group consisting of MCP-3, HAOX1, CASA, CALCA, IL8, SULT2A1, VAMP5, SPINK1, ENPP7, ACE2, CTSL1, PRSS2, CXCL10, MFGE8, KRT19, ALDH1A1, CES1, REG3A, KYNU, IL-4RA, CDCP1, MVK, FOSB, NFATC3, N2DL-2, DDAH1, IGFBP-1, ALDH3A1, CXADR, PLXNB1, CD74, ENTPD2, PREB, CCL19, HNMT, HTRA2, IL-1RT2, and IL-18R1 in a biological sample obtained from the human subject that is lower than a control, and/or (ii) a baseline concentration of at least one protein selected from the group consisting of PON3, LEP, MBL2, GH, GDF-8, EN-RAGE, CRISP2, and CR2 in a biological sample obtained from the human subject that is higher than a control.

3. The method of claim 1, wherein the human subject has been previously determined to have (i) a baseline concentration of at least one protein selected from the group consisting of MCP-3, HAOX1, CASA, CALCA, IL8, SULT2A1, VAMP5, SPINK1, ENPP7, ACE2, CTSL1, PRSS2, CXCL10, MFGE8, KRT19, and ALDH1A1 in a biological sample obtained from the human subject that is lower than a control, and/or (ii) a baseline concentration of at least one protein selected from the group consisting of PON3, LEP, and MBL2 in a biological sample obtained from the human subject that is higher than a control.

4. The method of claim 1, wherein the human subject has been previously determined to have (i) a baseline concentration of at least one protein selected from the group consisting of MCP-3, HAOX1, CASA, CALCA, IL8, SULT2A1, VAMP5, and SPINK1 in a biological sample obtained from the human subject that is lower than a control, and/or (ii) a baseline concentration of at least one protein selected from the group consisting of PON3 and LEP in a biological sample obtained from the human subject that is higher than a control.

5. A method of treating a human subject having developing Graft-Versus-Host Disease (GvHD), comprising:
providing a biological sample obtained from the human subject;
measuring in the biological sample a reduced concentration, as compared to a control, of at least one protein selected from the group consisting of IL8, HAOX1, ENPP7, ACE2, SULT2A1, MCP-3, CES1, MFGE8, PLXNB1, TNFRSF10A, CCL15, SEMA4C, PREB, NFATC3, CCL19, DLL1, ENTPD2, IL-4RA, EPHA2, FOSB, CXCL10, VAMP5, ALDH3A1, MVK, IL12RB1, CALCA, AHCY, PRSS2, LILRB4, DDAH1, IL-1ra, NECTIN2, PDCD1, CD74, PD-L1, REG3A, CASA, N2DL-2, CDCP1, U-PAR, SIGLEC7, ANGPTL4, ALDH1A1, SPINK1, HTRA2, PRDX6, IL-1RT2, IGFBP-1, HNMT, TRAIL-R2, CXADR, CTSL1, IFN-gamma-R1, IL-18R1, KRT19, KYNU, and TGM2, and/or an increased concentration, as compared to a control, of at least one protein selected from the group consisting of PON3, CNTN1, IGFBP3, LEP, Notch 3, TN-R, HSD11B1, FAM19A5, NCAN, F11, GDF-8, CCL28, GALNT10, BCAN, TIMP4, CRISP2, CD207, WNT9A, MBL2, EN-RAGE, TWEAK, CR2, MFAP5, KIT, GH, PFKM, CDSN, CRH, GCP5, KLK6, and DRAXIN; and
administering a therapy comprising a JAK inhibitor to the human subject,
wherein the control is the concentration of the protein in a sample or samples obtained from one or more subjects that have not responded to treatment with the JAK inhibitor.

6. The method of claim 5, comprising:
measuring in the biological sample a reduced concentration, as compared to a control, of at least one protein selected from the group consisting of MCP-3, HAOX1, CASA, CALCA, IL8, SULT2A1, VAMP5, SPINK1, ENPP7, ACE2, CTSL1, PRSS2, CXCL10, MFGE8, KRT19, ALDH1A1, CES1, REG3A, KYNU, IL-4RA, CDCP1, MVK, FOSB, NFATC3, N2DL-2, DDAH1, IGFBP-1, ALDH3A1, CXADR, PLXNB1, CD74, ENTPD2, PREB, CCL19, HNMT, HTRA2, IL-1RT2, and IL-18R1, and/or an increased concentration, as compared to a control, of at least one protein selected from the group consisting of PON3, LEP, MBL2, GH, GDF-8, EN-RAGE, CRISP2, and CR2; and
administering the therapy comprising the JAK inhibitor to the human subject.

7. The method of claim 5, comprising:
measuring in the biological sample a reduced concentration, as compared to a control, of at least one protein selected from the group consisting of MCP-3, HAOX1, CASA, CALCA, IL8, SULT2A1, VAMP5, SPINK1, ENPP7, ACE2, CTSL1, PRSS2, CXCL10, MFGE8, KRT19, and ALDH1A1, and/or an increased concentration, as compared to a control, of at least one protein selected from the group consisting of PON3, LEP, and MBL2; and
administering the therapy comprising the JAK inhibitor to the human subject.

8. The method of claim 5, comprising:
measuring in the biological sample a reduced concentration, as compared to a control, of at least one protein selected from the group consisting of MCP-3, HAOX1, CASA, CALCA, IL8, SULT2A1, VAMP5, and SPINK1, and/or an increased concentration, as compared to a control, of at least one protein selected from the group consisting of PON3 and LEP; and
administering the therapy comprising the JAK inhibitor to the human subject.

9. The method of claim 1, wherein a second therapeutic agent is administered to the human subject in combination with the JAK inhibitor.

10. The method of claim 9, wherein the second therapeutic agent is a corticosteroid, methotrexate, cyclosporine, mycophenolate mofetil, tacrolimus, sirolimus, everolimus, antithymocyte globulin, alemtuzumab, cyclophosphamide, ibrutinib, imatinib, infliximab, etanercept, tocilizumab, alemtuzumab, basiliximab, daclizumab, rituximab, denileukin diftitox, pentostatin, ciclosporin, thalidomide, halofuginone, hydroxychloroquine, or mesenchymal stem cells.

11. The method of claim 9, wherein the second therapeutic agent is a corticosteroid.

12. The method of claim 11, wherein the corticosteroid is methylprednisolone or prednisone.

13. The method of claim 1, wherein the biological sample is blood, serum, plasma, urine, spinal fluid, saliva, lacrimal fluid, or sweat.

14. The method of claim 1, wherein the biological sample is blood, serum, or plasma.

15. The method of claim 1, wherein the concentration of the protein is measured by an immunological method.

16. The method of claim 15, wherein the immunological method is selected from the group consisting of enzyme-linked immunosorbent assay, enzyme immunoassay, radioimmunoassay, chemiluminescent immunoassay, electrochemiluminescence immunoassay, latex turbidimetric immunoassay, latex photometric immunoassay, immunochromatographic assay, and western blotting.

17. The method of claim 1, wherein the concentration of the protein is measured by mass spectrometry.

18. The method of claim 1, wherein the JAK inhibitor is itacitinib.

19. The method of claim 1, wherein the JAK inhibitor is 4-[3-(cyanomethyl)-3-(3',5'-dimethyl-1H, 1'H-4,4'-bipyrazol-1-yl)azetidin-1-yl]-2,5-difluoro-N-[(1S)-2,2,2-trifluoro-1-methylethyl]benzamide or a pharmaceutically acceptable salt thereof or ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile or a pharmaceutically acceptable salt thereof.

20. The method of claim 1, wherein the GvHD is acute GvHD.

21. The method of claim 1, wherein the GvHD is chronic GvHD.

22. The method of claim 5, wherein a second therapeutic agent is administered to the human subject in combination with the JAK inhibitor.

23. The method of claim 22, wherein the second therapeutic agent is a corticosteroid, methotrexate, cyclosporine, mycophenolate mofetil, tacrolimus, sirolimus, everolimus, antithymocyte globulin, alemtuzumab, cyclophosphamide, ibrutinib, imatinib, infliximab, etanercept, tocilizumab, alemtuzumab, basiliximab, daclizumab, rituximab, denileukin diftitox, pentostatin, thalidomide, halofuginone, hydroxychloroquine, or mesenchymal stem cells.

24. The method of claim 22, wherein the second therapeutic agent is a corticosteroid.

25. The method of claim 24, wherein the corticosteroid is methylprednisolone or prednisone.

26. The method of claim 5, wherein the biological sample is blood, serum, plasma, urine, spinal fluid, saliva, lacrimal fluid, or sweat.

27. The method of claim 5, wherein the biological sample is blood, serum, or plasma.

28. The method of claim 5, wherein the concentration of the protein is measured by an immunological method.

29. The method of claim 28, wherein the immunological method is selected from the group consisting of enzyme-linked immunosorbent assay, enzyme immunoassay, radioimmunoassay, chemiluminescent immunoassay, electrochemiluminescence immunoassay, latex turbidimetric immunoassay, latex photometric immunoassay, immunochromatographic assay, and western blotting.

30. The method of claim 5, wherein the concentration of the protein is measured by mass spectrometry.

31. The method of claim 5, wherein the JAK inhibitor is itacitinib.

32. The method of claim 5, wherein the JAK inhibitor is 4-[3-(cyanomethyl)-3-(3',5'-dimethyl-1H, 1'H-4,4'-bipyrazol-1-yl)azetidin-1-yl]-2,5-difluoro-N-[(1 S)-2,2,2-trifluoro-1-methylethyl]benzamide or a pharmaceutically acceptable salt thereof or ((2R,5S)-5-{2-[(1R)-1-hydroxyethyl]-1H-imidazo[4,5-d]thieno [3,2-b]pyridin-1-yl}tetrahydro-2H-pyran-2-yl)acetonitrile or a pharmaceutically acceptable salt thereof.

33. The method of claim 5, wherein the GvHD is acute GvHD.

34. The method of claim 5, wherein the GvHD is chronic GvHD.

* * * * *